(12) United States Patent
Murakami et al.

(10) Patent No.: US 10,753,860 B2
(45) Date of Patent: Aug. 25, 2020

(54) INSPECTION APPARATUS, INSPECTION METHOD, AND PROGRAM

(71) Applicant: Sony Corporation, Tokyo (JP)

(72) Inventors: Yoshihiro Murakami, Kanagawa (JP); Masatoshi Takashima, Tokyo (JP); Akira Matsui, Kanagawa (JP)

(73) Assignee: Sony Corporation, Tokyo (JP)

( * ) Notice: Subject to any disclaimer, the term of this patent is extended or adjusted under 35 U.S.C. 154(b) by 108 days.

(21) Appl. No.: 15/579,360

(22) PCT Filed: Jun. 24, 2016

(86) PCT No.: PCT/JP2016/068778
§ 371 (c)(1),
(2) Date: Dec. 4, 2017

(87) PCT Pub. No.: WO2017/010258
PCT Pub. Date: Jan. 19, 2017

(65) Prior Publication Data
US 2018/0180533 A1    Jun. 28, 2018

(30) Foreign Application Priority Data
Jul. 10, 2015    (JP) .................................. 2015-139138

(51) Int. Cl.
*G01N 21/27*    (2006.01)
*G01N 21/25*    (2006.01)
(Continued)

(52) U.S. Cl.
CPC ........... *G01N 21/255* (2013.01); *G01N 21/27* (2013.01); *G01N 21/3563* (2013.01);
(Continued)

(58) Field of Classification Search
CPC ............ G01J 2003/2826; G01J 3/2823; G01N 33/0098
See application file for complete search history.

(56) References Cited

U.S. PATENT DOCUMENTS 6,683,970 B1    1/2004    Satake et al.
8,244,477 B1    8/2012    Embaye et al.
(Continued)

FOREIGN PATENT DOCUMENTS

DE    102007023157 A1    11/2008
JP    2001-045867 A    2/2001
(Continued)

OTHER PUBLICATIONS

Extended European Search Report dated Jan. 29, 2019 for corresponding European Application No. 16824238.6.
(Continued)

*Primary Examiner* — Maurice C Smith
(74) *Attorney, Agent, or Firm* — Michael Best & Friedrich LLP

(57) ABSTRACT

The present technology relates an inspection apparatus, an inspection method and a program by which accurate measurement light correction can be performed.
The inspection apparatus calculates a correction gain of a spectrum based on reference spectral information, under a reference light source, of a reference reflector plate having a characteristic according to an inspection object and measurement spectral information of the reference reflector plate obtained by sensing under a measurement light source, and corrects measurement spectral information of the inspection object obtained by the sensing under the measurement light source based on the calculated correction gain. The present technology can be applied, for example, to a vegetation
(Continued)

inspection apparatus that measures a vegetation index of a normalized vegetation index (NDVI) or the like.

19 Claims, 41 Drawing Sheets

(51) Int. Cl.
    *G01N 21/3563*    (2014.01)
    *G01N 33/00*      (2006.01)
    *G01N 21/31*     (2006.01)

(52) U.S. Cl.
    CPC . *G01N 33/0098* (2013.01); *G01N 2021/3196* (2013.01); *G01N 2201/0636* (2013.01)

(56) References Cited

U.S. PATENT DOCUMENTS

| | | | | |
|---|---|---|---|---|
| 2001/0016053 A1* | 8/2001 | Dickson | ............... | G01J 3/2803 |
| | | | | 382/110 |
| 2002/0165684 A1* | 11/2002 | Olson | ............... | G01J 3/46 |
| | | | | 702/85 |
| 2005/0151965 A1* | 7/2005 | Bissett, III | ............... | G01J 3/28 |
| | | | | 356/328 |
| 2006/0013454 A1* | 1/2006 | Flewelling | ............. | A61B 1/042 |
| | | | | 382/128 |
| 2008/0046217 A1* | 2/2008 | Polonskiy | ................. | G01J 3/28 |
| | | | | 702/179 |
| 2010/0098342 A1* | 4/2010 | Davis | ................. | G06K 9/0063 |
| | | | | 382/220 |
| 2013/0107260 A1* | 5/2013 | Nozawa | ................... | G01J 3/42 |
| | | | | 356/402 |
| 2014/0022381 A1* | 1/2014 | Heinold | ................. | G01N 21/27 |
| | | | | 348/135 |
| 2014/0353475 A1* | 12/2014 | Meyers | ................. | G01J 1/0411 |
| | | | | 250/216 |
| 2015/0130936 A1 | 5/2015 | Coram et al. | | |
| 2016/0069741 A1* | 3/2016 | Ritter | ................... | G01J 3/0297 |
| | | | | 356/402 |

FOREIGN PATENT DOCUMENTS

| | | |
|---|---|---|
| JP | 2006-101768 A | 4/2006 |
| JP | 2006-317195 A | 11/2006 |

OTHER PUBLICATIONS

Japanese Office Action dated Jul. 14, 2020 for corresponding Japanese Application No. 2017-528354.

\* cited by examiner

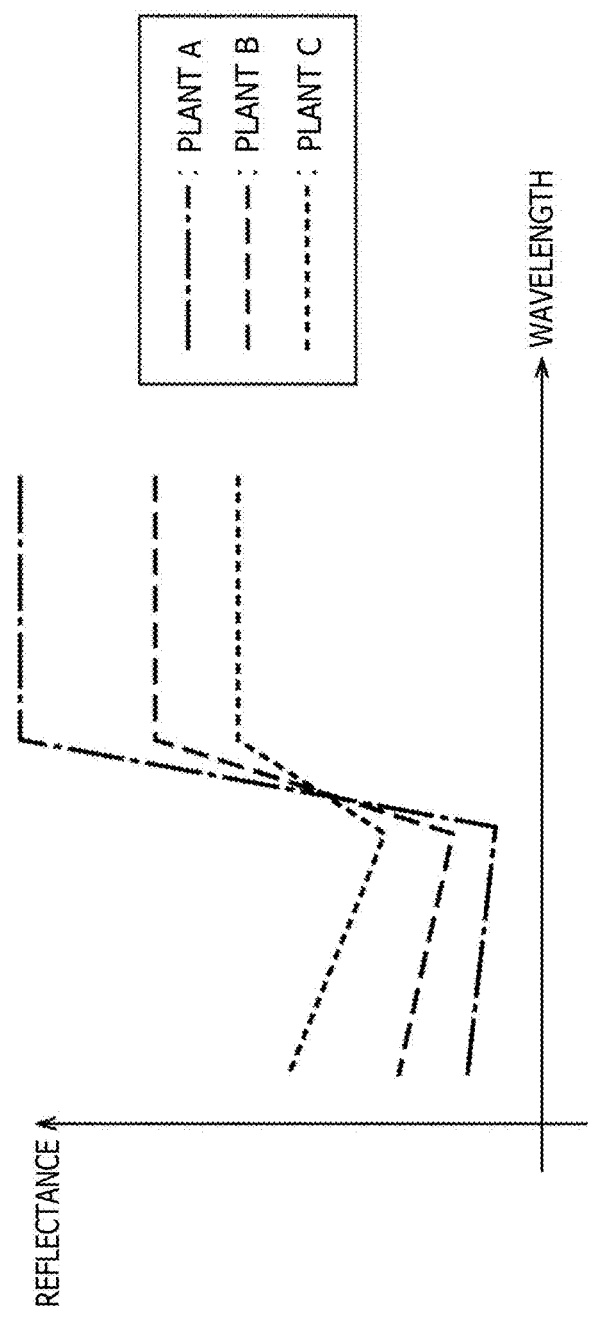
F I G. 1 0

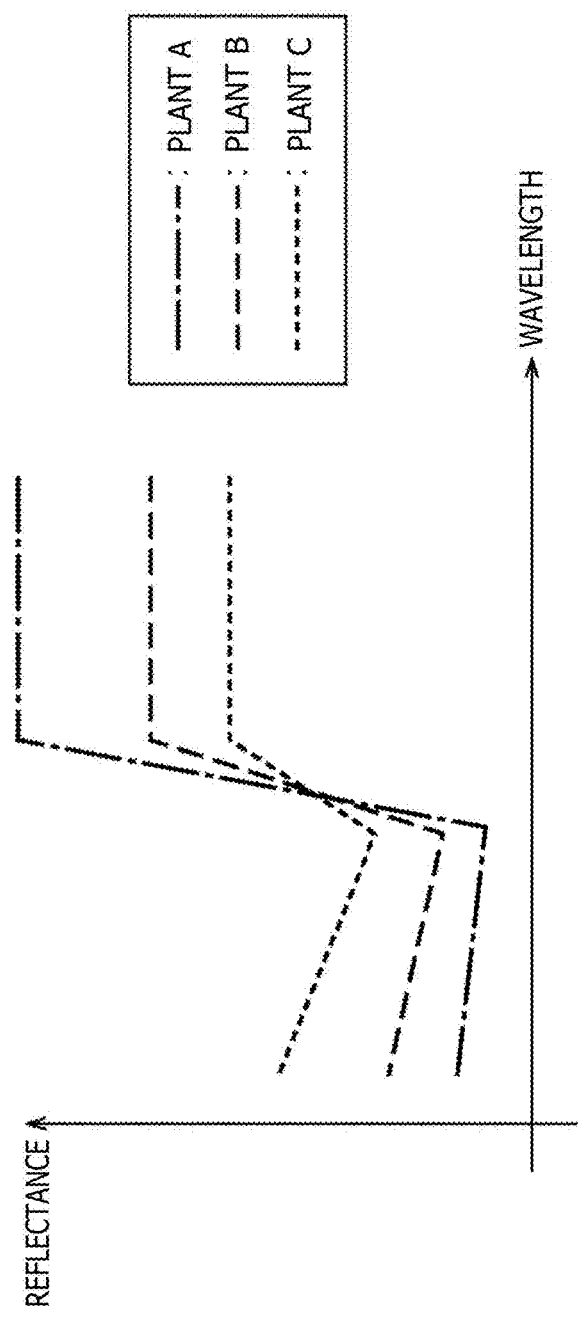
F I G . 1 5

FIG.32
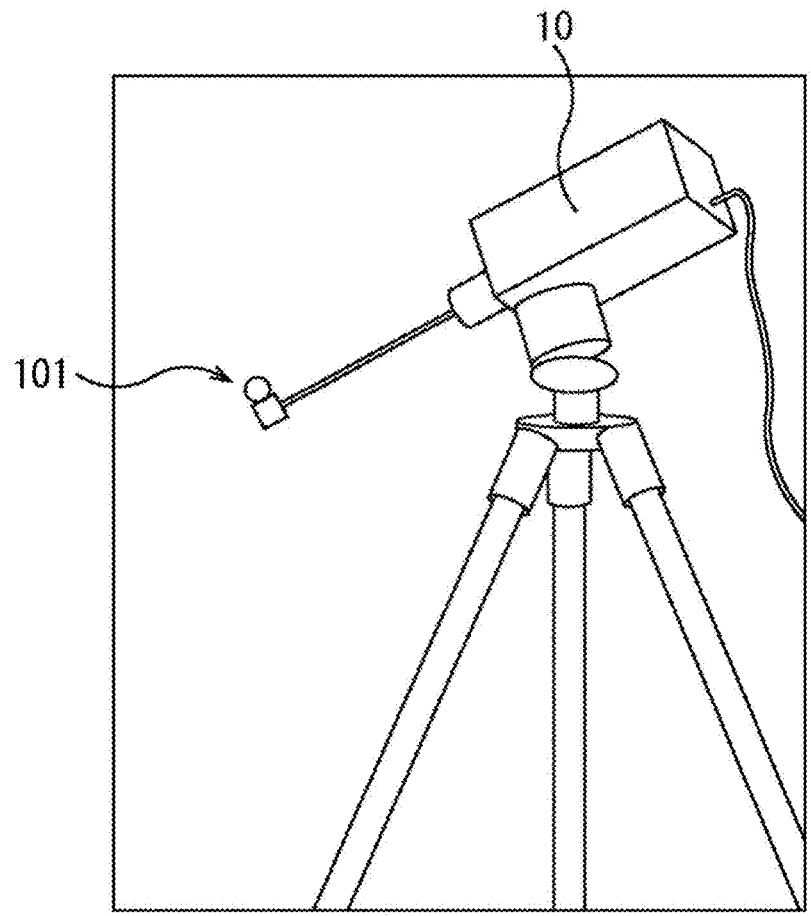
A
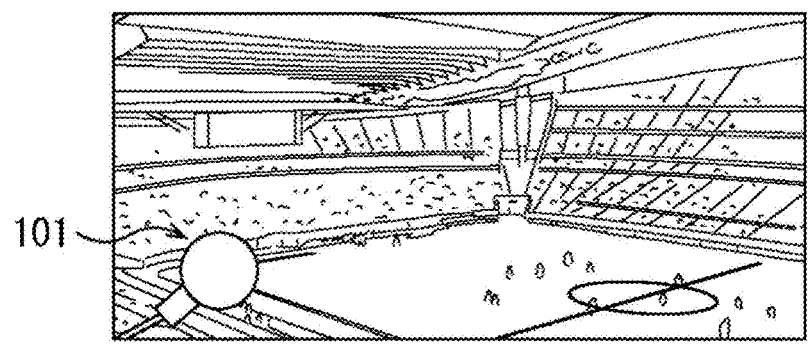
B

INSPECTION APPARATUS, INSPECTION METHOD, AND PROGRAM

TECHNICAL FIELD

The present technology relates an inspection apparatus, an inspection method and a program, and particularly to an inspection apparatus, an inspection method and a program by which accurate measurement light correction can be performed.

BACKGROUND ART

Conventionally, it is known to use, when measurement of an inspection index of an inspection object such as a plant is performed, a reference reflector plate in order to correct a variation of a measurement light source upon measurement (refer to, for example, PTL 1).

CITATION LIST

Patent Literature

PTL 1
  JP 2006-101768A

SUMMARY

Technical Problem

However, with the conventional technology, upon measurement of an inspection index of an inspection object, a variation of a measurement light source sometimes makes it difficult to perform accurate measurement light correction. Therefore, it is demanded to perform, upon measurement of an inspection index of an inspection object, accurate measurement light correction even if the measurement light source varies.

The present technology has been made in view of such a situation as described above and makes it possible to perform accurate measurement light correction by removing the light source dependency upon measurement of an inspection index of an inspection object.

Solution to Problem

The inspection apparatus according to one aspect of the present technology is an inspection apparatus including a correction gain calculation unit configured to calculate a correction gain of a spectrum based on reference spectral information, under a reference light source, of a reference reflector plate or a reference transmission plate having a characteristic according to an inspection object and measurement spectral information of the reference reflector plate or the reference transmission plate obtained by sensing under a measurement light source, and a correction unit configured to correct measurement spectral information of the inspection object obtained by the sensing under the measurement light source based on the calculated correction gain.

The inspection apparatus of the one aspect of the technology may be an independent apparatus or an internal block that configures one apparatus. Further, an inspection method or a program of the one aspect of the present technology is an inspection method or a program that corresponds to the inspection apparatus of the one aspect of the present technology described above.

In the inspection apparatus, inspection method and program of the one aspect of the present technology, a correction gain of a spectrum is calculated based on reference spectral information, under a reference light source, of a reference reflector plate or a reference transmission plate having a characteristic according to an inspection object and measurement spectral information of the reference reflector plate or the reference transmission plate obtained by sensing under a measurement light source, and measurement spectral information of the inspection object obtained by the sensing under the measurement light source is corrected based on the calculated correction gain.

Advantageous Effect of Invention

With the one aspect of the present technology, accurate measurement light correction can be performed.

It is to be noted that the effect described here is not necessarily restrictive but may be any effect described in the present disclosure.

BRIEF DESCRIPTION OF DRAWINGS

FIG. 10 is a view illustrating measurement of a spectral reflectance of plants of different vegetations.

FIG. 15 is a view illustrating measurement of a spectral reflectance of plants of different vegetations.

FIG. 32 is a view depicting an example of a case in which a reference reflector plate is attached in front of a camera.

DESCRIPTION OF EMBODIMENT

In the following, an embodiment of the present technology is described with reference to the drawings. It is to be noted that the description is given in the following order.
1. Configuration of System
2. Principle of Inspection in Which Reference Reflector Plate of Present Technology Is Used
3. Design of Reference Reflector Plate
4. Inspection of Inspection Object
(1) Measurement of Reference Reflector Plate under Reference Light Source
(2) Measurement of Inspection Index of Inspection Object under Measurement Light Source
5. Modifications
6. Configuration of Computer
<1. Configuration of System>
(Configuration of Vegetation Inspection Apparatus)

Figure 1:
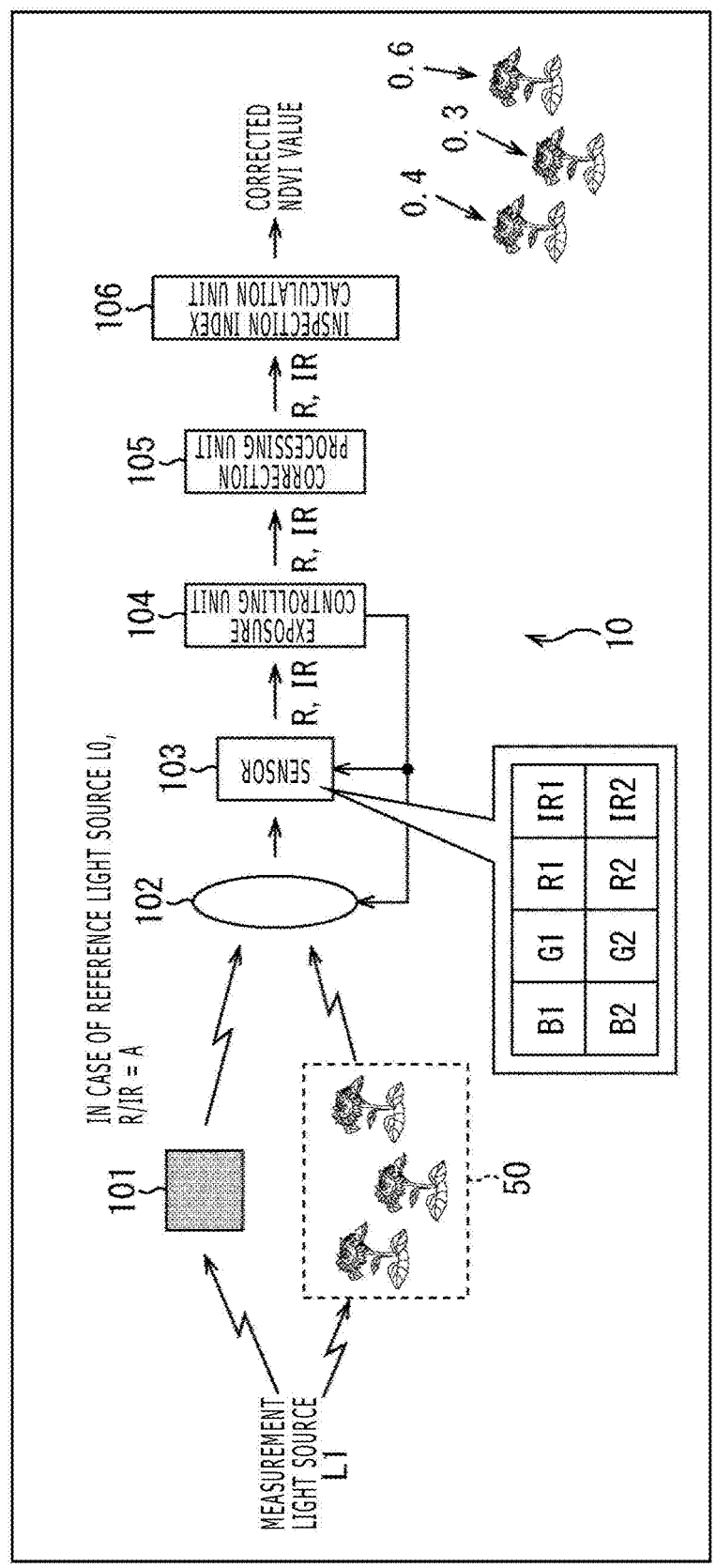
FIG. 1 is a view depicting an example of a configuration of a vegetation inspection apparatus to which the present technology is applied.
Figure 2:
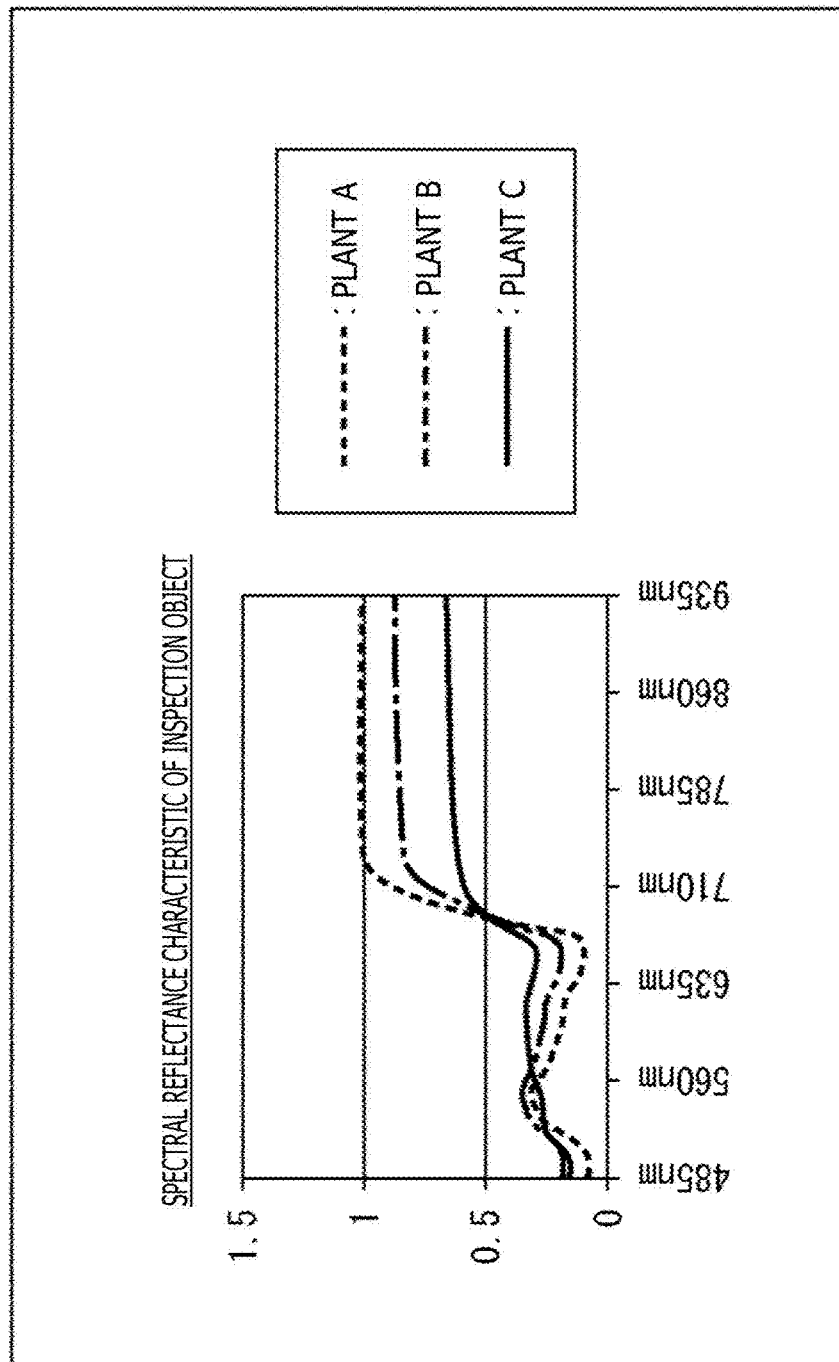
FIG. 2 is a view depicting a spectral reflectance characteristic of an inspection object.
Figure 3:
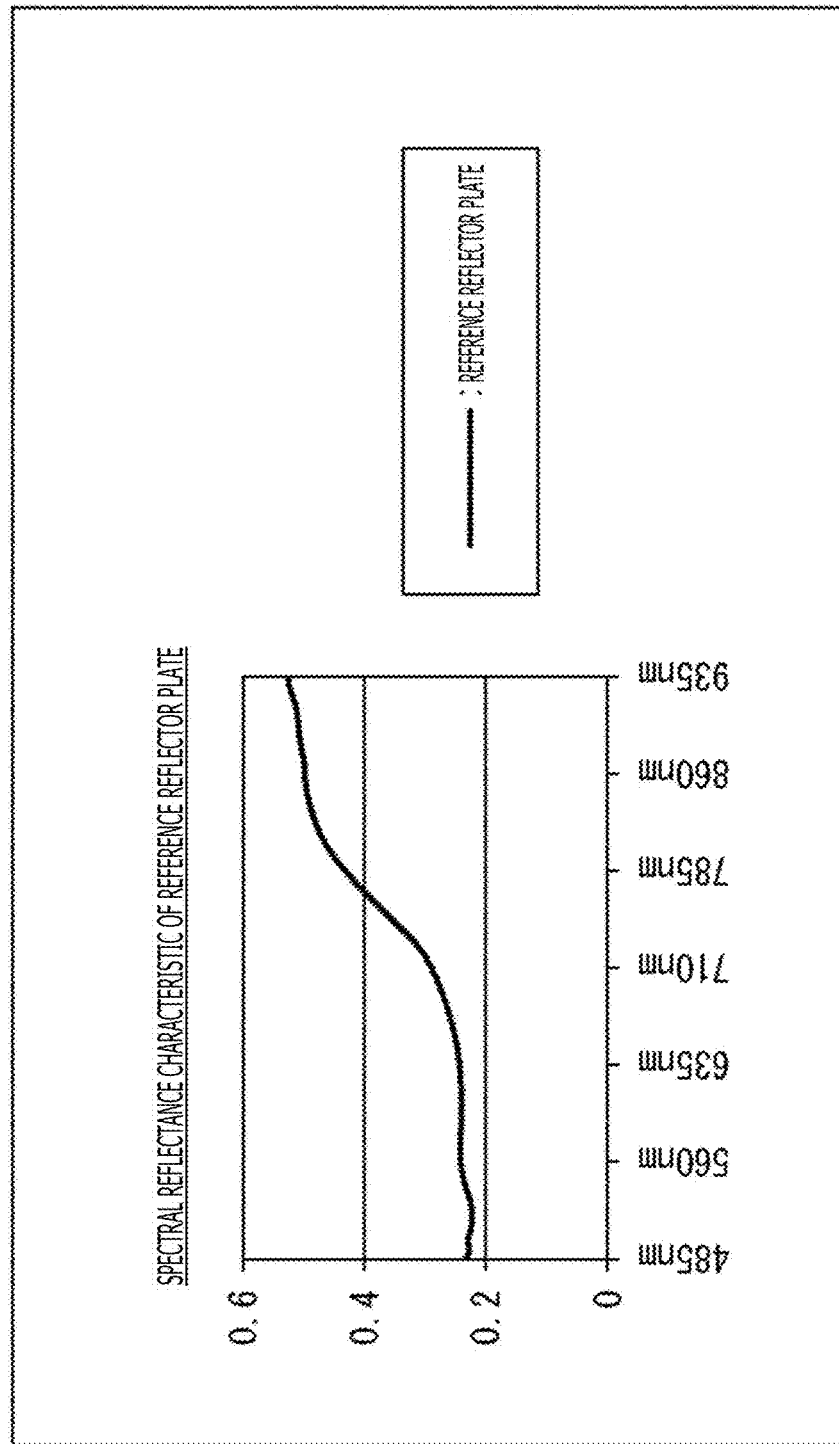
FIG. 3 is a view depicting a spectral reflectance characteristic of a reference reflector plate.
Figure 4:
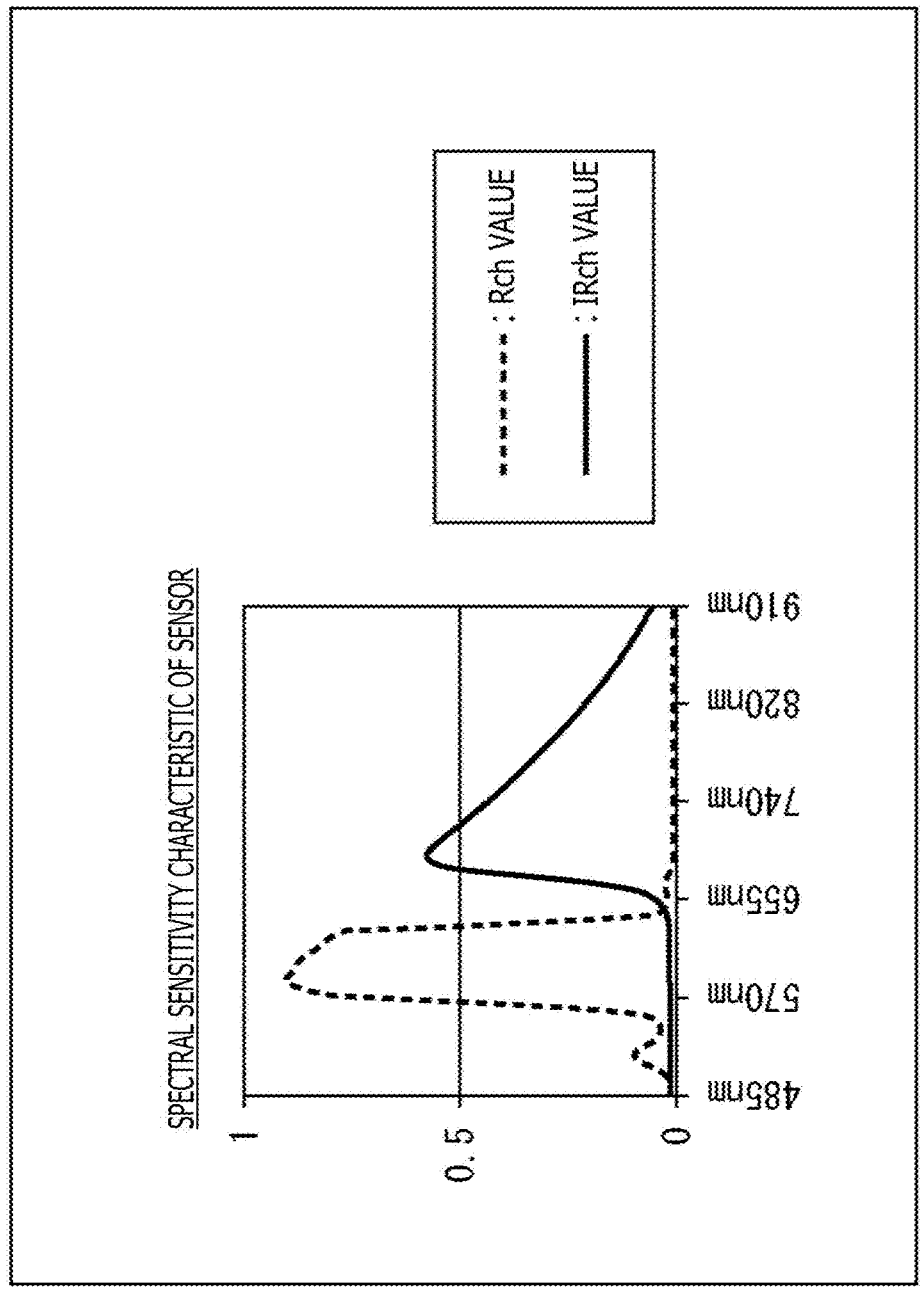
FIG. 4 is a view depicting a spectral sensitivity characteristic of a sensor.

FIG. 1 is a view depicting an example of a configuration of a vegetation inspection apparatus 10 to which the present technology is applied. It is to be noted that, in the description of FIG. 1, graphs of FIGS. 2 to 4 are suitably referred to.

The vegetation inspection apparatus 10 of FIG. 1 is an apparatus that performs sensing of an inspection object 50 such as a plant to perform measurement of an inspection index of the inspection object 50. Here, the term sensing signifies to measure an object. Further, the sensing includes to pick up an image of an object (image pickup object), and also a case in which sensing of light of a wavelength other than those of visible rays is performed is included in image pickup.

Referring to FIG. 1, the vegetation inspection apparatus 10 is configured from a reference reflector plate 101, a lens 102, a sensor 103, an exposure controlling unit 104, a correction processing unit 105, and an inspection index calculation unit 106. It is to be noted that the reference reflector plate 101 is installed at a predetermined position at which it can be measured (sensed) solely or simultaneously with the inspection object 50 by the vegetation inspection apparatus 10. It is to be noted that, in FIG. 1, the exposure controlling unit 104, correction processing unit 105, inspection index calculation unit 106 and so forth may be configured including circuitry.

In FIG. 1, a case is described in which, as the inspection object 50, a plant is an object, and a vegetation index is calculated as an inspection index of the plant. The vegetation index is an index indicative of a distribution situation or an activity of vegetations. In the following description, as the vegetation index, a normalized vegetation index (NDVI: Normalized Difference Vegetation Index) is described.

Further, in the following description, the term spectral ratio is a value representative of a relationship of spectra obtained by dispersing light from an object. Here, in order to determine a normalized vegetation index (NDVI value), since a value of an R (red) component and a value of an IR (infrared) component are required as a spectroscopic spectrum, the spectral ratio is a value representative of a relationship between an R component and an IR component.

As the spectral ratio in this instance, data may be of any type if the data represents a ratio of R and IR or values from which a ratio of R and IR can be determined such as, for example, a value obtained by calculating R/IR, a value obtained by calculating IR/R, or values of R and IR retained independently of each other. In the following description, a case in which, as the spectral ratio, a value obtained by calculating R/IR (hereinafter referred to also as "R/IR ratio") is used is described as an example.

Further, in the following description, a light source that illuminates an object upon measurement for determining a reference spectral ratio (R/IR ratio) of the reference reflector plate 101 under a certain specific light source is referred to as reference light source L0, and a light source that illuminates an object upon measurement of an inspection index of the inspection object 50 under various light sources is referred to as measurement light source L1 for distinction between them.

Under the measurement light source L1, reflection light from the inspection object 50 enters the sensor 103 through the lens 102.

FIG. 2 is a view depicting spectral reflectance characteristics of plants as the inspection object 50. In FIG. 2, the axis abscissa represents the wavelength (nm) and the axis of ordinate represents the reflectance. Further, a plant A, another plant B and a further plant C are plants of the same type (for example, turf) but are different in vegetation representative of the amount or the activity of the plants. As depicted in FIG. 2, the spectral reflectance characteristic differs among the plants of different vegetations.

Further, under the measurement light source L1, reflection light from the reference reflector plate 101 enters the sensor 103 through the lens 102. Here, the reference reflector plate 101 is produced such that it has a characteristic according to the spectral reflectance of the inspection object 50 (characteristic equal or close to the spectral reflectance of the inspection object 50).

FIG. 3 is a view depicting a spectral reflectance characteristic of the reference reflector plate 101. Referring to FIG. 3, the axis of abscissa represents the wavelength (nm) and the axis of ordinate represents the reflectance. As depicted in FIG. 3, the reference reflector plate 101 has a spectral reflectance characteristic according to the spectral reflectance characteristic of a plant depicted in FIG. 2. It is to be noted that the detailed substance of a design method of the reference reflector plate 101 is hereinafter described with reference to FIGS. 7 to 18.

The sensor 103 is configured, for example, from a spectroscope having a plurality of optical filters that transmit light of predetermined wavelength bands, and a sensing element including a plurality of pixels arrayed in a matrix on a sensor face thereof and has a spectroscopic sensing function. The sensor 103 disperses, by the spectroscope thereof, light (reflection light) from objects (inspection object 50 and reference reflector plate 101) incident thereto through the lens 102 and detects, by the sensing element thereof, light irradiated upon the sensor face to output measurement signals (measurement values) according to the brightness values of the respective spectral components.

As depicted in FIG. 1, in the spectroscope of the sensor 103, for example, 8 pixels with length×width of 2×4 are set as one set, and eight different optical filters that pass light of wavelength bands different from each other are arranged corresponding to the pixels configuring the one set. In particular, corresponding to 8 pixels of one set, an optical filter that passes first blue light B1, an optical filter that passes second blue light B2, an optical filter that passes first blue light G1, an optical filter that passes second blue light G2, an optical filter that passes first red light R1, an optical filter that passes second red light R2, an optical filter that passes first infrared light IR1 and an optical filter that passes second infrared light IR2 are arranged in an ascending order of the wavelength.

Further, the spectroscope is configured, defining such optical filters of 8 pixels as described above as one set, from n sets (n is a natural number equal to or greater than 1) optical filters arranged successively over an overall area of the sensor face of the sensing element. It is to be noted that the set of optical filters is not limited to the configuration in which 8 pixels are set as one set, but different forms such as, for example, a configuration in which four pixels are set as one set can be adopted.

Here, where a normalized vegetation index (NDVI value) is measured as the vegetation index, since measurement values of the R (red) component and the IR (infrared) component are required, the sensor 103 measures (senses) a value of the R component (R channel (Rch) value) and a value of the IR component (IR channel (IRch) value) in response to light (reflection light) from objects and supplies the values to the exposure controlling unit 104 and the correction processing unit 105.

It is to be noted that the value of the R component (R channel value) is a measurement value corresponding, for example, to the optical filter that passes the first red light R1 or a measurement value corresponding to the optical filter that passes the second red light R2. Meanwhile, the value of the IR component (IR channel value) is a measurement value corresponding, for example, to the optical filter that passes the first infrared light IR1 or a measurement value corresponding to the optical filter that passes the second infrared light IR2.

FIG. 4 is a view depicting a spectral sensitivity characteristic of the sensor 103. Referring to FIG. 4, the axis of abscissa represents the wavelength (nm) and the axis of ordinate represents the spectral sensitivity. Here, it is known that, if the inspection object 50 is a plant, then the reflection in the visible region is small and the reflection in the near infrared region is great. This is because the spectral reflectance characteristic has a relationship with photosynthesis of a plant such that wavelengths in the visible region that is effective for photosynthesis are absorbed to decrease the reflection from the visible region while the reflection is relatively great in the near infrared region. The sensor 103 has the spectral sensitivity characteristic depicted in FIG. 4 in order to cope with such a spectral reflection characteristic of a plant.

It is to be noted that, for the sensor 103, not only an area sensor that captures an object by plane but also a line sensor that captures an object by line can be used. Further, even where only one pixel is arranged as each of a pixel for the R component and a pixel for the IR component on the sensing element, an object can be scanned if a mechanism for moving the sensor or the measurement object is provided.

The exposure controlling unit 104 controls the shutter speed of an optical system and the aperture amount by an iris (aperture) of the lens 102 and so forth, the shutter speed of an electronic shutter of the sensor 103 or the like such that measurement (sensing) is performed in a state in which signal charge remains within a dynamic range without being saturated in the sensor 103 to perform exposure control.

The correction processing unit 105 performs, on the basis of the R channel value and the IR channel value supplied thereto from the sensor 103, a correction process for correcting the spectral ratio (R/IR ratio) between the R channel value and the IR channel value and supplies information indicative of the spectral ratio (R/IR ratio) after correction to the inspection index calculation unit 106.

In this correction process, a correction gain of the spectral ratio (R/IR ratio) is calculated on the basis of the reference spectral ratio (R/IR ratio) of the reference reflector plate 101 under the reference light source L0 and the measurement spectral ratio (R/IR ratio) of the reference reflector plate 101 obtained by the measurement (sensing) under the measurement light source L1, and the correction gain is used to correct the measurement spectral ratio (R/IR ratio) of the inspection object 50 obtained by the measurement (sensing) under the measurement light source L1.

The inspection index calculation unit 106 calculates and outputs a vegetation index using the information supplied from the correction processing unit 105 and indicative of the measurement spectral ratio (R/IR ratio) of the inspection object 50 after correction. Here, the (corrected) NDVI value can be determined as a vegetation index by arithmetically operating an expression (1) given below.

$$\text{NDVI}=(IR-R)/(IR+R)=(1-R/IR)/(1+R/IR) \qquad (1)$$

It is to be noted that, in the expression (1), IR represents the reflectance in the near infrared region and R represents the reflectance in the visible region (red). It is to be noted that the detailed substance of the inspection method of the inspection object 50 such as to calculate a normalized vegetation index (NDVI value) is hereinafter described with reference to FIGS. 19 to 29.

The vegetation inspection apparatus 10 is configured in such a manner as described above. In the vegetation inspection apparatus 10 of FIG. 1, the reference spectral ratio (R/IR=A) of the reference reflector plate 101 under the reference light source L0 is determined such that, upon later measurement of an inspection index of the inspection object 50 under the measurement light source L1, the measurement spectral ratio (R/IR ratio) of the inspection object 50 under the measurement light source L1 is corrected using the reference spectral ratio (R/IR=A) of the reference reflector plate 101 and a correction gain determined from the measurement spectral ratio (R/IR ratio) of the reference reflector plate 101 under the measurement light source L1.

For example, if 0.6 is measured as the NDVI value of the inspection object 50 (specific plant) under the measurement light source L1 by the vegetation inspection apparatus 10 of FIG. 1, then the NDVI value of 0.6 corresponds to the NDVI value of the inspection object 50 under the reference light source L0, and even if the light source varies by a variation of the weather such as a fine, cloudy or rainy weather, since the light source dependency is removed, 0.6 is measured as the NDVI value if the object is the same inspection object 50 (specific plant). Further, this applies also to a case in which a value of, for example, 0.3 or 0.4 is measured as the NDVI value of a different inspection object 50 of a different vegetation under the measurement light source L1, and such values correspond to the NDVI values of the inspection object 50 under the reference light source L0 and are measured as values from which the light source dependency is removed. On the other hand, different from the vegetation inspection apparatus 10, if the light source dependency is not removed, then if the light source varies by a change of the weather such as, for example, a fine weather or a cloudy weather, then even if the object is the same inspection object (plant), the NDVI value is measured as a different value.

<2. Principle of Inspection in which Reference Reflector Plate of Present Technology is Used>

Figure 5:
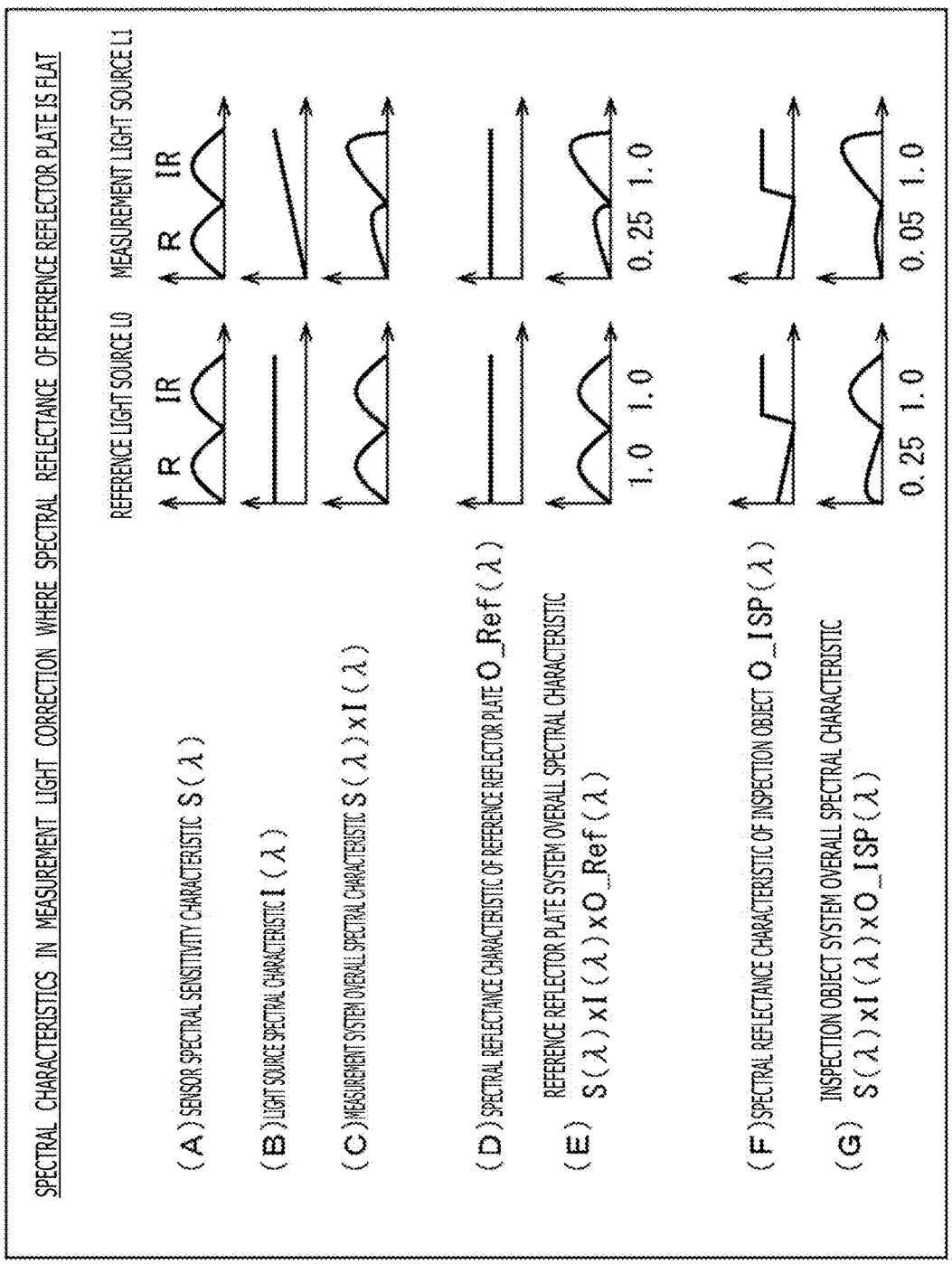
FIG. 5 is a view depicting spectral characteristics in measurement light correction where the spectral reflectance of the reference reflector plate is flat.
Figure 6:
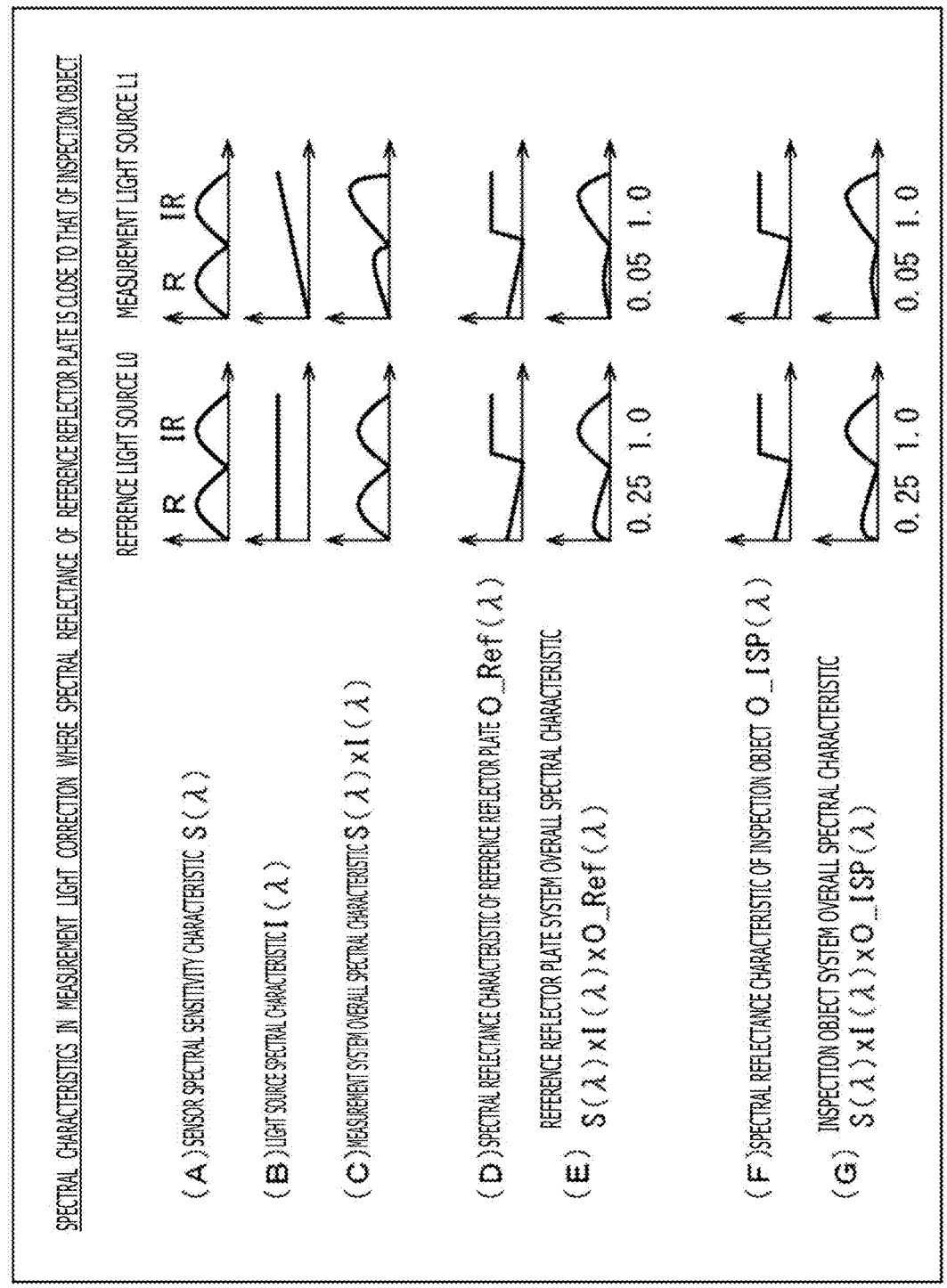
FIG. 6 is a view depicting spectral characteristics in measurement light correction where the spectral reflectance of the reference reflector plate is close to that of an inspection object.

Here, in what manner spectral characteristics of a light source and an object (inspection object 50 and reference reflector plate 101) act on the output value of the sensor 103, the spectral ratio (R/IR ratio) and the measurement light correction is indicated with reference to FIGS. 5 and 6 to describe a principle of an inspection performed by the vegetation inspection apparatus 10.

It is to be noted here that, after a case in which a reference reflector plate having a flat spectral reflectance characteristic (hereinafter referred to as flat reference reflector plate 101F) is described with reference to FIG. 5 for comparison, a case in which the reference reflector plate 101 (FIG. 1) having a spectral reflectance characteristic equal or close to the spectral reflectance characteristic or the inspection object 50 is described with reference to FIG. 6.

(Where Spectral Reflectance of Reference Reflector Plate is Flat)

FIG. 5 is a view illustrating a case in which the reference reflector plate 101F having a flat spectral reflectance is used as the reference reflector plate. It is to be noted that, in FIG. 5, the axis of abscissa of each graph represents the wavelength, and the axis of ordinate represents the intensity.

In the graphs of the reference light source L0 and the measurement light source L1 of the sensor spectral sensitivity characteristic $S(\lambda)$ of A of FIG. 5, the left side waveform represents a spectral sensitivity characteristic of the R channel and the right side waveform represents a spectral sensitivity characteristic of the IR channel. It is to be noted that the intensity of the axis of ordinate of A of FIG. 5 represents the intensity of light measured by the sensor 103.

In the light source spectral characteristic $I(\lambda)$ of B of FIG. 5, the graph of the reference light source L0 represents a characteristic in the case in which the spectral characteristic is flat, and the graph of the measurement light source L1 represents a characteristic that, as the wavelength increases, the spectral characteristic increases in intensity. It is to be noted that the intensity of the axis of ordinate of B of FIG. 5 represents an intensity of light radiated by each light source.

The measurement system overall spectral characteristic of C of FIG. 5 represents $S(\lambda) \times I(\lambda)$, namely, a spectral characteristic that is the product of the sensor spectral sensitivity characteristic $S(\lambda)$ of A of FIG. 5 and the light source spectral characteristic $I(\lambda)$ of B of FIG. 5. This represents an overall spectral characteristic of the measurement system taking both a characteristic of the light source and a characteristic of the sensor under the different light sources into consideration. It is to be noted that the intensity of the axis of ordinate of C of FIG. 5 represents an intensity obtained by multiplying the light intensity of A of FIG. 5 and the light intensity of B of FIG. 5.

It is assumed that, in the following description, measurement (sensing) of an object such as the reference reflector plate 101F or the inspection object 50 is assumed and the description is given using an R channel value and an IR channel value that are output values of the sensor 103. Here, the output values of the sensor 103 vary in proportion to a value obtained by multiplying the measurement system overall spectral characteristic $S(\lambda) \times I(\lambda)$ and $O\_Ref(\lambda)$ or $O\_ISP(\lambda)$ that is a spectral reflectance characteristic of each of the objects (reference reflector plate 101F and inspection object 50) and then integrating the products on the wavelength axis.

First, measurement of the spectral ratio (R/IR ratio) by measurement (sensing) of the reference reflector plate 101F under the reference light source L0, measurement of the spectral ratio (R/IR ratio) by measurement (sensing) of the reference reflector plate 101F under the measurement light source L1 and calculation of a correction gain that is used by measurement light correction are described with reference to D of FIG. 5 and E of FIG. 5.

D of FIG. 5 represents the spectral reflectance characteristic $O\_Ref(\lambda)$ of the reference reflector plate 101F, and the value of the same is flat. Meanwhile, the reference reflector plate system overall spectral characteristic of E of FIG. 5 represents a characteristic obtained by multiplying the measurement system overall spectral characteristic $S(\lambda) \times I(\lambda)$ of C of FIG. 5 and the spectral reflectance characteristic $O\_Ref(\lambda)$ of the reference reflector plate 101F of D of FIG. 5. Further, the output value of the sensor 103 varies in proportion to the value obtained by integrating the characteristic of E of FIG. 5 on the wavelength axis (area of a region surrounded by a solid line representative of the light intensity or F of FIG. 5 and the wavelength axis). It is to be noted that the intensity of the axis of ordinate of D of FIG. 5 represents the intensity of light reflected by the reference reflector plate 101F. Meanwhile, the intensity of the axis of ordinate of E of FIG. 5 represents as intensity obtained by multiplying the light intensity of C of FIG. 5 and the light intensity of D of FIG. 5.

Here, it is assumed that the R channel value and the IR channel value under the reference light source L0 upon measurement of the reference reflector plate 101F are represented by D_Ref_L0_R=1.0 and D_Ref_L0_IR=1.0, respectively. In this case, the spectral ratio (R/IR ratio) of the reference reflector plate 101E under the reference light source L0 is calculated by an expression (2) given below.

$$R\_Ref\_L0 = D\_Ref\_L0\_R/D\_Ref\_L0\_IR = 1.0/1.0 = 1.0 \quad (2)$$

Meanwhile, under a different light source in measurement of an inspection index (NDVI value) of the inspection object 50, a correction gain for correcting the spectral ratio (R/IR ratio) of the reference reflector plate 101E to the value of the expression (2) is calculated. Here, it is assumed that, under the measurement light source L1, the R channel value and the IR channel value upon measurement of the reference reflector plate 101E are D_Ref_L1_R=0.25 and D_Ref_L1_IR=1.0, respectively. In this case, the spectral ratio (R/IR ratio) of the reference reflector plate 101E under the measurement light source L1 is calculated by an expression (3) given below.

$$R\_Ref\_L1 = D\_Ref\_L2\_R/D\_Ref\_L1\_IR = 0.25/1.0 = 0.25 \quad (3)$$

Therefore, the correction gain by the light source variation is calculated by an expression (4) given below.

$$G\_Ref\_L1 = R\_Ref\_L0/R\_Ref\_L1 = 1.0/0.25 \le 4.0 \quad (4)$$

It is to be noted that, where the measurement light source L1 coincides with the reference light source L0, the correction gain is calculated by an expression (5) given below. In particular, in this case, the correction gain is equivalent to that in the case of non-correction as indicated by the expression (5) given below.

$$G\_Ref\_L0 = R\_Ref\_L0/R\_Ref\_L0 = 1.0/1.0 = 1.0 \quad (5)$$

Now, measurement of the spectral ratio (R/IR ratio) by measurement (sensing) of the inspection object 50 under the individual light sources and measurement light correction using the correction gain determined by the expression (4) are described with reference to F of FIG. 5 and G of FIG. 5.

F of FIG. 5 represents an example of the spectral reflectance characteristic O_ISP(λ) of the inspection object 50, and the value is not flat. Meanwhile, the inspection object system overall spectral characteristic of G of FIG. 5 represents a characteristic obtained by multiplying the measurement system overall spectral characteristic S(λ)×I(λ) of C of FIG. 5 and the spectral reflectance characteristic O_ISP(λ) of the inspection object 50 of F of FIG. 5. Further, the output value of the sensor 103 varies in proportion to the value obtained by integrating the characteristic of G of FIG. 5 on the wavelength axis (area of a region surrounded by a solid line representative of the light intensity of G of FIG. 5 and the wavelength axis). It is to be noted that the intensity of the axis of ordinate of F of FIG. 5 represents the intensity of light reflected by the inspection object 50. Meanwhile, the intensity of G of FIG. 5 represents an intensity obtained by multiplying the light intensity of C of FIG. 5 and the light intensity of F of FIG. 5.

Here, it is assumed that the R channel value and the IR channel value under the reference light source L0 upon measurement of the inspection object 50 are represented by D_ISP_L0=0.25 and D_ISP_L0_IR=1.0, respectively. In this case, the spectral ratio (R/IR ratio) of the inspection object 50 under the reference light source L0 is calculated by an expression (6) given below.

$$R\_ISP\_L0 = D\_ISP\_L0\_R/D\_ISP\_L0\_IR = 0.25/1.0 = 0.25 \quad (6)$$

Then, the measurement light correction for the spectral ratio (R/IR ratio) determined by the expression (6) above is represented, using the correction gain determined by the expression (5), by an expression (7) given below and is constant.

$$R\_ISP\_L0\_comp = R\_ISP\_L0 \times G\_Ref\_L0 = 0.25 \times 1.0 = 0.25 \quad (7)$$

In the meantime, it is assumed that the R channel value and the IR channel value upon measurement of the inspection object 50 under the measurement light source L1 are D_ISP_L1_R=0.05 and D_ISP_L1_IR=1.0, respectively. In this case, the spectral ratio (R/IR ratio) of the inspection object 50 under the measurement light source L1 is calculated by an expression (8) given below.

$$R\_ISP\_L1 = D\_ISP\_L1\_R/D\_ISP\_L1\_IR = 0.05/1.0 = 0.05 \quad (8)$$

Then, the measurement light correction for the spectral ratio (R/IR ratio) determined by the expression (8) is represented using the correction gain determined by the expression (4) by an expression (9) given below.

$$R\_ISP\_L1\_comp = R\_ISP\_L1 \times G\_Ref\_L1 = 0.05 \times 4.0 = 0.2 \quad (9)$$

The measurement light correction is performed in such a manner as described above. However, although, from a point of view of the correction accuracy in measurement light correction for the spectral ratio (R/IR ratio) of the inspection object 50, the measurement value under the measurement light source L1 (R_ISP_L1=0.05) is much different from the measurement value under the reference light source L0 (R_ISP_L0=0.25), it is corrected to a closer value (R_ISP_L1_comp=0.2) by the measurement light correction applying the expression (9). However, even where the measurement light correction is performed, there still remains an error.

This arises from the fact that, although the correction gain to the spectral ratio (R/IR ratio) corresponding to the output value of the sensor 103 for the spectral characteristic of G of FIG. 5 is determined from the spectral ratio (R/IR ratio) corresponding to the output value of the sensor 103 for the spectral characteristic of E of FIG. 5, since a great difference in component of the spectral reflectance of the object (O_Ref(λ) and O_ISP(λ)) exists between G of FIG. 5 and E of FIG. 5, the applied correction gain is not a correction gain having a high degree of accuracy with respect to the inspection object 50.

(Where Spectral Reflection Characteristic of Reference Reflector Plate is Equal or Close to that of Inspection Object)

FIG. 6 is a view illustrating a case in which the reference reflector plate 101 (FIG. 1) whose spectral reflectance is equal or close to the spectral reflectance characteristic of the inspection object 50 is used as the reference reflector plate. It is to be noted that, in FIG. 6, the axes of the graphs are similar to those of the graphs of FIG. 5.

Since the sensor spectral sensitivity characteristic S(λ) of A of FIG. 6, light source spectral characteristic I(λ) of B of FIG. 6 and measurement system overall spectral characteristic S(λ)×I(λ) of C of FIG. 6 are similar to the sensor spectral sensitivity characteristic S(λ) of A of FIG. 5, light source spectral characteristic I(λ) of B of FIG. 5 and measurement system overall spectral characteristic $S(\lambda) \times I(\lambda)$ of C of FIG. 5, respectively, description of them is omitted.

First, measurement of a spectral ratio (R/IR ratio) by measurement (sensing) of the reference reflector plate 101 under the reference light source L0, measurement of the spectral ratio (R/IR ratio) by measurement (sensing) of the reference reflector plate 101 under the measurement light source L1 and calculation of a correction gain that is used by measurement light correction are described with reference to D of FIG. 6 and E of FIG. 6.

D of FIG. 6 represents the spectral reflectance characteristic $O\_Ref(\lambda)$ of the reference reflector plate 101. Here, it is assumed that the spectral reflectance characteristic is a representative characteristic of the inspection object 50 that indicates a variation in characteristic. For example, where the inspection object 50 is a plant, the vegetation of it varies as a characteristic. Further, as a representative characteristic, for example, an average value or the like can be adopted. Further, the reference reflector plate system overall spectral characteristic of E of FIG. 6 represents a characteristic obtained by multiplying the measurement system overall spectral characteristic $S(\lambda) \times I(\lambda)$ of C of FIG. 6 and the spectral reflectance characteristic $O\_Ref(\lambda)$ of the reference reflector plate 101 of D of FIG. 6.

Here, it is assumed that the R channel value and the IR channel value under the reference light source L0 upon measurement of the reference reflector plate 101 are represented by $D\_Ref\_L0\_R=0.25$ and $D\_Ref\_L0\_IR=1.0$, respectively. In this case, the spectral ratio (R/IR ratio) of the reference reflector plate 101 under the reference light source L0 is calculated by an expression (10) given below.

$$R\_Ref\_L0=D\_Ref\_L0\_R/D\_Ref\_L0\_IR=0.25/1.0=0.25 \quad (10)$$

Meanwhile, under a different light source in measurement of the inspection index (NDVI value) of the inspection object 50, a correction gain for correcting the spectral ratio (R/IR ratio) of the reference reflector plate 101 to the value of the expression (10) is calculated. Here, it is assumed that, under the measurement light source L1, the R channel value and the IR channel value upon measurement of the reference reflector plate 101 are $D\_Ref\_L1\_R=0.05$ and $D\_Ref\_L1\_IR=1.0$, respectively. In this case, the ratio R/IR of the reference reflector plate 101 under the measurement light source L1 is calculated by an expression (11) given below.

$$R\_Ref\_L1=D\_Ref\_L1\_R/D\_Ref\_L1\_IR=0.05/1.0=0.05 \quad (11)$$

Therefore, the correction gain by the light source variation is calculated by an expression (12) given below.

$$G\_Ref\_L1=R\_Ref\_L0/R\_Ref\_L1=0.25/0.5=5.0 \quad (12)$$

It is to be noted that, where the measurement light source L1 coincides with the reference light source L0, the correction gain is calculated by an expression (13) given below. In particular, in this case, the correction gain is equivalent to that in the case of non-correction as indicated by the expression (13) given below.

$$G\_Ref\_L0=R\_Ref\_L0/R\_Ref\_L0=0.25/0.25=1.0 \quad (13)$$

Now, measurement of the spectral ratio (R/IR ratio) by measurement (sensing) of the inspection object 50 under the individual light sources and measurement light correction using the correction gain determined by the expression (12) are described with reference to F of FIG. 6 and G of FIG. 6.

F of FIG. 6 represents an example of the spectral reflectance characteristic $O\_ISP(\lambda)$ of the inspection object 50, and the value is not flat. It is to be noted here that, since the reference reflector plate 101 is produced such that the spectral reflectance characteristic $O\_Ref(\lambda)$ of the reference reflector plate 101 coincides with a representative characteristic (for example, an average value or the like) of the inspection object 50 that has a variation in characteristic (for example, a vegetation of a plant or the like), the spectral reflectance characteristic $O\_REF(\lambda)$ of the reference reflector plate 101 and the spectral reflectance characteristic $O\_ISP(\lambda)$ of the inspection object 50 do not necessarily coincide with each other. It is to be noted here that, as the most effective example, a case in which the spectral reflectance characteristic $O\_REF(\lambda)$ of the reference reflector plate 101 and the spectral reflectance characteristic $O\_ISP(\lambda)$ of the inspection object 50 coincide with each other is described.

The inspection object system overall spectral characteristic of G of FIG. 6 represents a characteristic obtained by multiplying the measurement system overall spectral characteristic $S(\lambda) \times I(\lambda)$ of C of FIG. 6 and the spectral reflectance characteristic $O\_ISP(\lambda)$ of the inspection object 50 of F of FIG. 6.

Here, it is assumed that the R channel value and the IR channel value under the reference light source L0 upon measurement of the inspection object 50 are represented by $D\_ISP\_L0\_R=0.25$ and $D\_ISP\_L0\_IR=1.0$, respectively. In this case, the spectral ratio (R/IR ratio) of the inspection object 50 under the reference light source L0 is calculated by an expression (14) given below.

$$R\_ISP\_L0=D\_ISP\_L0\_R/D\_ISP\_L0\_IR=0.25/1.0=0.25 \quad (14)$$

Then, the measurement light correction for the spectral ratio (R/IR ratio) determined by the expression (14) above is represented, using the correction gain determined by the expression (13), by an expression (15) given below and is constant.

$$R\_ISP\_L0\_comp=R\_ISP\_L0 \times G\_Ref\_L0=0.25 \times 1.0=0.25 \quad (15)$$

On the other hand, it is assumed that the R channel value and the IR channel value upon measurement of the inspection object 50 under the measurement light source L1 are $D\_ISP\_L1\_R=0.05$ and $D\_ISP\_L1\_IR=1.0$, respectively. In this case, the spectral ratio (R/IR ratio) of the inspection object 50 under the measurement light source L1 is calculated by an expression (16) given below.

$$R\_ISP\_L1=D\_ISP\_L1\_R/D\_ISP\_L1\_IR=0.05/1.0=0.05 \quad (16)$$

Then, the measurement light correction for the spectral ratio (R/IR ratio) determined by the expression (16) is represented using the correction gain determined by the expression (12) by an expression (17) given below.

$$R\_ISP\_L1\_comp=R\_ISP\_L1 \times G\_Ref\_L1=0.05 \times 5.0=0.25 \quad (17)$$

The measurement light correction is performed in such a manner as described above. However, although, from a point of view of the correction accuracy in measurement light correction for the spectral ratio (R/IR ratio) of the inspection object 50, the measurement value under the measurement light source L1 ($R\_ISP\_L1=0.05$) is much different from the measurement value under the reference light source L0 ($R\_ISP\_L0=0.25$). Is corrected to the same value (R_ISP_L1_comp=0.25) by the measurement light correction applying the expression (17).

In regard to a reason therefor, this arises from the fact that, although the correction gain to the spectral ratio (R/IR ratio) corresponding to the output of the sensor 103 for the spectral characteristic of G of FIG. 6 is determined from the spectral ratio (R/IR ratio) corresponding to the output of the sensor 103 for the spectral characteristic of F of FIG. 6, since the components (O_Ref($\lambda$) and O_ISP($\lambda$) of the spectral reflectance in G of FIG. 6 and F of FIG. 6 have a same characteristic, the applied correction gain can become a correction gain that does not cause the inspection object 50 to generate a correction error.

It is to be noted that, although a case in which the spectral reflectance characteristic O_Ref($\lambda$) of the reference reflector plate 101 and the spectral reflectance characteristic O_ISP ($\lambda$) of the inspection object 50 are equal to each other is described with reference to FIG. 6, even in a case in which the spectral reflectance characteristics are not fully equal to each other as in FIG. 6, if a representative characteristic that has no correlation or has a low correlation with the spectral reflectance characteristic O_ISP($\lambda$) of the inspection object 50 but has a high correlation with the spectral reflectance characteristic O_ISP($\lambda$) of the inspection object 50 is used as the spectral reflectance characteristic O_Ref($\lambda$) of the reference reflector plate 101, then the error in measurement light correction can be minimized. Here, as a technique for deciding whether the correlation is high or low, for example, a relationship in magnitude of a value obtained by integrating, on the wavelength axis, a difference absolute value at each wavelength between the spectral reflectance characteristic O_Ref($\lambda$) of the reference reflector plate 101 and the spectral reflectance characteristic O_ISP($\lambda$) of the inspection object 50 can be used.

<3. Design of Reference Reflector Plate>

Now, a design method of the reference reflector plate 101 used in the vegetation inspection apparatus 10 (FIG. 1) is described.

(Configuration of Spectral Reflectance Design Apparatus)

Figure 7:
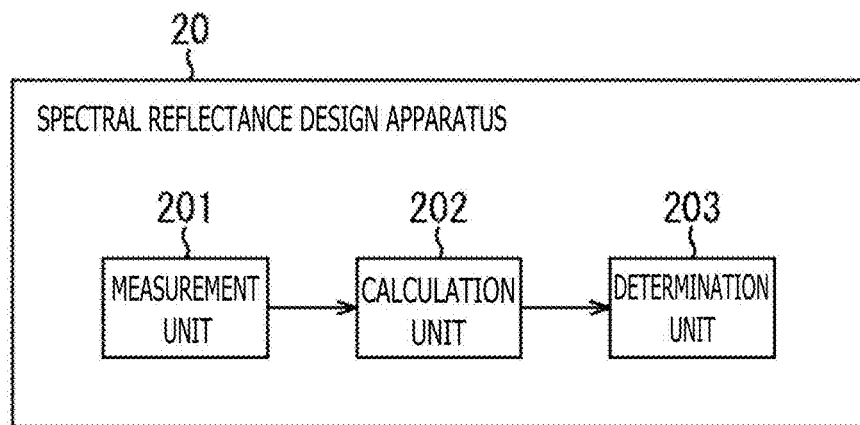
FIG. 7 is a view depicting an example of a configuration of a spectral reflectance design apparatus.

FIG. 7 is a view depicting an example of a configuration of a spectral reflectance design apparatus.

The spectral reflectance design apparatus 20 of FIG. 7 is an apparatus for performing design of the reference reflector plate 101 that is used in the vegetation inspection apparatus 10 (FIG. 1). The reference reflector plate 101 according to the design by the spectral reflectance design apparatus 20 is produced (generated). Referring to FIG. 7, the spectral reflectance design apparatus 20 is configured from a measurement unit 201, a calculation unit 202 and a determination unit 203.

The measurement unit 201 measures a spectral reflectance of plants of different vegetations and supplies measurement values to the calculation unit 202.

The calculation unit 202 calculates, on the basis of the measurement values measured by the measurement unit 201, a spectral reflectance that may possibly become a spectral reflectance (target spectral reflectance) to be had by the reference reflector plate 101 to be produced and supplies the determined spectral reflectance to the determination unit 203.

The determination unit 203 determines a target spectral reflectance on the basis of the spectral reflectance calculated by the calculation unit 202.

Now, a design process of the reference reflector plate 101 to be used in the vegetation inspection apparatus 10 (FIG. 1), which is executed by the spectral reflectance design apparatus 20 of FIG. 7, is described. Here, as the design method of the reference reflector plate 101, three design methods including a first design process to a third design process of a spectral reflectance are described. In particular, the first design process of a spectral reflectance uses an average spectral reflectance of plants of different vegetations as the target spectral reflectance; the second design process of a spectral reflectance uses, as the target spectral reflectance, a spectral reflectance characteristic calculated by multiplying an average spectral reflectance by an adjustment gain according to a minimum reflectance; and the third design process of a spectral reflectance uses, as the target spectral reflectance, a spectral reflectance characteristic calculated by multiplying the average spectral reflectance by an adjustment gain according to a maximum reflectance.

(First Design Process of Spectral Reflectance)

First, the first design process of a spectral reflectance is described with reference to a flow chart of FIG. 8.

At step S11, the measurement unit 201 measures a spectral reflectance characteristic O_PLT_i($\lambda$) of plants of different vegetations. Here, the measurement unit 201 is configured from a spectroscope and a sensing element, and disperses light from the plants of different vegetations using a prism or a diffraction grating and measures (senses) the intensity of the dispersed light for each wavelength by the sensing element. By performing such measurement, the reflectance (spectral reflectance) for each wavelength in a wavelength band in the spectral sensitivity band of the measurement unit 201 is measured.

It is to be noted that i that is a suffix of O_PLT is an index indicative of a number of each of individuals of different characteristics among individuals included in the inspection object 50. Here, the characteristic indicates, for plants of the same type (for example, a turf), a vegetation representative of an amount or activity of the plant. Meanwhile, $\lambda$ signifies a wavelength.

At step S12, the calculation unit 202 calculates an average spectral reflectance O_PLT_AVE($\lambda$) that is an average of a plurality of spectral reflectances O_PLT_i($\lambda$) on the basis of the plurality of measurement values measured by the process at step S11.

At step S13, the determination unit 203 determines the average spectral reflectance O_PLT_AVE($\lambda$) calculated by the process at step S12 as a target spectral reflectance.

Figure 8:
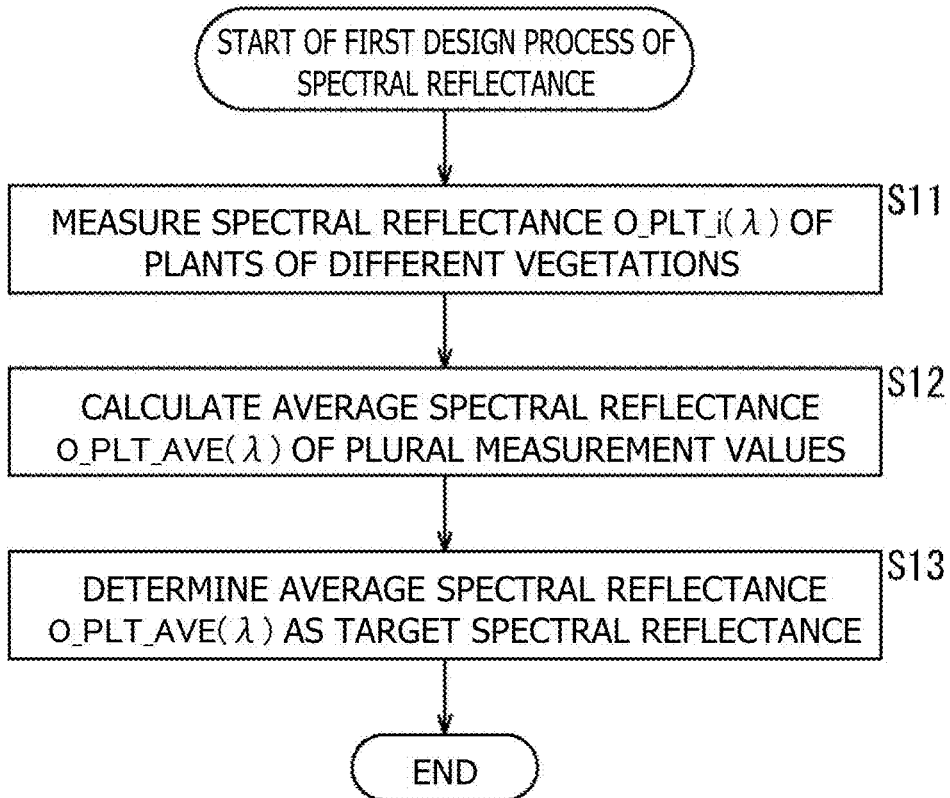
FIG. 8 is a flow chart illustrating a first design process of a spectral reflectance.

When the process at step S13 comes to an end, the first design process of a spectral reflectance of FIG. 8 is ended.

The first design process of a spectral reflectance has been described. In the first design process of a spectral reflectance, an average value of a plurality of spectral reflectances is determined as the target spectral reflectance. Then, a reference reflector plate 101 is produced in accordance with the target spectral reflectance determined in this manner and is used in the vegetation inspection apparatus 10 (FIG. 1).

(Second Design Process of Spectral Reflectance)

Now, the second design process of a spectral reflectance is described with reference to a flow chart of FIG. 9. It is to be noted that, is the description of FIG. 9, graphs of FIGS. 10 to 13 are suitably referred to.

At step S31, the measurement unit 201 measures a spectral reflectance O_PLT_i($\lambda$) of plants of different vegetations similarly to the process at step S11 of FIG. 8. In particular, as depicted in FIG. 10, for example, a plant A, another plant B and a further plant C are plants of the same type (for example, a turf) and are different in vegetation, and different spectral reflectances O_PLT_i($\lambda$) are measured for the individual plants of different vegetations.

Figure 11:
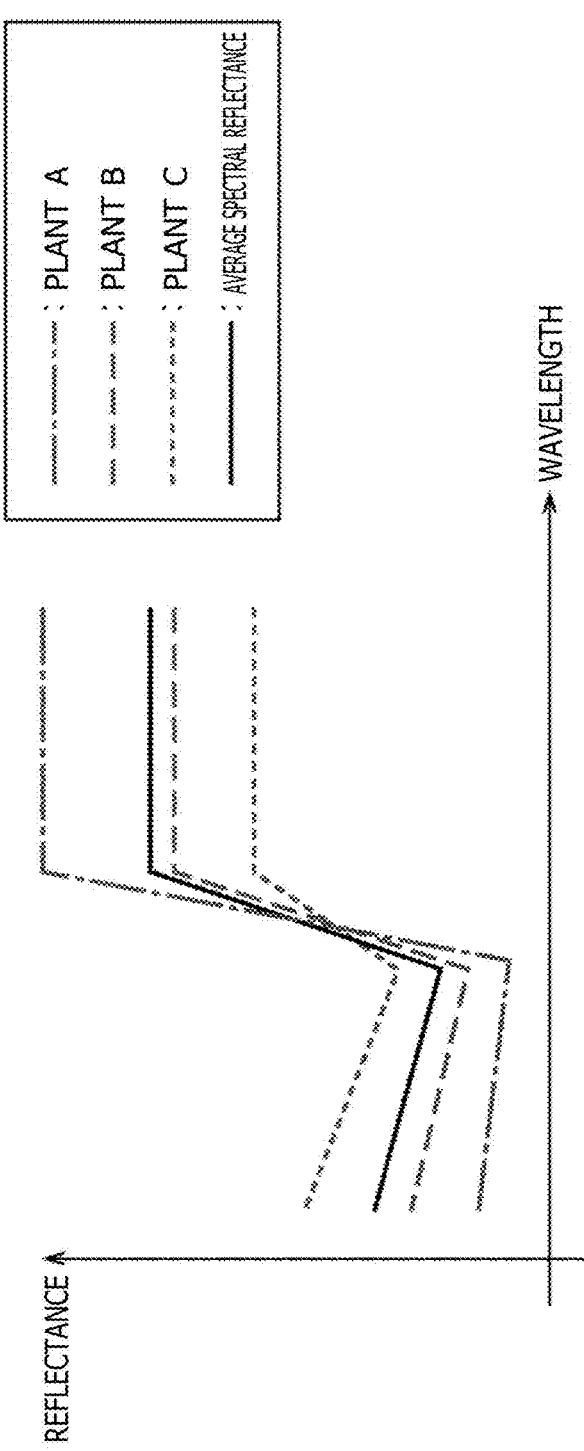
FIG. 11 is a view illustrating calculation of an average spectral reflectance.

At step S32, the calculation unit 202 calculates, on the basis of a plurality of measurement values measured by the process at step S31, an average spectral reflectance O_PLT_AVE($\lambda$) that is an average value of the plurality of spectral reflectances O_PLT_i($\lambda$). In particular, if spectral reflectances O_PLT_i($\lambda$), for example, of plants (plant A, plant B and plant C) of a same type of different vegetations are measured as depicted in FIG. 11, then an average value of the spectral reflectances O_PLT_i($\lambda$) of the plants is determined as an average spectral reflectance O_PLT_AVE ($\lambda$) (solid line graph of FIG. 11).

At step S33, the calculation unit 202 calculates average spectral reflectances PLT_AVE_R and PLT_AVE_IR in each spectral sensitivity band of the R channel and the IR channel with respect to the average spectral reflectance O_PLT_AVE ($\lambda$) calculated by the process at step S32.

At step S34, the calculation unit 202 calculates an average reflectance in each of the spectral sensitivity bands of the R channel and the IR channel in regard to the spectral reflectances O_PLT_i($\lambda$) of the plants (plant A, plant B and plant C) of a same type of different vegetations and searches for minimum reflectances PLT_MIN_R and PLT_MIN_IR.

At step S35, the calculation unit 202 calculates, for each channel, a ratio between the average reflectance (PLT_AVE_R, PLT_AVE_IR) calculated by the process at step S33 and the minimum reflectance (PLT_MIN_R, PLT_MIN_IR) calculated by the process at step S34 in the following description, the ratio between the average reflectance and the minimum reflectance is referred to also as adjustment gain. Here, for each of the R channel and the IR channel, adjustment gains (gain1 and gain2) are calculated by an expression (18) given below.

$$\text{gain1}=\text{PLT\_MIN}\_R/\text{PLT\_AVE}\_R$$

$$\text{gain2}=\text{PLT\_MIN}\_IR/\text{PLT\_AVE}\_IR \quad (18)$$

At step 336, the calculation unit 202 calculates a spectral reflectance characteristic by multiplying the average spectral reflectance O_PLT_AVE($\lambda$) calculated by the process at step S32 by the adjustment gain (gain1, gain2) calculated by the process at step S35 in each of the spectral sensitivity bands of each of the R channel and the IR channel. Then, the determination unit 203 determines the spectral reflectance characteristic determined in this manner as a target spectral reflectance.

Figure 12:
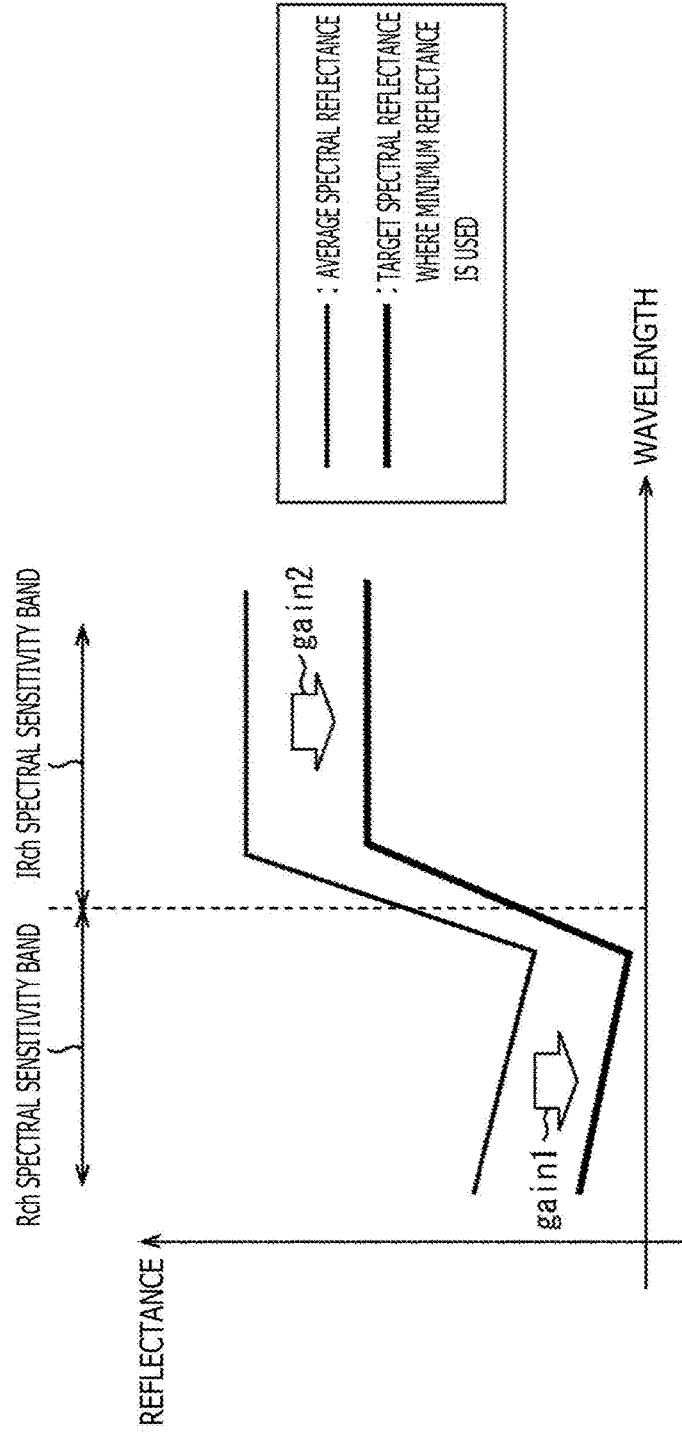
FIG. 12 is a view illustrating adjustment of the spectral reflectance in a spectral sensitivity band of Rch/IRch.

In particular, as depicted in FIG. 12, within the spectral sensitivity band of the R channel, the average spectral reflectance O_PLT_AVE($\lambda$) is multiplied by the adjustment gain (gain1), and within the spectral sensitivity band of the IR channel, the average spectral reflectance O_PLT_AVE($\lambda$) is multiplied by the adjustment gain (gain2) to adjust the average spectral reflectance O_PLT_AVE($\lambda$) in each of the spectral sensitivity bands.

Figure 13:
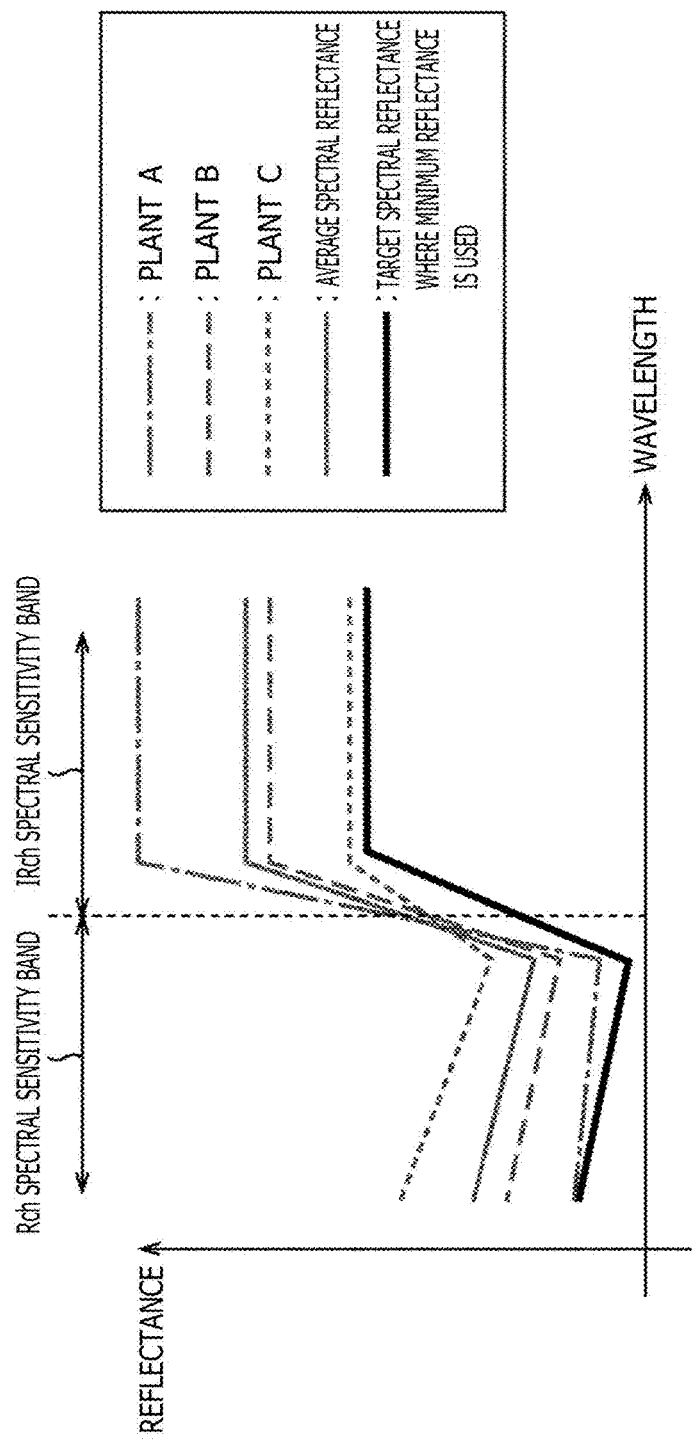
FIG. 13 is a view illustrating determination of a target spectral reflectance where a minimum reflectance is used.

In particular, as depicted in FIG. 13, the average spectral reflectance O_PLT_AVE($\lambda$) determined from the spectral reflectances O_PLT_i($\lambda$) of the plants (plant A, plant B and plant C) of a same type of different vegetations are adjusted with the adjustment gains (gain1, gain2) according to the minimum reflectances (PLT_MIN_R, PLT_MIN_IR), and the spectral reflectance characteristic after the adjustment is determined as a target spectral reflectances (graph of a solid line of FIG. 13).

Figure 9:
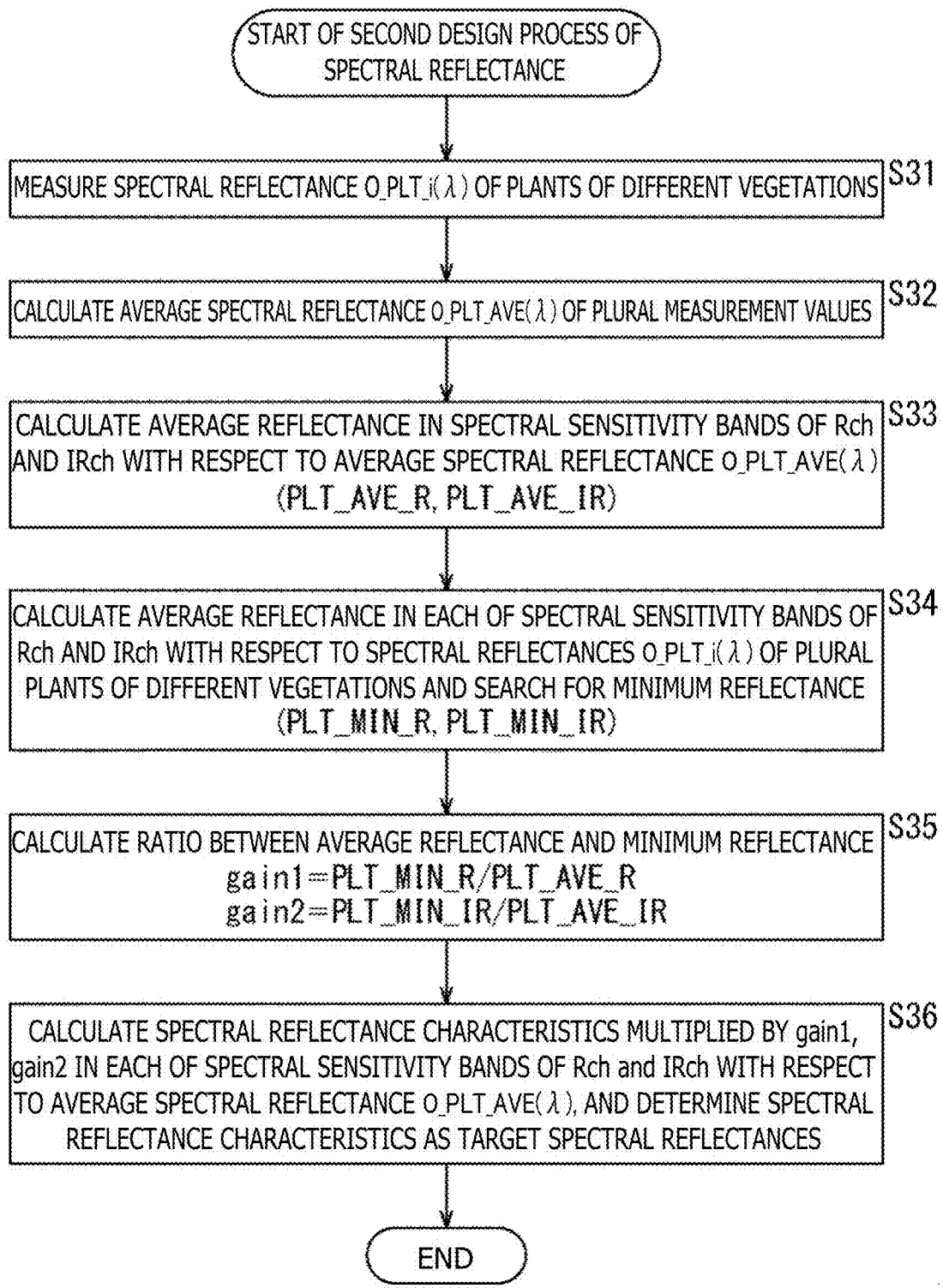
FIG. 9 is a flow chart illustrating a second design process of a spectral reflectance.

When the process at step S36 ends, the second design process of a spectral reflectance of FIG. 9 is ended.

The second design process of a spectral reflectance has been described. In the second design process of a spectral reflectance, a spectral reflectance characteristic calculated by multiplying, for each spectral sensitivity band of each channel (R channel and IR channel), an average spectral reflectance O_PLT_AVE($\lambda$) by an adjustment gain (gain1, gain2) according to a minimum reflectance is determined as a target spectral reflectance. Then, a reference reflector plate 101 according to the target spectral reflectance determined in this manner is produced and used in the vegetation inspection apparatus 10 (FIG. 1).

Incidentally, upon measurement of the inspection object 50 and the reference reflector plate 101 in the first measurement process (FIG. 23) or the second measurement process (FIG. 25) of an inspection index of the inspection object 50 under the measurement light source L1 hereinafter described, preferably the measurement values (R channel value and IR channel value) regarding all objects (for example, various plants or reference reflector plates 101) are included in a dynamic range of the sensor 103, namely, are not saturated with signal charge.

Here, in the second design process of a spectral reflectance, the (spectral reflectance of the) reference reflector plate 101 is designed such that the average spectral reflectance O_PLT_AVE($\lambda$) keeps a minimum value of a characteristic variation of a plant (minimum reflectance). Therefore, if the exposure control object upon measurement of the inspection object 50 and the reference reflector plate 101 described hereinabove is subjected to exposure control in accordance with the inspection object 50 (plant), then at is guaranteed that the measurement value of the reference reflector plate 101 is not saturated without fail, and therefore, it is possible to place the measurement values of all objects (R channel value and IR channel value) into the dynamic range of the sensor 103 (out of saturation).

Further, if, upon exposure control with the exposure control object upon measurement set to the inspection object 50 (plant), exposure control is performed for an inspection object 50 (plant) that indicates a maximum measurement value among the plurality of inspection objects 50 such that the measurement value of the same comes close to a maximum value of the output value of the sensor 103, then underexposure does not occur even with the reference reflector plate 101 or an inspection object 50 (plant) that has a low reflectance, and measurement (sensing) that is good in S/N ratio and makes the most of the dynamic range of the sensor 103 can be achieved.

(Third Design Process of Spectral Reflectance)

Now, the third design process of a spectral reflectance is described with reference to a flow chart of FIG. 14. It is to be noted that, in the description of FIG. 14, graphs of FIGS. 15 to 18 are suitably referred to.

At step S51, the measurement unit 201 measures the spectral reflectance O_PLT_i($\lambda$) of plants of different vegetations similarly to the process at step S11 of FIG. 8. In particular, as depicted in FIG. 15, for example, a plant A, another plant B and a further plant C are plants of a same type (for example, a turf) and are different in vegetation, and different spectral reflectances O_PLT_i($\lambda$) are measured for the individual plants of different vegetations.

Figure 16:
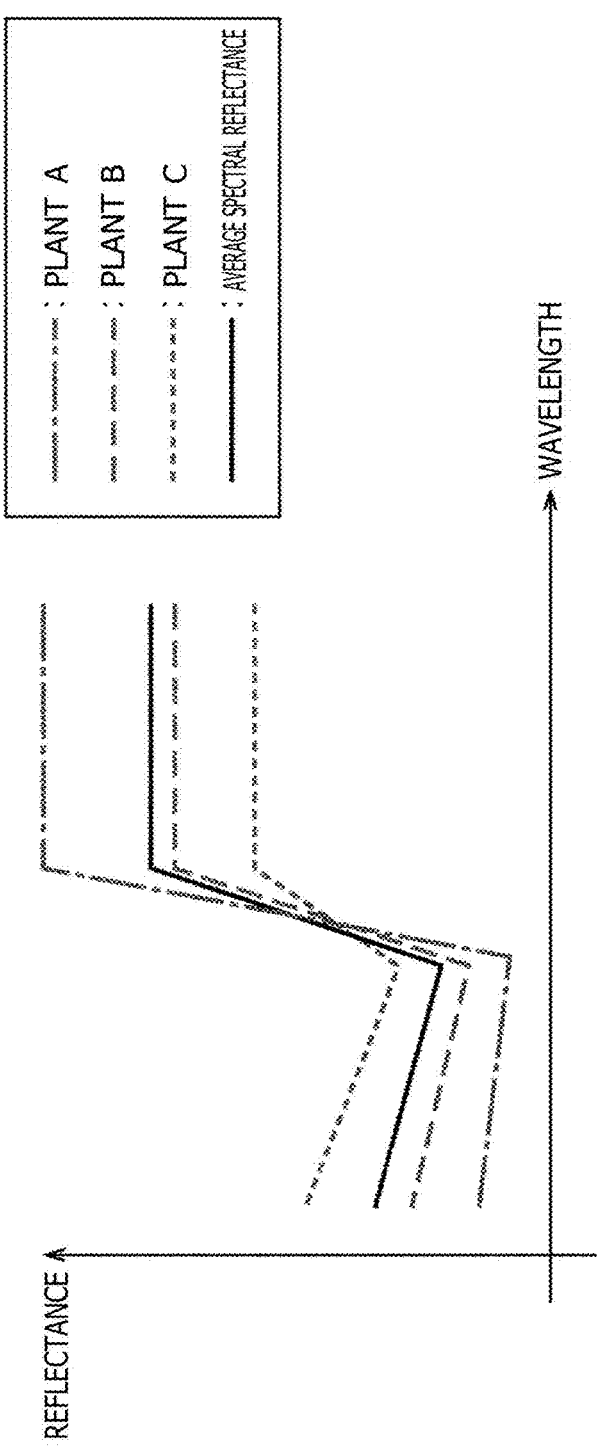
FIG. 16 is a view illustrating calculation of an average spectral reflectance.

At step S52, the calculation unit 202 calculates, on the basis of a plurality of measurement values measured by the process at step S51, an average spectral reflectance O_PLT_AVE($\lambda$) that is an average value of the plurality of spectral reflectances O_PLT_i($\lambda$). In particular, if spectral reflectances O_PLT_i($\lambda$), for example, of plants (plant A, plant B and plant C) of a same type of different vegetations are measured as depicted in FIG. 16, then an average value of the spectral reflectances O_PLT_i($\lambda$) of the plants is determined as an average spectral reflectance O_PLT_AVE ($\lambda$) (solid line graph of FIG. 16).

At step S53, the calculation unit 202 calculates average spectral reflectance PLT_AVE_R and PLT_AVE_IR in each spectral sensitivity band of the R channel and the IR channel with respect to the average spectral reflectance O_PLT_AVE ($\lambda$) calculated by the process at step S52.

At step S54, the calculation unit 202 calculates an average reflectance in each of the spectral sensitivity bands of the R channel and the IR channel in regard to the spectral reflectances O_PLT_i($\lambda$) of the plants (plant A, plant B and plant C) of a same type of different vegetations and searches for maximum reflectances PLT_MAX_R and PLT_MAX_IR.

At step S55, the calculation unit 202 calculates, for each channel, a ratio between the average reflectance (PLT_AVE_R, PLT_AVE_IR) calculated by the process at step S53 and the maximum reflectance (PLT_MAX_R, PLT_MAX_IR) calculated by the process at step S54. In the following description, also the ratio between the average reflectance and the maximum reflectance is referred to as adjustment gain. Here, for each of the R channel and the IR channel, adjustment gains (gain3, gain4) are calculated by an expression (19) given below.

$$\text{gain3} = \text{PLT\_MAX}\_R / \text{PLT\_AVE}\_R$$

$$\text{gain4} = \text{PLT\_MAX}\_{IR} / \text{PLT\_AVE}\_{IR} \quad (19)$$

At step S56, the calculation unit 202 calculates a spectral reflectance characteristic by multiplying the average spectral reflectance O_PLT_AVE($\lambda$) calculated by the process at step S52 by the adjustment gain (gain3, gain4) calculated by the process at step S55 in each of the spectral sensitivity bands of each of the R channel and the IR channel. Then, the determination unit 203 determines the spectral reflectance characteristic determined in this manner as a target spectral reflectance.

Figure 17:
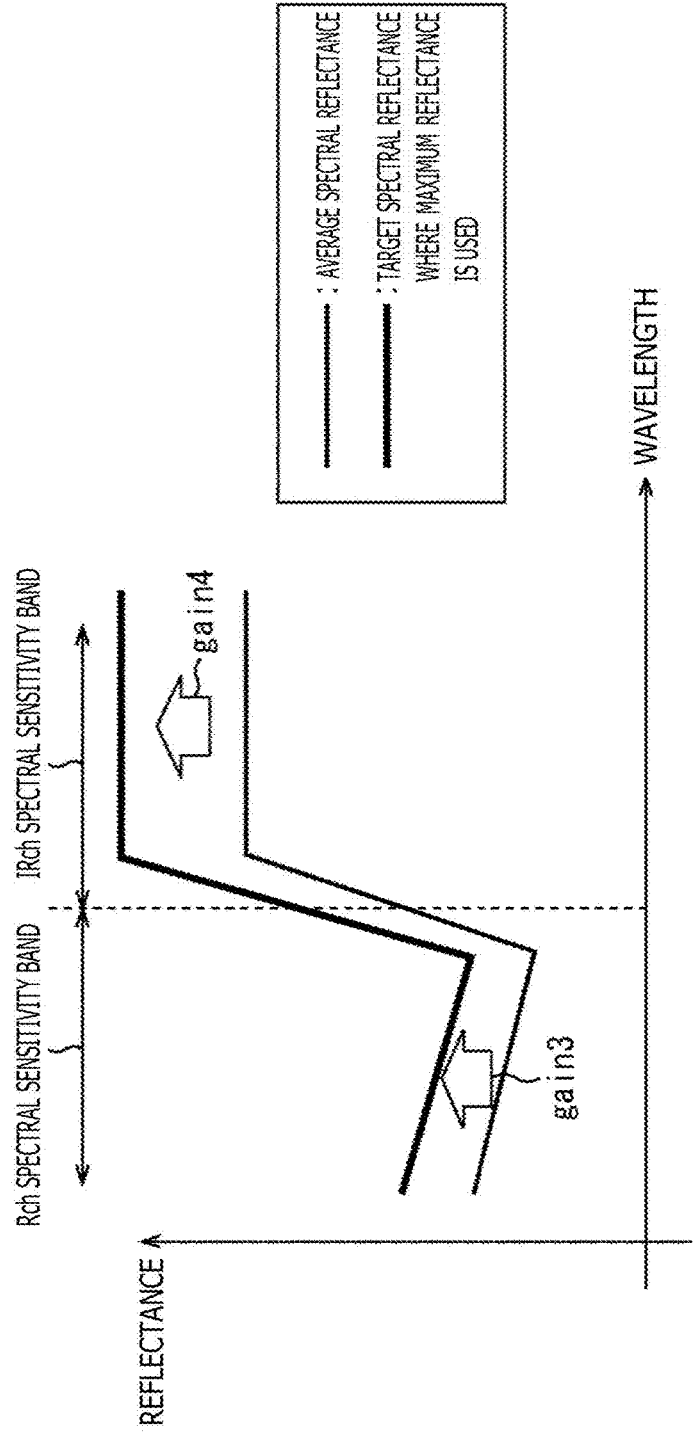
FIG. 17 is a view illustrating adjustment of the spectral reflectance in a spectral sensitivity band of Rch/IRch.

In particular, as depicted in FIG. 17, within the spectral sensitivity band of the R channel, the average spectral reflectance O_PLT_AVE($\lambda$) is multiplied by the adjustment gain (gain3), and within the spectral sensitivity band of the IR channel, the average spectral reflectance O_PLT_AVE($\lambda$) is multiplied by the adjustment gain (gain4) to adjust the average spectral reflectance O_PLT_AVE($\lambda$) in each of the spectral sensitivity bands.

Figure 18:
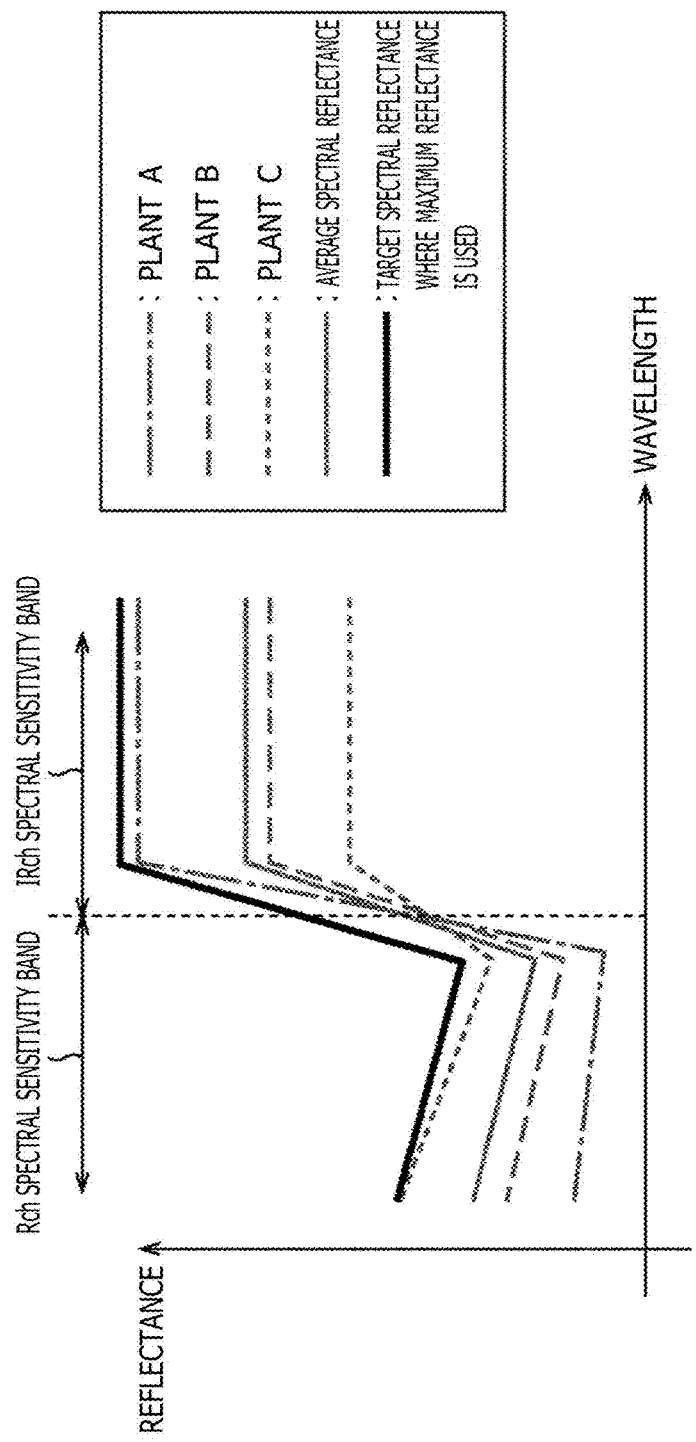
FIG. 18 is a view illustrating determination of target spectral reflectance where a maximum reflectance is used.

In particular, as depicted in FIG. 18, the average spectral reflectance O_PLT_AVE($\lambda$) determined from the spectral reflectances O_PLT_i($\lambda$) of the plants (plant A, plant B and lint C) of a same type of different vegetations are adjusted with the adjustment gains (gain3, gain4) according to the maximum reflectances (PLT_MAX_R, PLT_MAX_IR), and the spectral reflectance characteristic after the adjustment is determined as a target spectral reflectances (graph of a solid line of FIG. 18).

Figure 14:
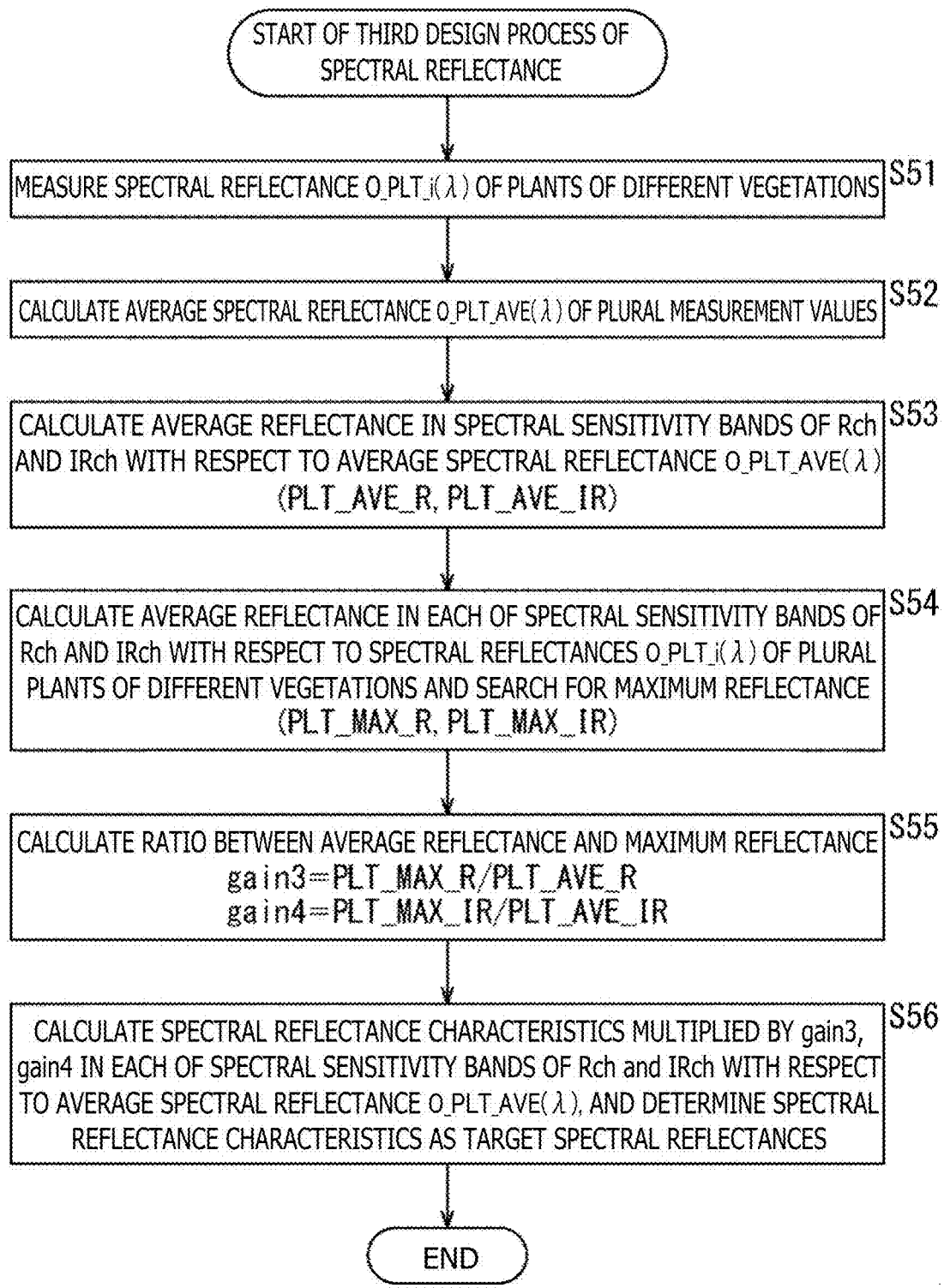
FIG. 14 is a flow chart illustrating a third design process of a spectral reflectance.

When the process at step S56 comes to an end, the third design process of a spectral reflectance of FIG. 14 is ended.

The third design process of a spectral reflectance has been described. In the third design process of a spectral reflectance, a spectral reflectance characteristic calculated by multiplying, for each spectral sensitivity band of each channel (R channel and IR channel), an average spectral reflectance O_PLT_AVE($\lambda$) by an adjustment gain (gain3, gain4) according to a maximum reflectance is determined as a target spectral reflectance. Then, a reference reflector plate 101 according to the target spectral reflectance determined in this manner is produced and used in the vegetation inspection apparatus 10 (FIG. 1).

Incidentally, upon measurement of the inspection object 50 and the reference reflector plate 101 in the first measurement process (FIG. 23) or the second measurement process (FIG. 25) of an inspection index of the inspection object 50 under the measurement light source L1 hereinafter described, preferably the measurement values (R channel value and IR channel value) regarding all objects (for example, various plants or reference reflector plates 101) are included in a dynamic range of the sensor 103, namely, are not saturated with signal charge.

Here, in the third design process of a spectral reflectance, (the spectral reflectance of) the reference reflector plate 101 is designed such that the average spectral reflectance O_PLT_AVE($\lambda$) keeps a maximum value in characteristic variation of a plant (maximum reflectance). Therefore, if the exposure control object upon measurement of the inspection object 50 and the reference reflector plate 101 described hereinabove is subjected to exposure control in accordance with the reference reflector plate 101, then it is guaranteed that the measurement value of the inspection object 50 (plant) is not saturated without fail, and therefore, it is possible to place the measurement values of all objects (R channel value and IR channel value) into the dynamic range of the sensor 103 (out of saturation).

Further, if, upon exposure control with the exposure control object upon measurement set to the reference reflector plate 101, exposure control is performed such that the measurement value of the reference reflector plate 101 becomes close to the maximum value of the output value of the sensor 103, then underexposure does not occur even with an inspection object 50 plant) that has a low reflectance, and measurement (sensing) that is good in S/N ratio and makes the most of the dynamic range of the sensor 103 can be achieved.

It is to be noted that the first design process to the third design process of a spectral reflectance described above are an example of a design method for designing the spectral reflectance of the reference reflector plate 101 to be used by the vegetation inspection apparatus 10 (FIG. 1), and a different design method may be adopted if it is a method by which (the spectral reflectance of) the reference reflector plate 101 having a characteristic according the spectral reflectance of the inspection object 50 such as a plant can be designed.

<4. Inspection of Inspection Object>

Now, an inspection method of the inspection object 50 performed by the vegetation inspection apparatus 10 (FIG. 1) that uses the reference reflector plate 101 produced in accordance with the design method described above is described. Here, for example, after the vegetation inspection apparatus 10 performs measurement of the reference reflector plate 101 under the reference light source L0, it performs measurement of an inspection index (NDVI value) of the inspection object 50 under the measurement light source L1. According, measurement of the reference reflector plate 101 under the reference light source L0 and measurement of the inspection index of the inspection object 50 under the measurement light source L1 are described in order.

(1) Measurement of Reference Reflector Plate Under Reference Light Source (Functional Configuration of Vegetation Inspection Apparatus Upon Measurement of Reference Reflector Plate Under Reference Light Source)

Figure 19:
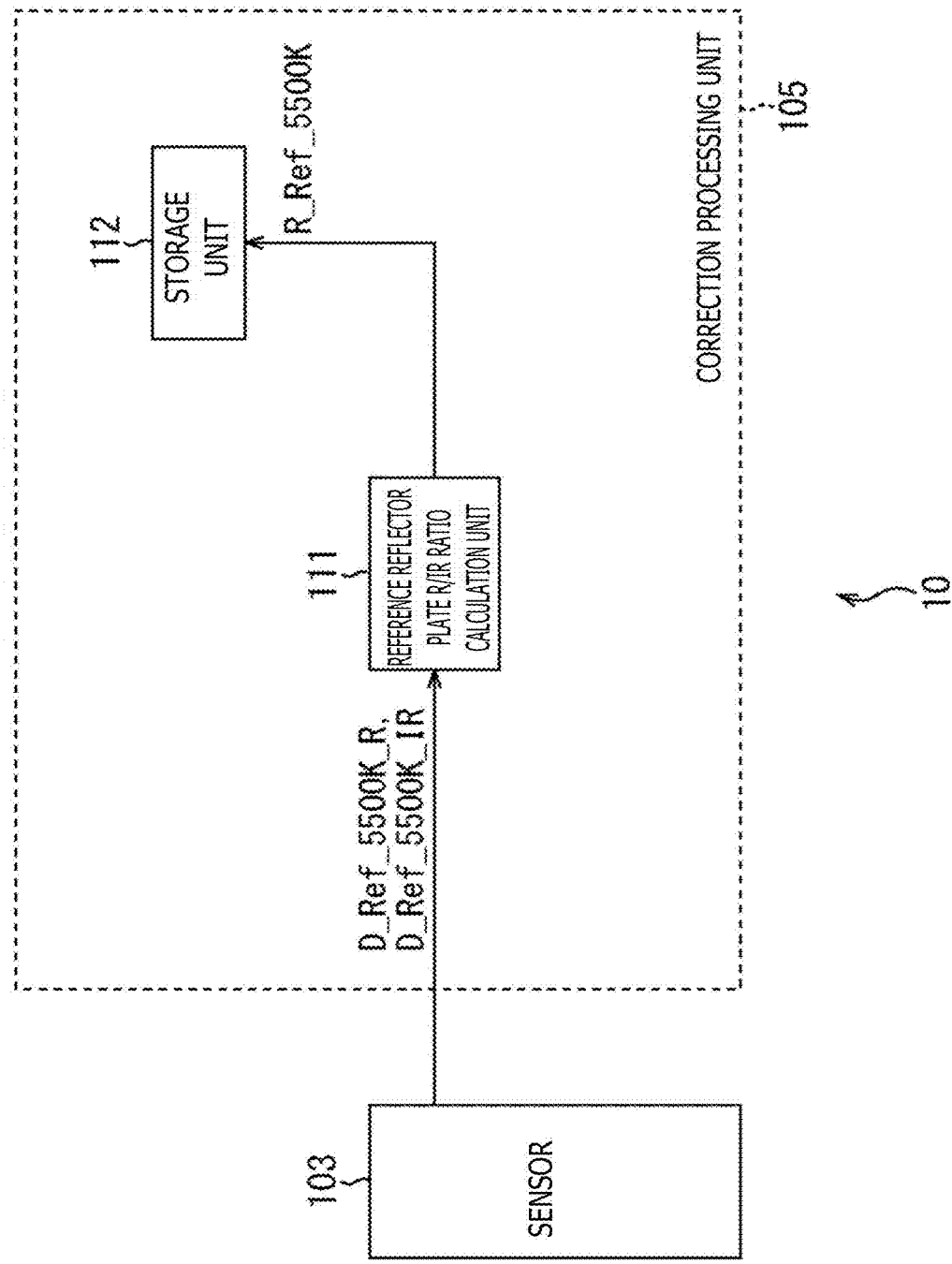
FIG. 19 is a view depicting a functional configuration of the vegetation inspection apparatus upon measurement of the reference reflector plate.

FIG. 19 is a view depicting a functional configuration of the vegetation inspection apparatus 10 (FIG. 1) upon measurement of the reference reflector plate 101 under the reference light source L0.

It is to be noted that, in FIG. 19, from among the blocks configuring the vegetation inspection apparatus 10 (FIG. 1), only the sensor 103 and the correction processing unit 105 are depicted which are blocks that specifically relate upon measurement of the reference reflector plate 101 under the reference light source L0. Further, in the following description, a case in which a light source of a color temperature of 5500K as an example of the reference light source L0 is used is described.

The sensor 103 measures the R channel value (D_Ref_5500K_R) and the IR channel value (D_Ref_5500K_IR) according to reflection light from the reference reflector plate 101 under the reference light source L0 (for example, a light source of a color temperature of 5500K) and supplies measured values to the correction processing unit 105. It is to be noted here that the R channel value and the IR channel value are outputted, for example, data of a two-dimensional array structure.

When measurement of the reference reflector plate 101 under the reference light source L0 is performed, the correction processing unit 105 calculates the reference spectral ratio (R/IR ratio) of the reference reflector plate 101 under the reference light source L0 (for example, a light source of a color temperature of 5500K) and stores a resulting value. In FIG. 19, the correction processing unit 105 is configured from a reference reflector plate R/IR ratio calculation unit 111 and a storage unit 112.

The reference reflector plate R/IR ratio calculation unit 111 uses the R channel value (D_Ref_5500K_R) and the IR channel value (D_Ref_5500K_IR) supplied thereto from the sensor 103 to calculate a reference spectral ratio (R_Ref_5500K). The reference reflector plate R/IR ratio calculation unit 111 stores information indicative of the calculated reference spectral ratio (R_Ref_5500K) into the storage unit 112.

In this manner, upon measurement of the reference reflector plate 101 under the reference light source L0, the vegetation inspection apparatus 10 calculates a reference spectral ratio (R/IR ratio) of the reference reflector plate 101 under the reference light source L0 (for example, a light source of a color temperature of 5500K) and stores the calculated reference spectral ratio (R/IR ratio) into the storage unit 112 in advance.

(Measurement Process of Reference Reflector Plate Under Reference Light Source)

Now, a measurement process of the reference reflector plate 101 under the reference light source L0 executed by the vegetation inspection apparatus 10 of FIG. 19 is described with reference to a flow chart of FIG. 20. It is to be noted that the measurement process of the reference reflector plate 101 of FIG. 20 is executed preceding to the first measurement process (FIG. 23) or the second measurement process (FIG. 25) of an inspection index of the inspection object. 50 under the measurement light source L1.

Figure 20:
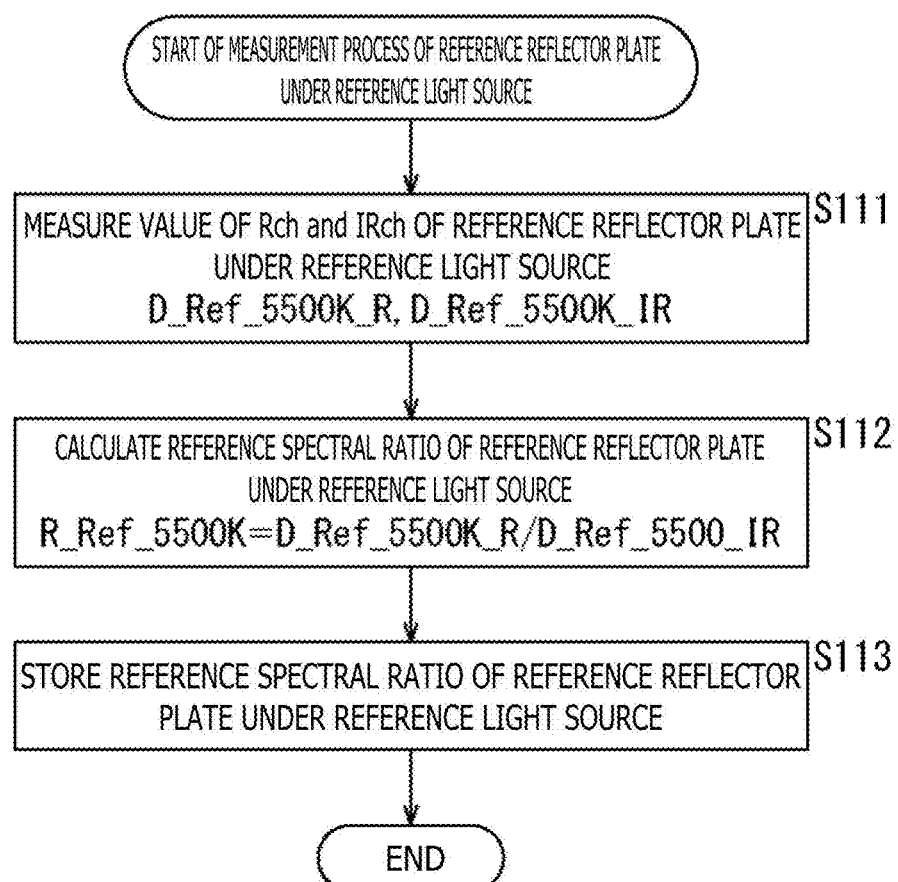
FIG. 20 is a flow chart illustrating a measurement process of the reference reflector plate under a reference light source.
Figure 21:
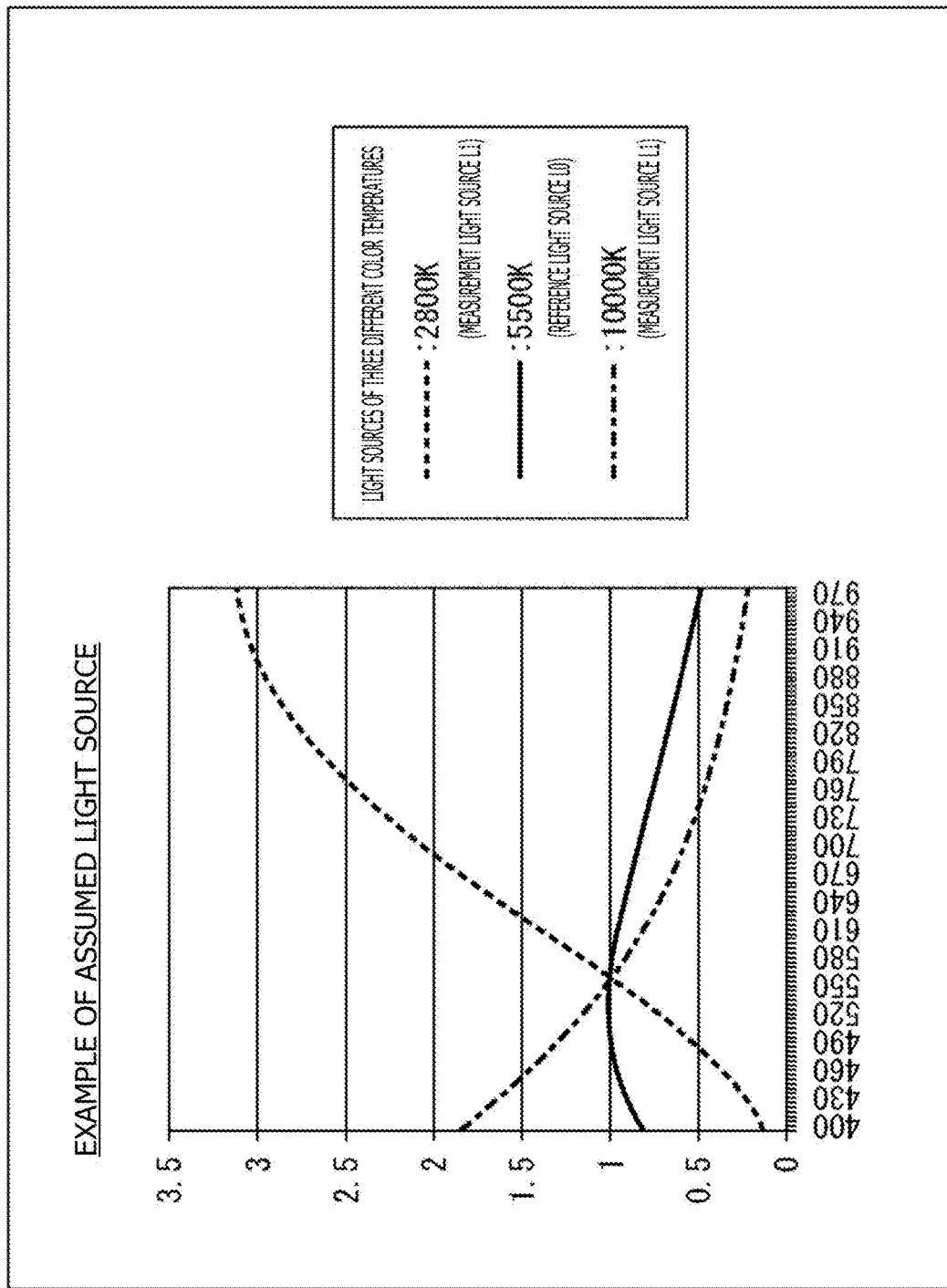
FIG. 21 is a view depicting an example of as assumed light source.

Here, the reference light source L0 is determined before processing of the flow chart of FIG. 20 is executed. Here, for example, a light source of a color temperature of 5500K is determined as the reference light source L0 by a user or in accordance with a value prescribed in advance. For example, a light source of the color temperature of 5500K is determined as the reference light source L0 from among light sources of color temperatures of different characteristics of 2800K, 5500K, 10000K and so forth as depicted in FIG. 21. It is to be noted that, in this case, the light source of the color temperature of 2800K and the light source of the color temperature of 10000K can be used as the measurement light source L1.

Referring back to FIG. 20, at step S111, the sensor 103 measures (senses) the R channel value (R_Ref_5500K_R) and the IR channel value (R_Ref_5500K_IR) the reference reflector plate 101 under the reference light source L0 determined in advance (for example, the light source of the color temperature of 5500K).

At step S112, the reference reflector plate R/IR ratio calculation unit 111 arithmetically operates an expression (20) given below on the basis of the R channel value (R_Ref_5500K_R) and the IR channel value (D_Ref_5500K_IR) measured by the process at step S111 to calculate a reference spectral ratio (R_Ref_5500K) of the reference reflector plate 101 under the reference light source L0 (for example, a light source of the color temperature of 5500K).

$$R\_Ref\_5500K = D\_Ref\_5500K\_R/D\_Ref\_5500K\_IR \quad (20)$$

At step S113, the reference reflector plate R/IR ratio calculation unit 111 stores information indicative of the reference spectral ratio (R_Ref_5500K) calculated by the process at step S112 into the storage unit 112.

The measurement process of the reference reflector plate 101 under the reference light source L0 has been described. In the measurement process of the reference reflector plate 101, the reference spectral ratio (R/IR ratio) of the reference reflector plate 101 under the reference light source L0 (for example, a light source of a color temperature of 5500K) is calculated and stored into the storage unit 112.

(2) Measurement of Inspection Index of Inspection Object Under Measurement Sight Source Now, measurement of an inspection index of the inspection object 50 under the measurement light source L1 is described. Here, a configuration and a process (FIGS. 22 and 23) in the case in which, when an arithmetic operation for calculating an NDVI value is executed, normalization of values to be used in the arithmetic operation is not performed are described first, and then also a configuration and a process (FIGS. 24 and 25) where normalization of values to be used in the arithmetic operation is performed are described.

(First Functional Configuration of Vegetation Inspection Apparatus Upon Inspection Index Measurement Under Measurement Light Source)

Figure 22:
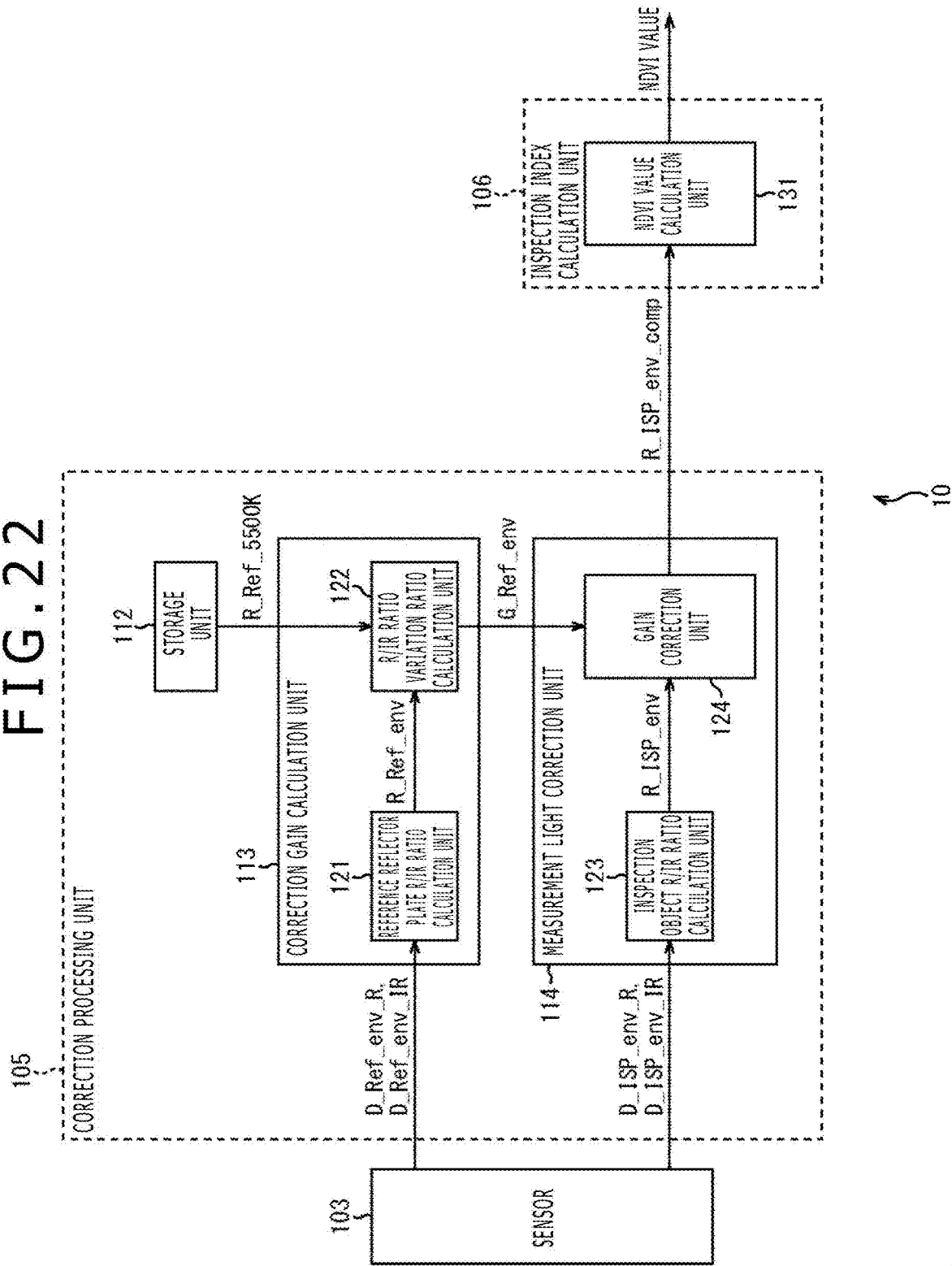
FIG. 22 is a view depicting as example of a first functional configuration of the vegetation inspection apparatus upon measurement of an inspection index.

FIG. 22 is a view depicting a first functional configuration of the vegetation inspection apparatus 10 (FIG. 1) upon measurement of an inspection index (NDVI value) of the inspection object 50 under the measurement light source L1.

It is to be noted that, in FIG. 22, from among blocks that configure the vegetation inspection apparatus 10 (FIG. 1), only the sensor 103, correction processing unit 105 and inspection index calculation unit 106 that are blocks that specifically relate to measurement of an inspection index of the inspection object 50 under the measurement light source L1 are depicted.

The sensor 103 measures an R channel value (D_Ref_env_R) and an IR channel value (D_Ref_env_IR) according to reflection light from the reference reflector plate 101 under the measurement light source L1 (for example, a light source of the color temperature of 2800K or 10000K) and supplies measured values to the correction processing unit 105. Further, the sensor 103 measures an R channel value (D_ISV_env_R) and an IR channel value (D_ISV_env_IR) according to reflection light from the inspection object 50 under the measurement light source L1 and supplies the measured channel values to the correction processing unit 105. It is to be noted here that the R channel value and the IR channel value are outputted, for example, as data of a two-dimensional array structure.

Meanwhile, although each value supplied from the sensor 103 is a value of each pixel unit at a predetermining sensing timing, not a value of each pixel unit but an average value among a plurality of pixels may be supplied or a value obtained by integrating output values in a time direction including a predetermined timing may be supplied. Further, the vegetation inspection apparatus 10 may calculate an average value of a plurality of pixels or an integrated value of output values in a time direction including a predetermined timing on the basis of data supplied thereto from the sensor and use the value in a correction process.

When measurement of an inspection index of the inspection object 50 under the measurement light source L1 is performed, the correction processing unit 105 calculates a correction gain of the spectral ratio on the basis of the reference spectral ratio (R/IR ratio) of the reference reflector plate 101 under the reference light source L0 and the measurement spectral ratio (R/IR ratio) of the reference reflector plate 101 under the measurement light source L1 and uses this correction gain to correct the measurement spectral ratio (R/IR ratio) of the inspection object 50 under the measurement light source L1.

The correction processing unit 105 is configured from a storage unit 112, a correction gain calculation unit 113 and a measurement light correction unit 114. It is to be noted that, in the storage unit 112, information indicative of the reference spectral ratio (R_Ref_5500K) of the reference reflector plate 101 under the reference light source L0 is stored in advance by a measurement process (FIG. 20) of a reference reflector plate under the reference light source L0.

The correction gain calculation unit 113 calculates a correction gain of the spectral ratio. The correction gain calculation unit 113 is configured from a reference reflector plate R/IR ratio calculation unit 121 and an R/IR ratio variation ratio calculation unit 122.

The reference reflector plate R/IR ratio calculation unit 121 calculates a measurement spectral ratio (R_Ref_env) of the reference reflector plate 101 under the measurement light source L1 using the R channel value (D_ISV_env_R) and the IR channel value (D_ISV_env_IR) supplied from the sensor 103 and supplies the measurement spectral ratio (R_Ref_env) to the R/IR ratio variation ratio calculation unit 122.

The R/IR ratio variation ratio calculation unit 122 reads out information indicative of the reference spectral ratio (R_Ref_5500K) stored in the storage unit 112. The R/IR ratio variation ratio calculation unit 122 calculates a correction gain (G_Ref_env) of the spectral ratio on the basis of the measurement spectral ratio (R_Ref_env) (of the reference reflector plate 101 under the measurement light source L1) supplied from the reference reflector plate R/IR ratio calculation unit 121 and the reference spectral ratio (R_Ref_5500K) (of the reference reflector plate 101 under the reference light source L0) read out from the storage unit 112, and supplies the calculated correction gain (G_Ref_env) to the measurement light correction unit 114.

The measurement light correction unit 114 uses the correction gain of the spectral ratio to correct the measurement spectral ratio (R/IR ratio) of the inspection object 50 under the measurement light source L1. The measurement light correction unit 114 is configured from an inspection object R/IR ratio calculation unit 123 and a gain correction unit 124.

The inspection object R/IR ratio calculation unit 123 calculates a measurement spectral ratio (R_ISP_env) of the inspection object 50 under the measurement light source L1 using the R channel value (D_ISP_env_R) and the IR channel value (R_ISP_env) supplied thereto from the sensor 103, and supplies the measurement spectral ratio (R_ISP_env) to the gain correction unit 124.

To the gain correction unit 124, a correction gain (G_Ref_env) from (the R/IR ratio variation ratio calculation unit 122 of) the correction gain calculation unit 113 is supplied. The gain correction unit 124 corrects the measurement spectral ratio (R_ISP_env) of the inspection object 50 under the measurement light source L1 supplied thereto from the inspection object R/IR ratio calculation unit 123 on the basis of the correction gain (G_Ref_enb) supplied from the R/IR ratio variation ratio calculation unit 122 and supplies the measurement spectral ratio (R_ISP_env_comp) after corrected to the inspection index calculation unit 106.

The inspection index calculation unit 106 calculates an inspection index (NDVI value) of the inspection object 50 using the measurement spectral ratio (of the inspection object 50 under the measurement light source L1) after corrected. The inspection index calculation unit 106 is configured from an NDVI value calculation unit 131.

The NDVI value calculation unit 131 calculates a normalized vegetation index (NDVI value) as the inspection index of the inspection object 50 on the basis of the measurement spectral ratio (R_ISP_env_comp) (of the inspection object 50 under the measurement light source L1) after corrected supplied from (the gain correction unit 124 of the measurement light correction unit 114 of) the correction processing unit 105, and outputs the normalized vegetation index (NDVI value).

As described above, the vegetation inspection apparatus 10 calculates a correction gain according to the spectral ratio (R/IR ratio) of the reference reflector plate 101 under the reference light source L0 and the measurement light source L1 upon measurement of the inspection index (NDVI value) of the inspection object 50 under the measurement light source L1, corrects the spectral ratio (R/IR ratio) of the inspection object 50 under the measurement light source L1 in response to the correction gain and calculates the inspection index (NDVI value) from the spectral ratio (R/IR ratio) after corrected.

It is to be noted that, since the foregoing description indicates a case in which the vegetation inspection apparatus 10 calculates the reference spectral ratio (R_Ref_5500K), the reference reflector plate R/IR ratio calculation unit 121 of FIG. 22 can be made the same block as the reference reflector plate R/IR ratio calculation unit 111 of FIG. 19. However, an apparatus different from the vegetation inspection apparatus 10 may calculate the reference spectral ratio (R_Ref_5500K), and in this case, the different apparatus provides the reference spectral ratio calculated by measurement of the reference reflector plate 101 under the reference light source L0 to the vegetation inspection apparatus 10. Then, the vegetation inspection apparatus 10 stores the reference spectral ratio supplied from the different apparatus and utilizes the reference spectral ratio upon measurement.

(First Measurement Process of Inspection Index)

A first measurement process of an inspection index of the inspection object 50 under the measurement light source L1, which is executed by the vegetation inspection apparatus 10 of FIG. 22, is described with reference to a flow chart of FIG. 23. It is to be noted that this first measurement process of an inspection index is executed after the measurement process of the reference reflector plate 101 under the reference light source L0 (FIG. 20) is performed.

At step S131, the exposure controlling unit 104 (FIG. 1) determines exposure such that none of the reference reflector plate 101 and the inspection object 50 may be saturated under the measurement light source L1.

This exposure control is executed such that measurement (sensing) is performed in a state in which all of four values including the R channel value and the IR channel value of the reference reflector plate 101 and the R channel value and the IR channel value of the inspection object 50 remain within the dynamic range without being saturated as sensor output values from the sensor 103.

In particular, an exposure value is determined, for example, by changing one or plural ones of the shutter speed of an electronic shutter of the sensor 103, the shutter speed of the optical system such as the lens 102 and so forth and an aperture amount by an iris (aperture). This determination of an exposure amount may be controlled automatically by the vegetation inspection apparatus 10 or may be performed manually by a measuring person.

At step S132, the sensor 103 measures the R channel value (D_ISV_env_R) and the IR channel value (D_ISV_env_IR) of the reference reflector plate 101 under the measurement light source L1.

At step S133, the reference reflector plate R/IR ratio calculation unit 121 arithmetically operates an expression (21) given below on the basis of the R channel value (D_ISV_env_R) and the IR channel value (D_ISV_env_IR) measured by the process at step S132 to calculate a measurement spectral ratio (R_Ref_env) of the reference reflector plate 101 under the measurement light source L1.

$$R\_Ref\_env = D\_Ref\_env\_R / D\_Ref\_env\_IR \qquad (21)$$

At step S134, the R/IR ratio variation ratio calculation unit 122 calculates a correction gain (G_Ref_env) of the spectral ratio for correcting the measurement spectrum (R/IR ratio) of the inspection object 50.

In particular, the R/IR ratio variation ratio calculation unit 122 reads out information indicative of the reference spectral ratio (R_Ref_5500K) of the reference reflector plate 101 under the reference light source L0 stored in advance in the storage unit 112 by the measurement process (FIG. 20) of the reference reflector plate under the reference light source 10. Then, the R/IR ratio variation ratio calculation unit 122 uses the reference spectral ratio (R_Ref_5500K) read out from the storage unit 112 to arithmetically operate an expression (22) given below to calculate a correction gain (G_Ref_env) of the spectral ratio.

$$G\_Ref\_env = R\_Ref\_5500K / R\_Ref\_env \qquad (22)$$

At step S135, the sensor 103 and so forth measure the R channel value (D_ISP_env_R) and the IR channel value (D_ISP_env_IR) of the inspection object 50 under the measurement light source L1.

Figure 23:
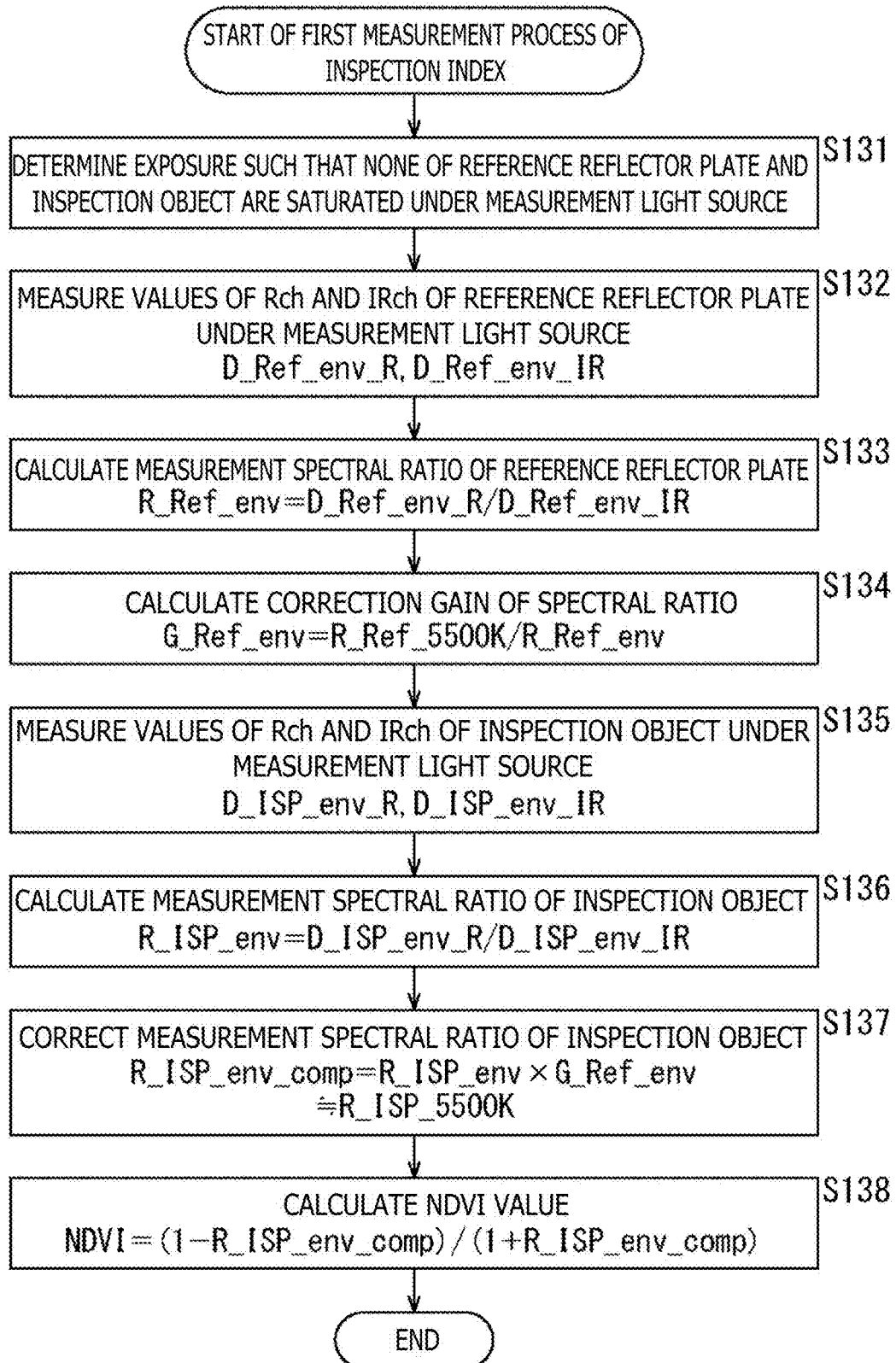
FIG. 23 is a flow chart illustrating a first measurement process of an inspection index.

It is to be noted that, while FIG. 23 indicates a flow of such processing that the vegetation inspection apparatus 10 measures the reference reflector plate 101 under the measurement light source L1 in the process at step S132 and then measures the inspection object 50 under the measurement light source L1 in the process at step S135, where the reference reflector plate 101 and the inspection object 50 are measured at the same time, the process at step S135 is performed at a timing same as that of the process at step S132. In particular, the vegetation inspection apparatus 10 may perform the measurement processes at step S132 and step S135 simultaneously or at different timings. It is to be noted that the measurement processes at step S132 and step S135 are performed at timings before the measurement results are required by the calculation processes at steps S133, S134, S136 and so forth.

At step S136, the inspection object R/IR ratio calculation unit 123 arithmetically operates an expression (23) given below on the basis of the R channel value (D_ISV_env_R) and the IR channel value (D_ISV_env_IR) measured by the process at step S135 to calculate the measurement spectral ratio (R_ISP_env) of the inspection object 50 under the measurement light source L1.

$$R\_ISP\_env = D\_ISP\_env\_R / D\_ISP\_env\_IR \qquad (23)$$

At step S137, the gain correction unit 124 arithmetically operates an expression (24) given below using the correction gain (G_Ref_env) calculated by the process at step S134 to correct the measurement spectral ratio (R_ISP_env) of the inspection object 50 under the measurement light source L1 calculated by the process at step S136.

$$R\_ISP\_env\_comp = R\_ISP\_env \times G\_Ref\_env \qquad (24)$$

It is to be noted that R_ISP_env_comp determined by arithmetically operating the expression (24) becomes equal (becomes substantially equal) to the spectral ratio (R_Ref_5500K) of the inspection object 50 under the reference light source L0.

At step S138, the NDVI value calculation unit 131 arithmetically operates an expression (25) given below using the measurement spectral ratio (R_ISP_env_comp) of the inspection object 50 corrected by the process at step S137 to calculate a normalized vegetation index (NDVI value) as the inspection index of the inspection object 50.

$$NDVI = (1 - R\_ISP\_env\_comp) / (1 + R\_ISP\_env\_comp) \qquad (25)$$

The first measurement process of an inspection index of the inspection object 50 under the measurement light source L1 has been described. In the first measurement process of an inspection index, a correction gain (G_Ref_env) according to the spectral ratio (R_Ref_5500K, R_Ref_env) of the reference reflector plate 101 under the reference light source L0 and the measurement light source L1 is calculated, and the spectral ratio (R_ISP_env) of the inspection object 50 under the measurement light source L1 is corrected using the correction gain (G_Ref_env), whereafter the inspection index (NDVI value) of the inspection object 50 is calculated using the spectral ratio (R_ISP_env_comp) after corrected.

Consequently, even if the measurement light source L1 varies upon measurement of the inspection index of the inspection object 50 under the measurement light source L1, since the spectral ratio (R_ISP_env) of the inspection object 50 under the measurement light source L1 is corrected (measurement light correction) with the correction gain (G_Ref_env) of the spectral ratio such that the spectral ratio (R_ISP_env) becomes equivalent (equal in value) to the spectral ratio (R_Ref_5500K) of the inspection object 50 under the reference light source L0, the light source dependency can be removed (excluded) favorably. As a result, accurate measurement light correction can be performed. For example, even when the light source varies in response to a variation of the weather such as, for example, a fine weather, a cloudy weather or a rainy weather, from a same inspection object 50 (for example, a plant such as a turf), an inspection index (NDVI value) of an equal value is measured.

(Second Functional Configuration of Vegetation Inspection Apparatus Upon Measurement of Inspection Index Under Measurement Light Source)

Figure 24:
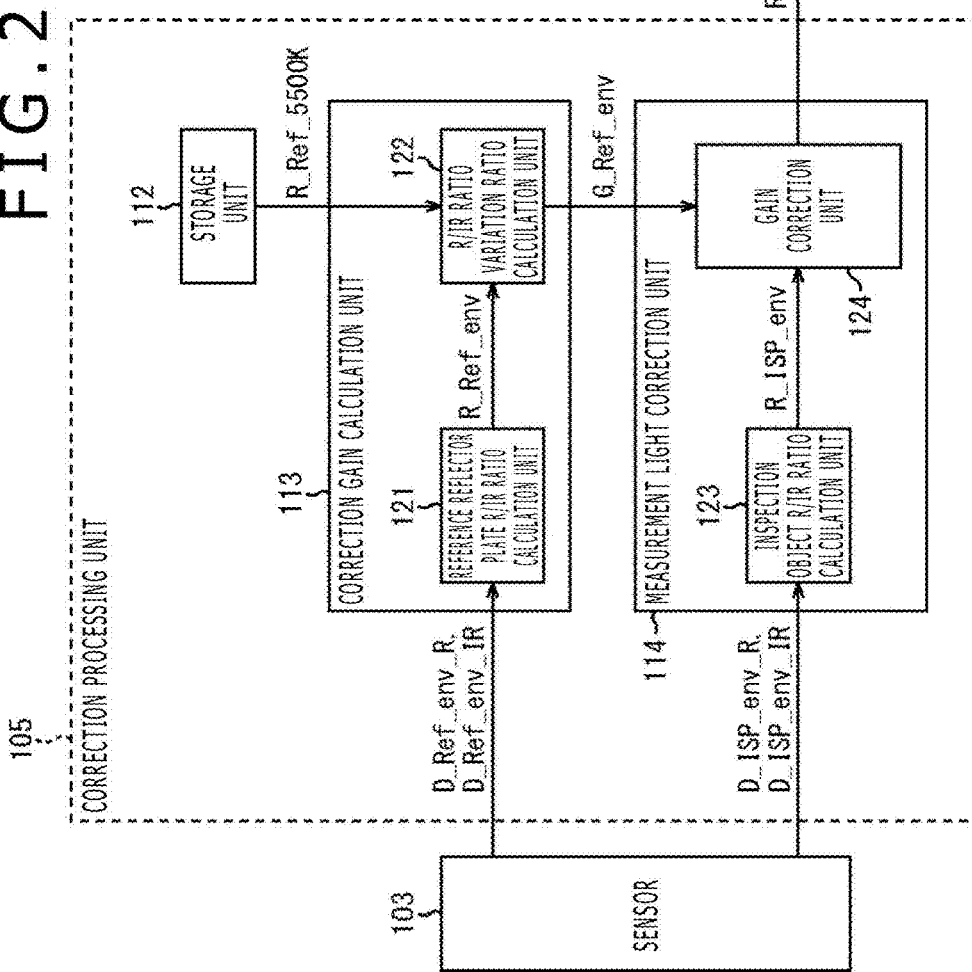
FIG. 24 is a view depicting an example of a second functional configuration of the vegetation inspection apparatus upon measurement of an inspection index.

FIG. 24 is a view depicting a second functional configuration of the vegetation inspection apparatus 10 (FIG. 1) upon measurement of an inspection index (NDVI value) of the inspection object 50 under the measurement light source L1.

The vegetation inspection apparatus 10 of FIG. 24 is different in configuration of the inspection index calculation unit 106 in comparison with the configuration of the vegetation inspection apparatus 10 of FIG. 22 described hereinabove. In particular, in the inspection index calculation unit 106 of FIG. 24, a normalization unit 132 for performing normalization of light source-sensor components with respect to a measurement spectral ratio (R_ISP_env_comp) (of the inspection object 50 under the measurement light source L1) after corrected and a storage unit 133 are further provided at a preceding stage to the NDVI value calculation unit 131.

Here, the reason why such normalization is performed is that a vegetation index such as a normalized vegetation index (NDVI value) does not rely upon the measurement system of a light source and a sensor and is generally defined only by a spectral reflectance characteristic of an object. In other words, the vegetation index is defined, from among characteristics of a light source (reference light source L0), a sensor (sensor 103) and an object (inspection object 50), by the characteristic of the object.

Accordingly, it is desirable to exclude a spectral characteristic of the reference light source L0 (for example, a factor that a spectrum of a light source of the color temperature of 5500K is displaced from a flat spectrum) and a spectral characteristic of the sensor 103 (for example, a sensitivity ratio between the R channel and the IR channel). Therefore, a spectral ratio (R_Flat_5500K) for normalization with only the spectral characteristic of the reference light source L0 and the spectral sensitivity characteristic of the sensor 103 taken into consideration is calculated (measured) in advance and stored into the storage unit 133. Consequently, by dividing the measurement spectral ratio (R_ISP_env_comp) (of the inspection object 50 under the measurement light source L1) after corrected by the spectral ratio (R_Flat_5500K) for normalization, the components of the reference light source L0 and the sensor 103 are normalized.

However, where the R channel value and the IR channel value where measurement (sensing) of an object by a flat spectrum under the reference light source L0 is assumed are represented by D_Flat_5500K_R and D_Flat_5500K_IR, respectively, the spectral ratio (R_Flat_5500K) for normalization can be determined by arithmetically operating an expression (26) given below.

$$R\_Flat\_5500K = D\_Flat\_5500K\_R/D\_Flat\_5500K\_IR \quad (26)$$

Referring back to FIG. 24, the normalization unit 132 reads out information representative of the spectral ratio (R_Flat_5500K) for normalization stored in the storage unit 133. The normalization unit 132 normalizes, on the basis of the spectral ratio (R_Flat_5500K) for normalization read out from the storage unit 133, the measurement spectral ratio (R_ISP_env_comp) (of the inspection object 50 under the measurement light source L1) after corrected supplied from (the gain correction unit 124 of the measurement light correction unit 114 of) the correction processing unit 105, and supplies the spectral ratio (R_ISP_norm) after normalized to the NDVI value calculation unit 131.

The NDVI value calculation unit 131 calculates a normalized vegetation index (NDVI value) as an inspection index of the inspection object 50 on the basis of the spectral ratio (R_ISP_norm) after normalized supplied from the normalization unit 132 and outputs the normalized vegetation index (NDVI value).

It is to be noted that, although the storage unit 112 of the correction processing unit 105 and the storage unit 133 of the inspection index calculation unit 106 in FIG. 24 are configured as storage units separate from each other for the convenience of description, they may otherwise be configured as a single storage unit.

(Second Measurement Process of Inspection Index)

Now, a second measurement process of an inspection index of the inspection object 50 under the measurement light source L1, which is executed by the vegetation inspection apparatus 10 of FIG. 24, is described with reference to a flow chart of FIG. 25.

At steps S151 to S157, a correction gain (G_Ref_env) according to spectral ratios (R_Ref_5500K, R_Ref_env) of the reference reflector plate 101 under the reference light source L0 and the measurement light source L1 is calculated, and a measurement spectral ratio (R_ISP_env) of the inspection object 50 under the measurement light source L1 is corrected using the correction gain (G_Ref_env) similarly as at steps S131 to S137 of FIG. 23.

Figure 25:
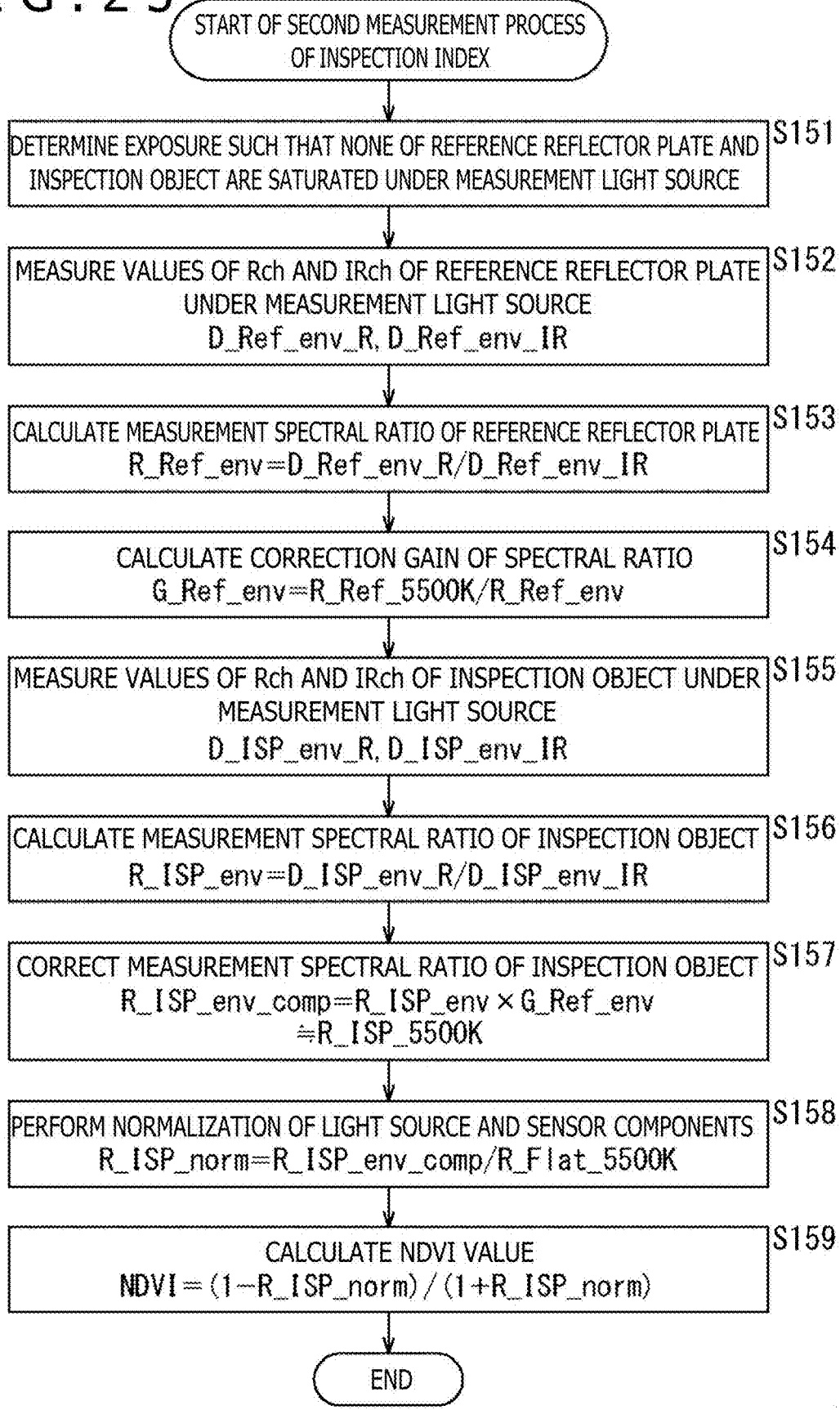
FIG. 25 is a flow chart illustrating a second measurement process of an inspection index.

It is to be noted that, while also FIG. 25 indicates a flow of such processing that the vegetation inspection apparatus 10 measures the reference reflector plate 101 under the measurement light source L1 in the process at step S152 and then measures the inspection object 50 under the measurement light source L1 in the process at step S155, where the reference reflector plate 101 and the inspection object 50 are measured at the same time, the process at step S155 is performed at a timing same as that of the process at step S152. In particular, the vegetation inspection apparatus 10 may perform the measurement processes at step S152 and step S155 simultaneously or at different timings. It is to be noted that the measurement processes at step S152 and step S155 are performed at timings before the measurement results are required by the calculation processes at steps S153, S154, S156 and so forth.

At step S158, the normalization unit 132 performs light source-sensor components in regard to the measurement spectral ratio (R_ISP_env_comp) (of the inspection object 50 under the measurement light source L1) corrected by the process at step S157.

In particular, the normalization unit 132 reads out information indicative of the spectral ratio (R_Flat_5500K) for normalization stored in the storage unit 133 in advance. Then, the normalization unit 132 arithmetically operates an expression (27) given below using the spectral ratio (R_Flat_5500K) for normalization read out from the storage unit 133 to perform normalization of the light source-sensor components with respect to the measurement spectral ratio (R_ISP_env_comp) (of the inspection object 50 under the measurement light source L1) after corrected.

$$R\_ISP\_norm = R\_ISP\_env\_comp/R\_Flat\_5500K \quad (27)$$

At step S159, the NDVI value calculation unit 131 arithmetically operates an expression (27) given below using the measurement spectral ratio (R_ISP_norm) (of the inspection object 50 after corrected) normalized by the process at step S158 to calculate a normalized vegetation index (NDVI value) as an inspection index of the inspection object 50.

$$NDVI = (1 - R\_ISP\_norm)/(1 + R\_ISP\_norm) \quad (28)$$

The second measurement process of an inspection index has been described. In this second measurement process of an inspection index, a correction gain (G_ref_env) according to the spectral ratios (R_Ref_5500K, R_Ref_env) of the reference reflector plate 101 under the reference light source L0 and the measurement light source L1, and the spectral ratio (R_ISP_env) of the inspection object 50 under the measurement light source L1 is corrected using the correction gain (G_Ref_env). Then, the spectral ratio (R_ISP_env_comp) after corrected is normalized, and the inspection index (NDVI value) of the inspection object 50 is calculated using the spectral ratio (R_ISP_norm) after normalized.

Figure 26:
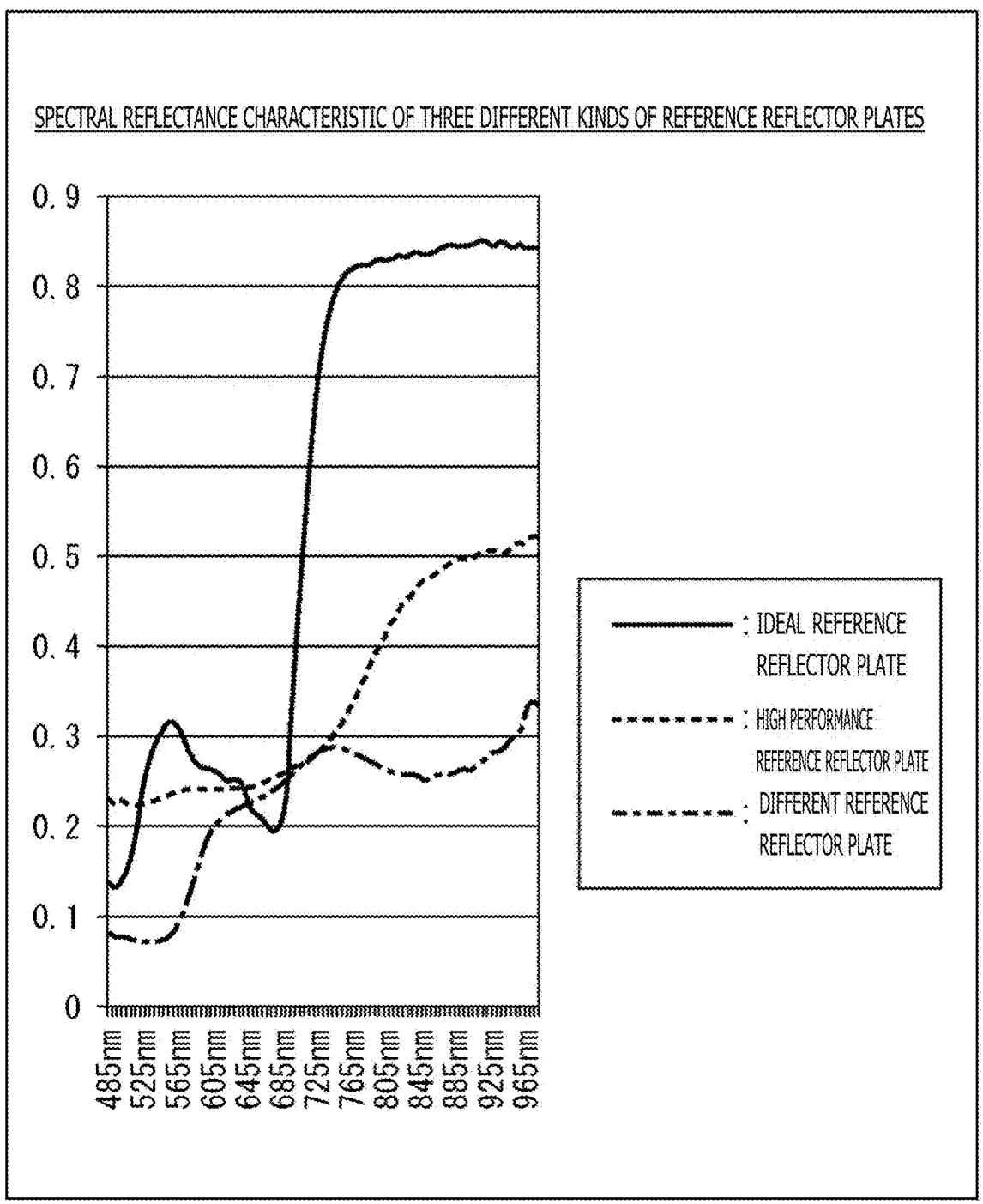
FIG. 26 is a view depicting a spectral reflectance characteristic of three different kinds of reference reflector plates.

Here, removal of the light source dependency by using the reference reflector plate 101 of the present technology is described in more detail with reference to FIGS. 26 to 29. FIG. 26 is a view depicting a spectral reflectance characteristic of three different kinds of reference reflector plates 101.

Referring to FIG. 26, from among the three different kinds of reference reflector plates 101, an ideal reference reflector plate 101I has, as a spectral reflectance characteristic thereof, a characteristic according to the spectral reflectance of the inspection object 50 (plant) (a substantially same characteristic). NDVI values of plants (plant A, plant B and plant C) of the same type of different vegetations when measurement light correction is performed using the ideal reference reflector plate 101I are depicted in FIG. 27.

Figure 27:
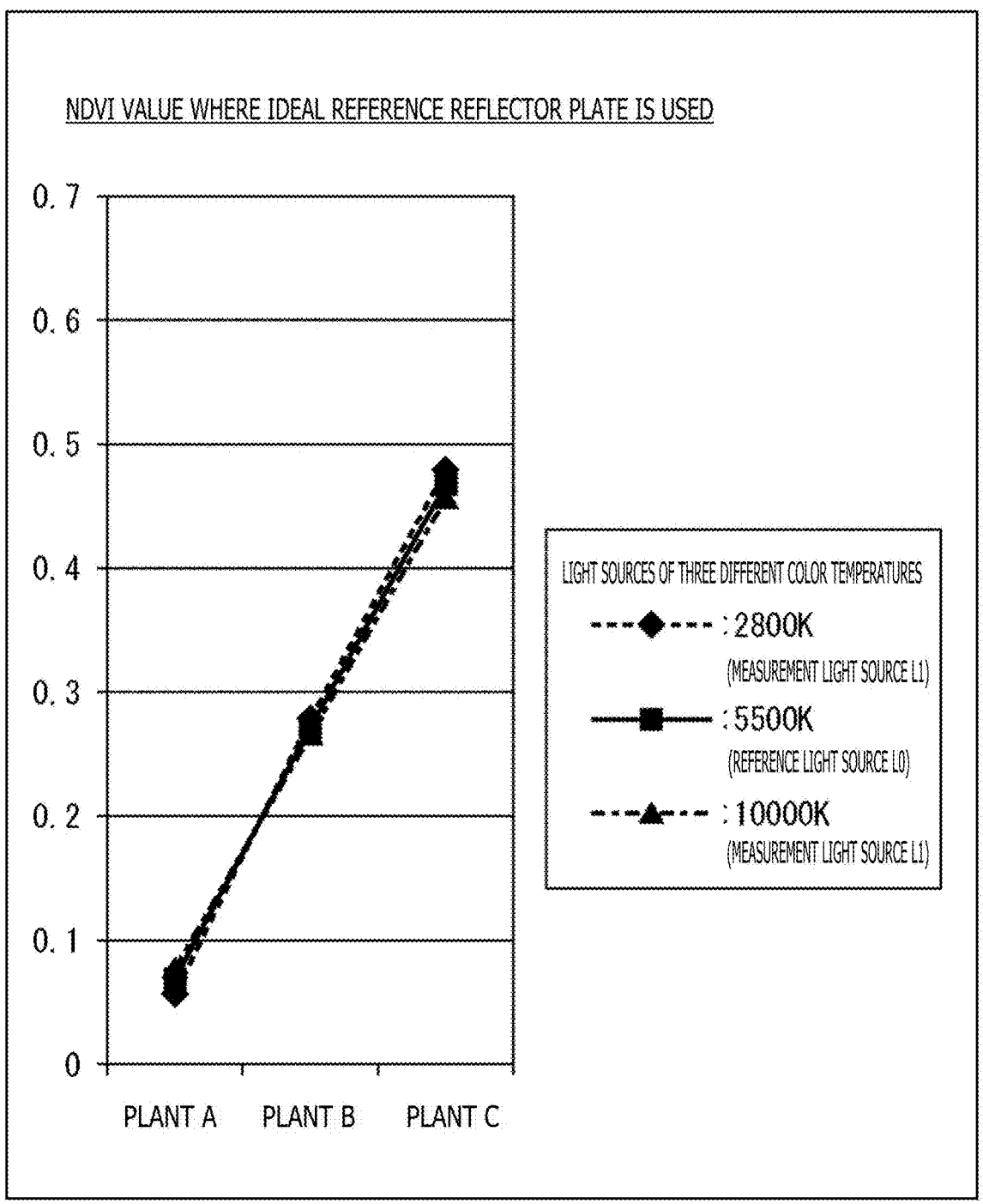
FIG. 27 is a view depicting an NDVI value where an ideal reference reflector plate is used.

In FIG. 27, while a light source of a color temperature of 5500K is used as the reference light source L0 and a light source of another color temperature of 2800K and a light source of a further color temperature of 10000K are used as the measurement light sources L1, NDVI values of the plants measured under the light sources of the different color temperatures indicate proximate values. In particular, since it is considered that, as the difference appearing between NDVI values of the plants decreases, the dependency upon the light sources of the color temperatures is removed better, the light source dependency can be removed well by using the ideal reference reflector plate 101I.

Further, in FIG. 26, spectral reflectance characteristics of a high performance reference reflector plate 101H and a different reference reflector plate 101O are depicted in addition to that of the ideal reference reflector plate 101I. Although it is not said that the high performance reference reflector plate 101H has a characteristic same as the spectral reflectance characteristic of the inspection object 50 (plant) if the spectral reflectance characteristic of the high performance reference reflector plate 101H is compared with that of the ideal reference reflector plate 101I, the high performance reference reflector plate 101H has a comparatively close characteristic (characteristic within a permissible range).

Figure 28:
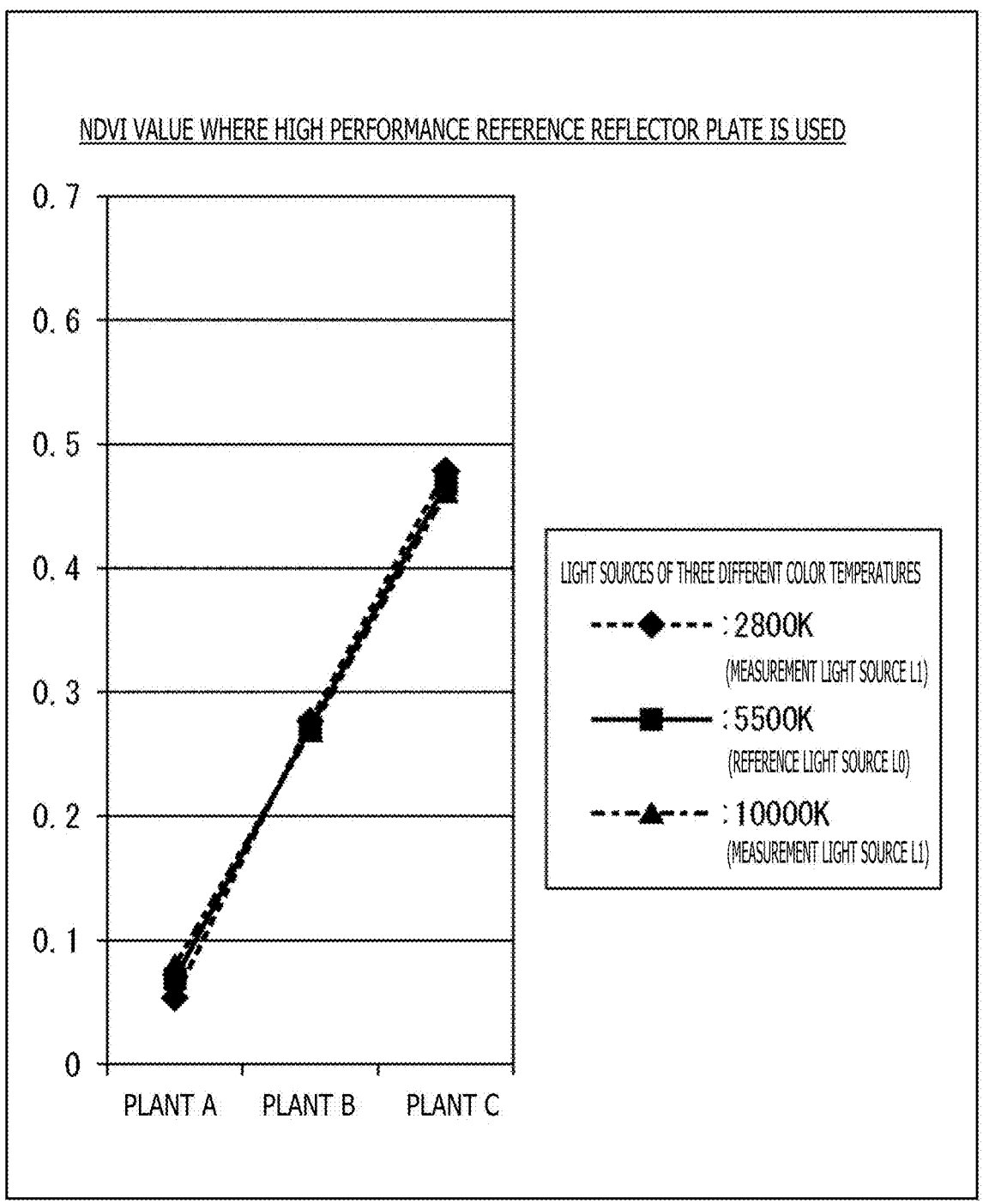
FIG. 28 is a view depicting an NDVI value where a high performance reference reflector plate is used.

NDVI values of plants (plant A, plant B and plant C) of a same type of different vegetations where measurement light correction is performed using the high performance reference reflector plate 101H are depicted in FIG. 28. In FIG. 28, NDVI values of the plants measured under the reference light source L0 (light source of the color temperature of 5500K) and the measurement light sources L1 (light sources of 2800K and 10000K) are approximate values. In other words, where the high performance reference reflector plate 101H is used, the light source dependency can be removed well.

Figure 29:
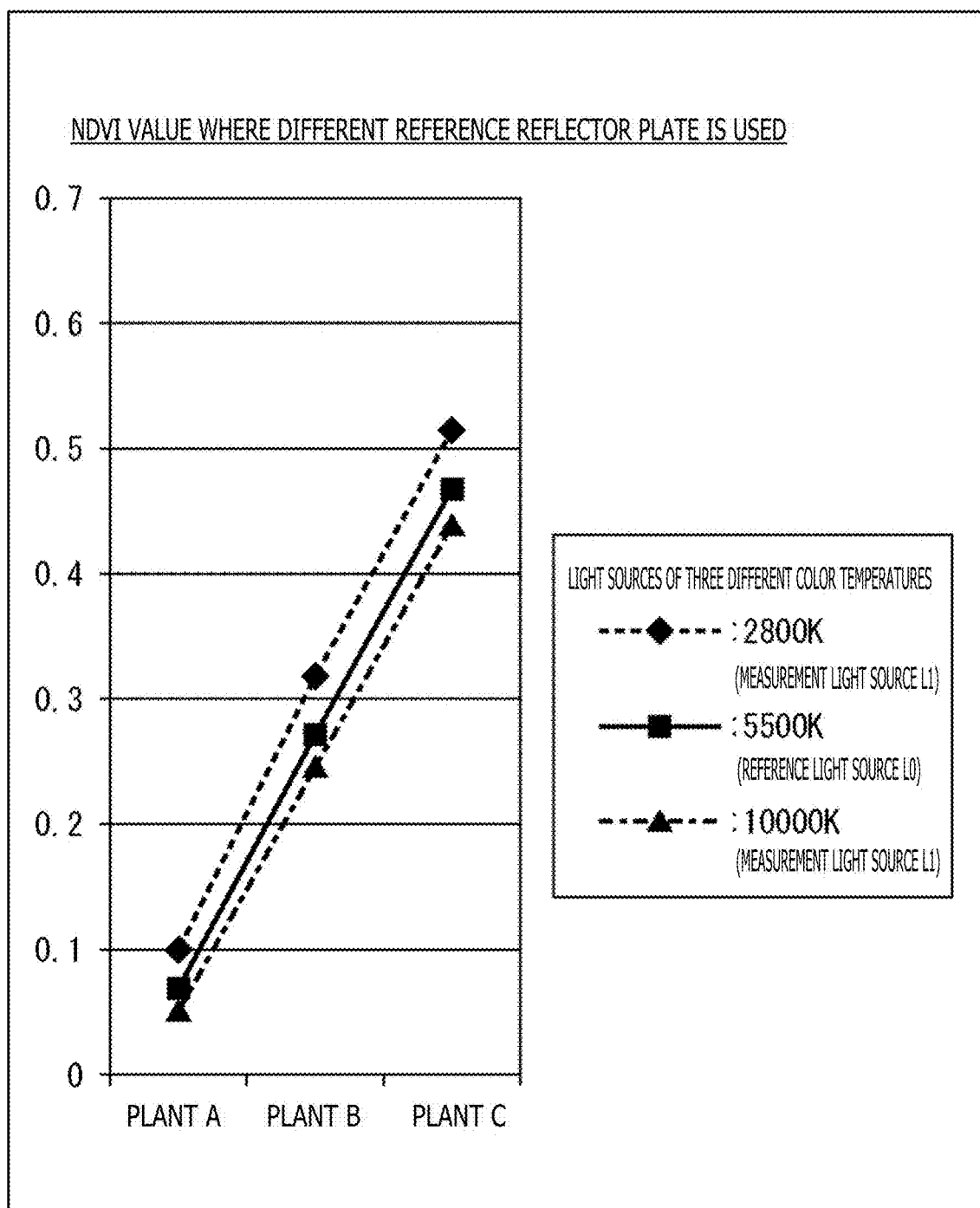
FIG. 29 is a view depicting an NDVI value where a different reference reflector plate is used.

Referring back to FIG. 26, the different reference reflector plate 101O has a characteristic different from a spectral reflectance characteristic of the inspection object 50 (plant). NDVI values of plants (plant A, plant B and plant C) of a same type of different vegetations where measurement light correction is performed using the different reference reflector plate 101O are depicted in FIG. 29. In FIG. 29, NDVI values of the plants measured under the reference light source L0 (light source of the color temperature of 5500K) and the measurement light sources L1 (light sources of 2800K and 10000K) are values having great differences (different values). In other words, where the different reference reflector plate 101O is used, an error occurs with measurement light correction, and the light source dependency cannot be removed.

In this manner, where the ideal reference reflector plate 101I and the high performance reference reflector plate 101H are used, the light source dependency can be removed well. In particular, although it is ideal to produce the ideal reference reflector plate 101I as the reference reflector plate 101 to be designed by the spectral reflectance design apparatus 20 (FIG. 7), even where the reference reflector plate 101I that accurately reflects a spectral reflectance characteristic of the inspection object 50 cannot be produced, if a high performance reference reflector plate 101H having a characteristic close to some degree to the spectral reflectance characteristic of the inspection object 50 (characteristic within a tolerance) is produced, then it is possible to remove the light source dependency using the reference reflector plate 101H. In other words, the reference reflector plate 101 is produced after a characteristic of the inspection object 50 such as a plant is recognized.

Further, where a plurality of reference reflector plates 101 are available, by selecting a reference reflector plate 101 confirming to the ideal reference reflector plate 101I (or to the high performance reference reflector plate 101H) from among the plurality of reference reflector plates 101, the light dependency can be removed by the selected reference reflector plate 101.

Furthermore, where a reference reflector plate 101 produced in accordance with a target spectral reflectance determined by the second design process of a spectral reflectance (FIG. 9), since the reference reflector plate 101 is designed such that the average spectral reflectance O_PLT_AVE(λ) keeps a minimum value of the characteristic variation of the plant (minimum reflectance), by performing exposure control of the exposure control target upon measurement in the measurement process of an inspection index (FIGS. 23 and 25) in accordance with the inspection object 50 (plant), it is guaranteed that the measurement, value of the reference reflector plate 101 is not saturated without fail. As a result, it is possible to place the measurement values (R channel values and IR channel values) of all objects (inspection object 50 (plant) and reference reflector plate 101) into the dynamic range of the sensor 103 (not into a saturated state).

On the other hand, where a reference reflector plate 101 produced in accordance with a target spectral reflectance determined by the third design process of a spectral reflectance (FIG. 14), since the reference reflector plate 101 is designed such that the average spectral reflectance O_PLT_AVE(λ) keeps a maximum value of the characteristic variation of the plant (maximum reflectance), if exposure control of the exposure control target upon measurement in the measurement process of an inspection index (FIGS. 23 and 25) in accordance with the reference reflector plate 101, it is guaranteed that the measurement value of the inspection object 50 (plant) is not saturated without fail. As a result, it is possible to place the measurement values (R channel values and IR channel values) of all objects (inspection object 50 (plant) and reference reflector plate 101) into the dynamic range of the sensor 103 (not into a saturated state).

From this, where a reference reflector plate 101 produced in accordance with a target spectral reflectance determined by the second design process of a spectral reflectance (FIG. 9) or the third design process of a spectral reflectance (FIG. 14) is used, the exposure control target upon measurement is the measurement process of an inspection index (FIGS. 23 and 25) may be set to one of the inspection object 50 (plant) and the reference reflector plate 101, and since there is no necessity to perform exposure control separately for the inspection object 50 (plant) and the reference reflector plate 101, simple and easy exposure control can be performed.

<5. Modifications>

(Reflector Plates are Arranged in Mosaic Pattern)

Figure 30:
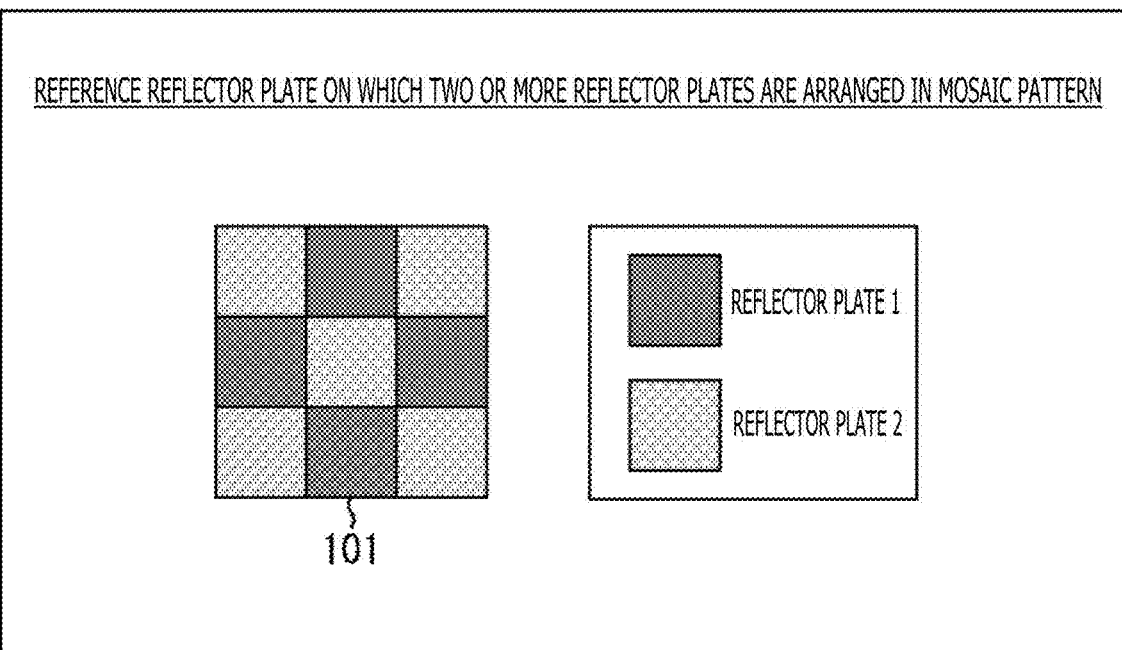
FIG. 30 is a view depicting a reference reflector plate in which two reflector plates are arranged in a mosaic pattern.

While it is described in the foregoing description that the reference reflector plate 101 is configured from a single reflector plate, it may otherwise be configured from two or more reflector plates. FIG. 30 is a view depicting a reference reflector plate 101 in which two reflector plates are arranged in a mosaic pattern. Referring to FIG. 30, the reference reflector plate 101 is configured by specially arranging reflector plates 1 and reflector plates 2 having different reflectances from each other in a mosaic pattern.

Figure 31:
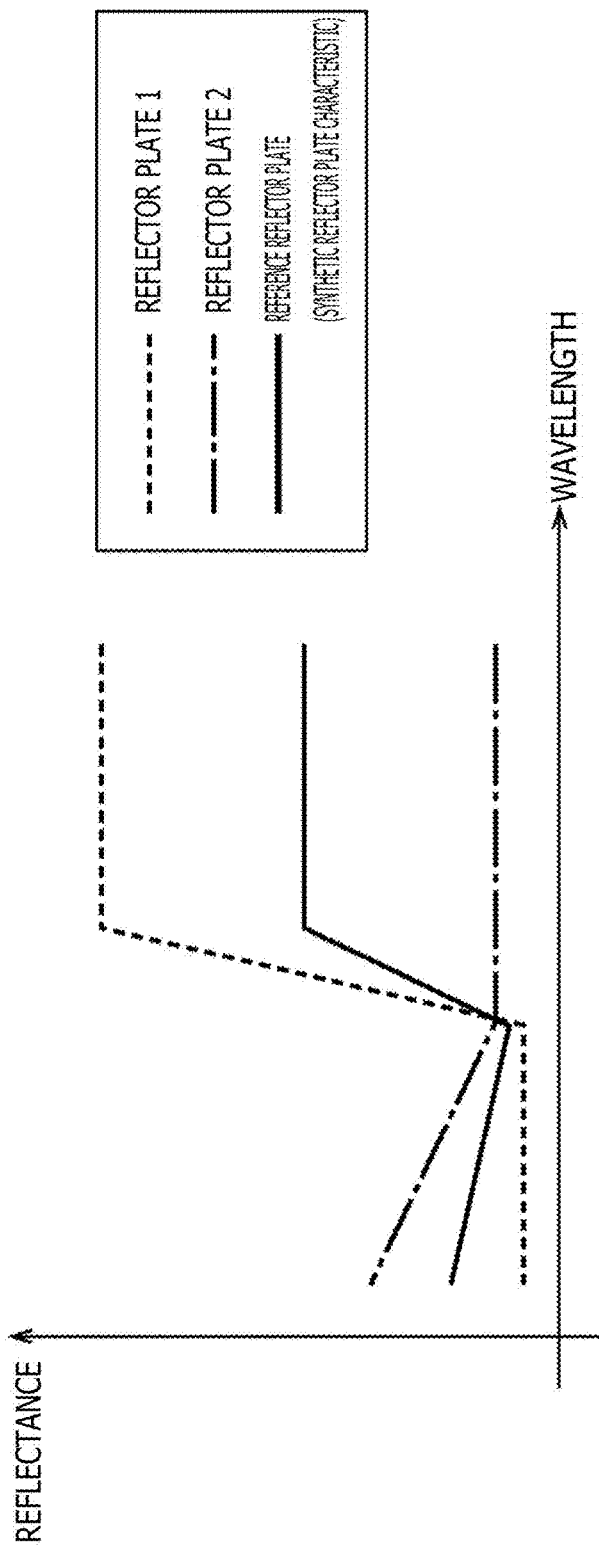
FIG. 31 is a view depicting a synthetic reflectance characteristic of the reference reflector plate in which two reflector plates are arranged in a mosaic pattern.

FIG. 31 is a view depicting a synthetic reflectance characteristic of the reference reflector plate 101 in which two reflector plates are arranged in a mosaic pattern. Referring to FIG. 31, the axis of abscissa represents the wavelength (nm) and the axis of ordinate represents the reflectance. As depicted in FIG. 31, the reflector plate 1 and the reflector plate 2 have reflectances different from each other, and by synthesizing the reflectances, a synthetic reflectance is obtained (graph of a solid line in FIG. 31). The synthetic reflectance obtained in this manner is determined as a target spectral reflectance, and a reference reflector plate 101 according to the target spectral reflectance is produced.

In particular, in a design process of a spectral reflectance, when a target spectral reflectance for producing a reference reflector plate 101 cannot be implemented using one reflector plate, a plurality of reflector plates are combined to synthesize the reflectances of the reflector plates to make it possible to implement the target spectral reflectance according to a characteristic of an inspection object 50 such as a plant. In other words, the R channel value and the IR channel value of each of the reflector plates 1 and 2 are measured and weighted addition or spatial integration of the P channel values and the IR channel values is performed to equivalently measure (sense) a reflector plate (virtual reflector plate) having a characteristic obtained by the weighted addition of the spectral reflectances of the reflector plates. Such measurement is equivalent to measurement of the R channel value and the IR channel value.

It is to be noted that, although FIGS. 30 and 31 indicate an example in which the two reflector plates of the reflector plate 1 and the reflector plate 2 are arranged, it is possible to combine a plurality of reflector plates equal to two or more to configure a reference reflector plate 101. Further, the arrangement method of the plurality of reflector plates is not limited to a mosaic arrangement, but some other arrangement by which a target spectral reflectance can be implemented may be adopted. Further, the synthetic reflectance characteristic of the reference reflector plate 101 may be changed, for example, by changing the weight upon the weighted addition described above or the area ratio between the reflector plate 1 and the reflector plate 2 to be arranged on the reference reflector plate 101.

(Example of Attachment of Reference Reflector Plate)

Although the reference reflector plate 101 can be installed at a position at which it can be measured by the sensor 103, for example, it can be attached to a predetermined position in front of a camera in which the sensor 103 is incorporated. FIG. 32 is a view depicting an example in a case in which the reference reflector plate 101 is attached in front of a camera.

In A of FIG. 32, a bar-like member is attached to a camera as the vegetation inspection apparatus 10, and a reference reflector plate 101 having a circular shape is attached to a distal end of the bar-like member (end at the object side). Meanwhile, B of FIG. 32 depicts that, as an object that is to be measured (sensed) by the camera as the vegetation inspection apparatus 10, a turf (lawn) of a stadium that is an inspection object 50 and the reference reflector plate 101 having a circular shape exist within the same angle of view.

In such a state that the inspection object 50 and the reference reflector plate 101 can be measured at the same time, a measurement process (FIGS. 23 and 25) of an inspection index of the inspection object 50 under the measurement light source L1 is executed. Consequently, only by measuring (sensing) the turf (lawn) of the stadium and the reference reflector plate 101 at the same time, for example, by the camera as the vegetation inspection apparatus 10, a normalized vegetation index (NDVI value) of the turf in the angle of view of the camera is obtained. Therefore, by displaying a result of this, the state of the turf of the stadium can be confirmed rapidly.

It is to be noted that, although it is necessary to execute a measurement process (FIG. 20) of the reference reflector plate 101 under the reference light source L0 preceding to the measurement process (FIGS. 23 and 25) of an inspection index of the inspection object 50 under the measurement light source L1, this measurement process (FIG. 20) is executed in a state in which only the reference reflector plate 101 exists within the angle of view.

However, the measurement process (FIG. 20) of the reference reflector plate 101 under the reference light source L0 is a process that is required only once at a point of time at which a reference reflector plate 101 is produced and a camera (vegetation inspection apparatus 10) that uses the reference reflector plate 101 is determined, and if a reference spectral ratio (R_Ref_5500K) of the reference reflector plate 101 under the reference light source L0 (for example, a light source of the color temperature of 5500K) is stored once into the storage unit 112, then the process need not be performed later unless the combination of the reference reflector plate 101 and the camera (vegetation inspection apparatus 10) is changed.

Further, while it is described that, in FIG. 32, the shape of the reference reflector plate 101 is a circular shape, the shape of the reference reflector plate 101 may be a different shape such as, for example, an elliptical shape or a quadrangular shape only if the reference reflector plate 101 has a characteristic according to the spectral reflectance characteristic of the inspection object 50 (in the example of FIG. 32, the turf (lawn)).

It is to be noted that, as the camera (vegetation inspection apparatus 10) described above, for example, a multispectral camera can be used by which a multispectral signal is obtained by dispersing light (reflection light) incident through a lens into a plurality of wavelength bands and forming an image of the light in the wavelength bands on a two-dimensional sensor face. Further, for the camera (vegetation inspection apparatus 10) described above, a camera having a spectral sensing function such as, for example, a so-called hyperspectral camera can be used in addition to the multispectral camera.

(Inspection Object and Inspection Index)

While, in the foregoing description, the inspection object 50 is described taking a plant (for example, a turf or the like) as an example, the inspection object 50 may be an object other than a plant. For example, by measuring, in a manufacturing factory of food, an inspection index of food manufactured by the inspection apparatus (vegetation inspection apparatus 10) of the present technology as the inspection object 50, as inspection index of food can be measured without relying upon a light source in the factory. Consequently, even if the illumination light in the factory varies, ranking of food can be performed.

Further, while, in the foregoing description, the inspection index when a plant is set as the inspection object 50 is described taking a normalized vegetation index (NDVI value) as an example, a vegetation index different from the normalized vegetation index (NDVI value) may be measured. For example, as the different vegetation index, a ratio vegetation index (RVI: Ratio Vegetation Index), a difference vegetation index (DVI: Difference Vegetation Index) and so forth can be used.

Here, the ratio vegetation index (RVI value) is calculated by arithmetically operating an expression (29) given below.

$$RVI = IR/R \quad (29)$$

Meanwhile, the difference vegetation index (DVI value) is calculated by arithmetically operating an expression (30) given below.

$$DVI = IR - R \quad (30)$$

It is to be noted that, in the expression (29) and the expression (30), IR represents a reflectance in the near infrared region, and R represents a reflectance in the visible region (red). It is to be noted that, although only vegetation indexes in which IR and R are used as parameters are exemplified here, it is naturally possible to measure a different vegetation index using a reflectance of light in a visible region other than red or the like as a parameter. The spectral ratio is not limited to the combination of R and IR. From the sensor 103, components of other wavelength bands such as G or B other than R and IR may be outputted as outputs of RGBIR.

(Different Configuration Example of Vegetation Inspection Apparatus)

Figure 33:
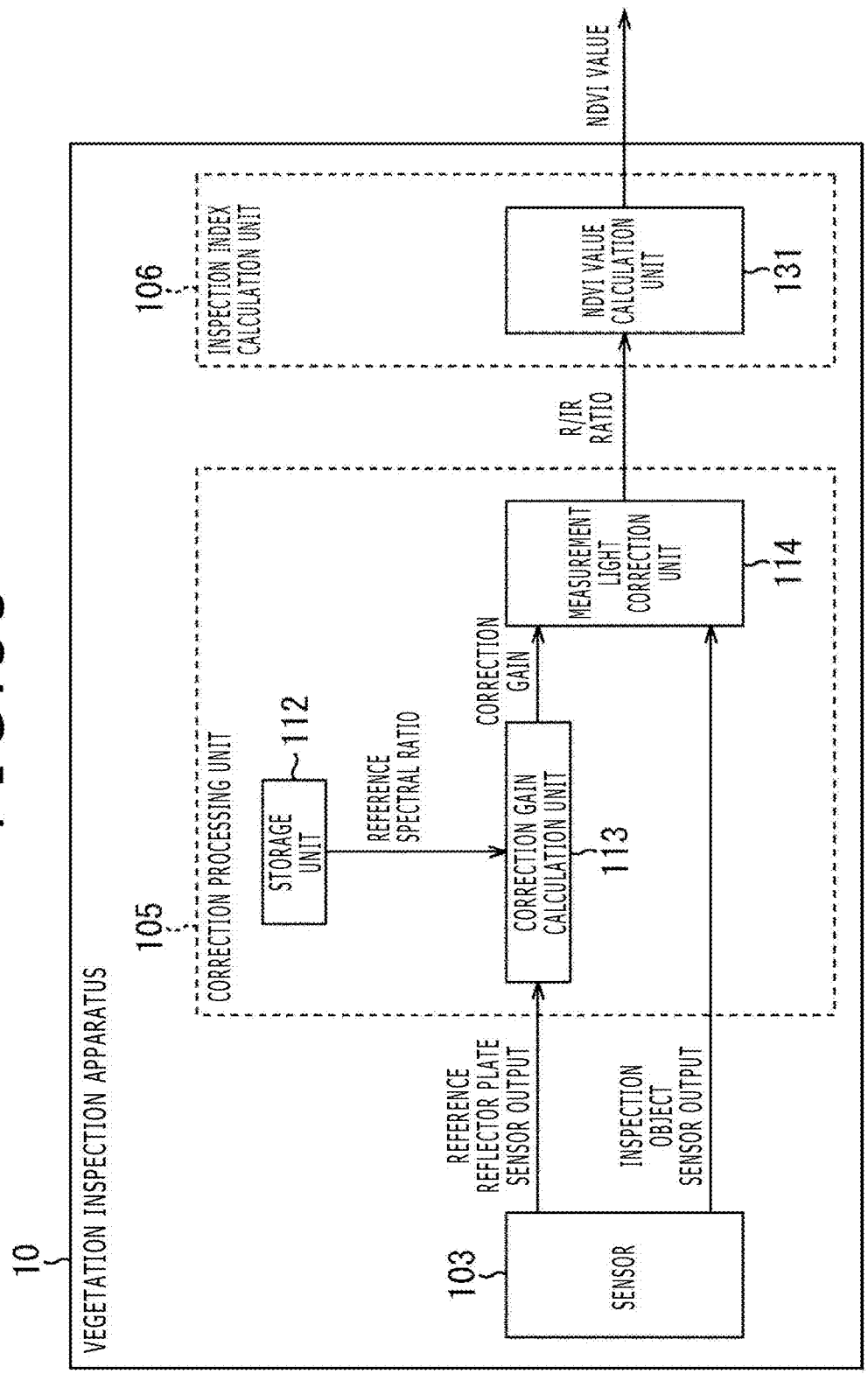
FIG. 33 is a view depicting an example of a configuration of the vegetation inspection apparatus.

FIG. 33 depicts a configuration in a case in which the vegetation inspection apparatus 10 includes a sensor 103, a correction processing unit 105 and an inspection index calculation unit 106. This configuration corresponds to the configuration of FIG. 22 described hereinabove and is a configuration in the case in which the vegetation inspection apparatus 10 has all functions of the sensor 103, correction processing unit 105, inspection index calculation unit 106 and so forth.

While, in the foregoing description, a case is described in which the vegetation inspection apparatus 10 has all functions like the configuration depicted in FIG. 33, part of the functions of the vegetation inspection apparatus 10 (FIG. 1) may be had by some other apparatus. In the following, a configuration in which a different apparatus has part of the functions of the vegetation inspection apparatus 10 (FIG. 1) is describe with reference to FIGS. 34 to 36. It is to be noted that, in FIGS. 34 to 36, like portions to the blocks configuring FIG. 22 described hereinabove are denoted by like reference characters, and description of them is suitably omitted. Further, this similarly applies also the configuration of FIG. 24 though not depicted.

(First Configuration Example of Vegetation Inspection System)

Figure 34:
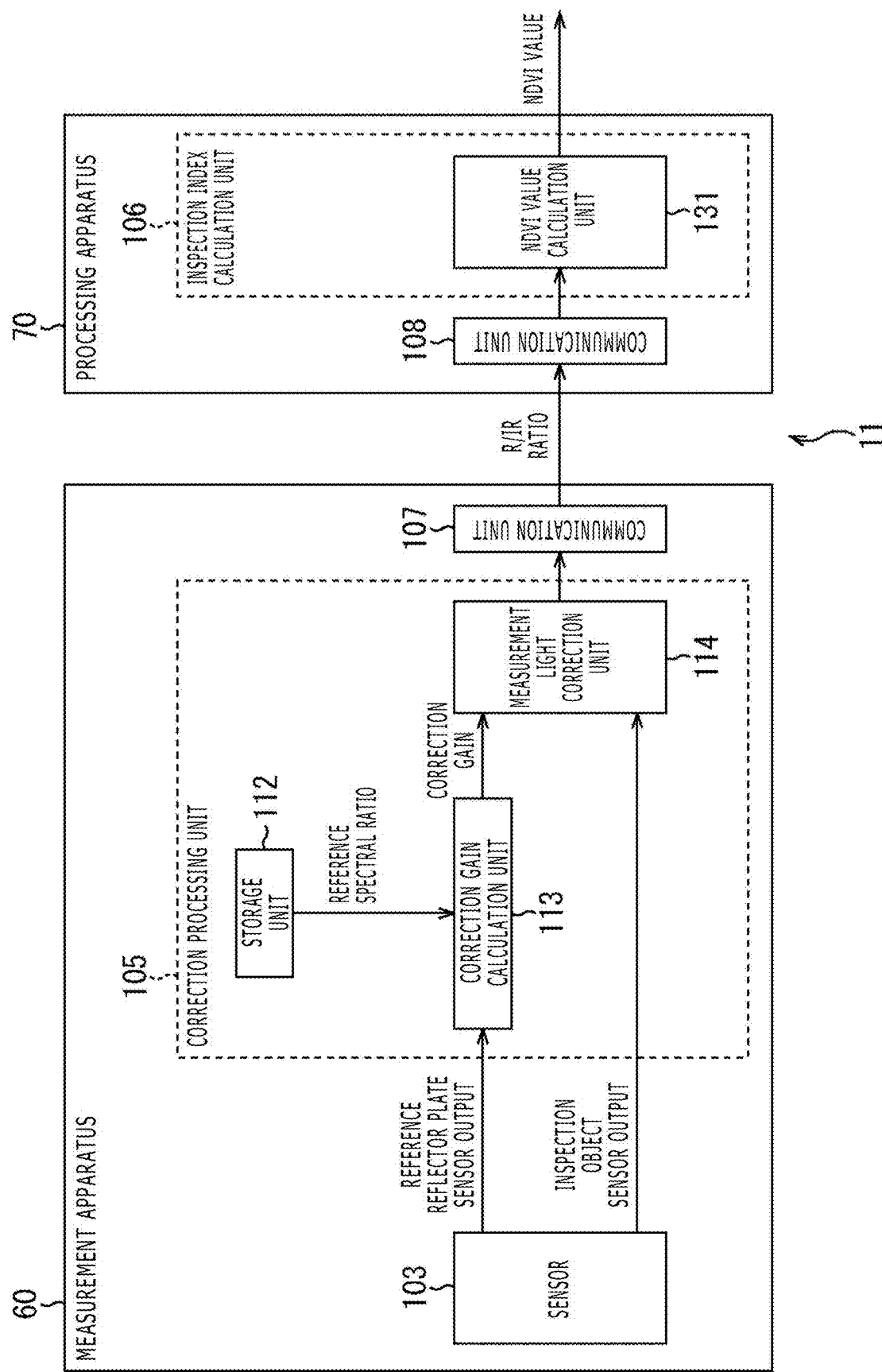
FIG. 34 is a view depicting a first example of a configuration of a vegetation inspection system.

FIG. 34 is a view depicting a first example of a configuration of the vegetation inspection system.

Referring to FIG. 34, the vegetation inspection system 11 is configured from a measurement apparatus 60 and a processing apparatus 70. Here, both the measurement apparatus 60 and the processing apparatus 70 have a communication function and can exchange data utilizing wireless communication or wired communication in compliance with a predetermined standard. For example, where the processing apparatus 70 is a server provided on the Internet, the measurement apparatus 60 accesses the processing apparatus 70 through the Internet and transmits data to the processing apparatus 70.

The measurement apparatus 60 is configured from a sensor 103, a correction processing unit 105 and a communication unit 107. Further, the correction processing unit 105 is configured from a storage unit 112, a correction gain calculation unit 113 and a measurement light correction unit 114.

The correction gain calculation unit 113 refers to a reference spectral ratio (R/IR ratio) stored in the storage unit 112 to calculate a correction gain according a measurement spectral ratio (R/IR ratio) of the reference reflector plate 101 calculated from an output value of the sensor 103 and supplies the correction gain to the measurement light correction unit 114.

The measurement light correction unit 114 uses the correction gain from the correction gain calculation unit 113 to correct the measurement spectral ratio (R/IR ratio) of the inspection object 50 calculated from an output value of the sensor 103 and supplies the resulting spectral ratio (R/IR ratio) to the communication unit 107. The communication unit 107 transmits information indicative of the measurement spectral ratio (R/IR ratio) (of the inspection object 50) after corrected supplied from the measurement light correction unit 114 to the processing apparatus 70 utilizing, for example, wireless communication or the like.

The processing apparatus 70 is configured from an inspection index calculation unit 106 and a communication unit 108. Further, the inspection index calculation unit 106 is configured from an NDVI value calculation unit 131. The communication unit 108 receives information transmitted thereto from the measurement, apparatus 60 and indicative of the measurement spectral ratio (R/IR ratio) (of the inspection object 50) after corrected and supplies the received information to the NDVI value calculation unit 131. The NDVI value calculation unit 131 uses the information supplied from the communication unit 108 and indicative of the measurement spectral ratio (R/IR ratio) (of the inspection object 50) after corrected to calculate a normalized vegetation index (NDVI value) as an inspection index of the inspection object 50 and outputs the normalized vegetation index (NDVI value).

(Second Configuration Example of Vegetation Inspection System)

Figure 35:
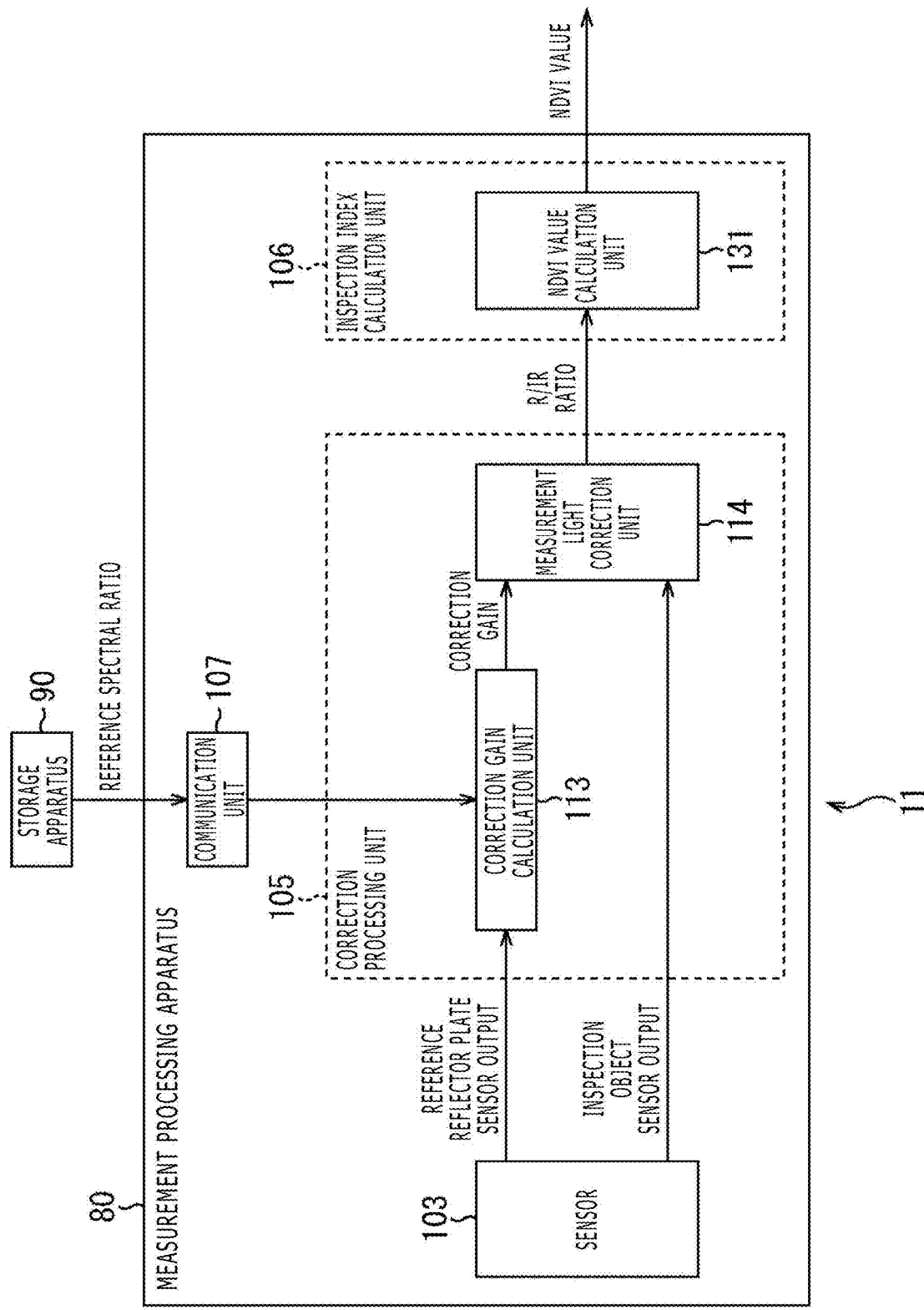
FIG. 35 is a view depicting a second example of a configuration of the vegetation inspection system.

FIG. 35 is a view depicting a second configuration example of the vegetation inspection system.

Referring to FIG. 35, the vegetation inspection system 11 is configured from a measurement processing apparatus 80 and a storage apparatus 90. Here, both the measurement processing apparatus 80 and the storage apparatus 90 have a communication function and can exchange data utilizing wireless communication or wired communication in compliance with a predetermined standard. For example, where the storage apparatus 90 is a server provided on the Internet, the measurement processing apparatus 80 accesses the storage apparatus 90 through the Internet and receives data from the storage apparatus 90.

The measurement processing apparatus 80 is configured from a sensor 103, a correction processing unit 105, an inspection index calculation unit 106 and a communication unit 107. Further, the correction processing unit 105 is configured from a correction gain calculation unit 113 and a measurement light correction unit 114. The inspection index calculation unit 106 is configured from an NDVI value calculation unit 131.

The communication unit 107 receives, upon measurement of the inspection object 50, a reference spectral ratio (R/IR ratio) from the storage apparatus 90, for example, utilizing wireless communication or the like and supplies the reference spectral ratio (R/IR ratio) to the correction gain calculation unit 113. The correction gain calculation unit 113 refers to the reference spectral ratio (R/IR ratio) supplied thereto from the communication unit 107 to calculate a correction gain according to a measurement spectral ratio (R/IR ratio) of the reference reflector plate 101 calculated from an output value of the sensor 103 and supplies the correction gain to the measurement light correction unit 114.

The measurement light correction unit 114 corrects the measurement spectral ratio (R/IR ratio) of the inspection object 50 calculated from an output value of the sensor 103 using the correction gain from the correction gain calculation unit 113 and supplies the corrected measurement spectral ratio (R/IR ratio) to the inspection index calculation unit 106. The NDVI value calculation unit 131 uses information supplied from the measurement light correction unit 114 and indicative of the measurement spectral ratio (R/IR ratio) (of the inspection object 50) after corrected to calculate a normalized vegetation index (NDVI value) as an inspection index of the inspection object 50 and outputs the normalized vegetation index (NDVI value).

For example, where the reference spectral ratio (R/IR ratio) is calculated by an apparatus different from the measurement processing apparatus 80, the reference spectral ratio (R/IR ratio) calculated by the different apparatus is stored into the storage apparatus 90. However, the different apparatus may provide the reference spectral ratio (R/IR ratio) directly to the measurement processing apparatus 80. Alternatively, the storage apparatus 90 may store a spectral ratio for normalization in addition to the reference spectral ratio (R/IR ratio). Also it is possible for the reference spectral ratio or the spectral ratio for normalization to be diverted to a separate apparatus different from the measurement processing apparatus 80.

(Third Configuration Example of Vegetation Inspection System)

Figure 36:
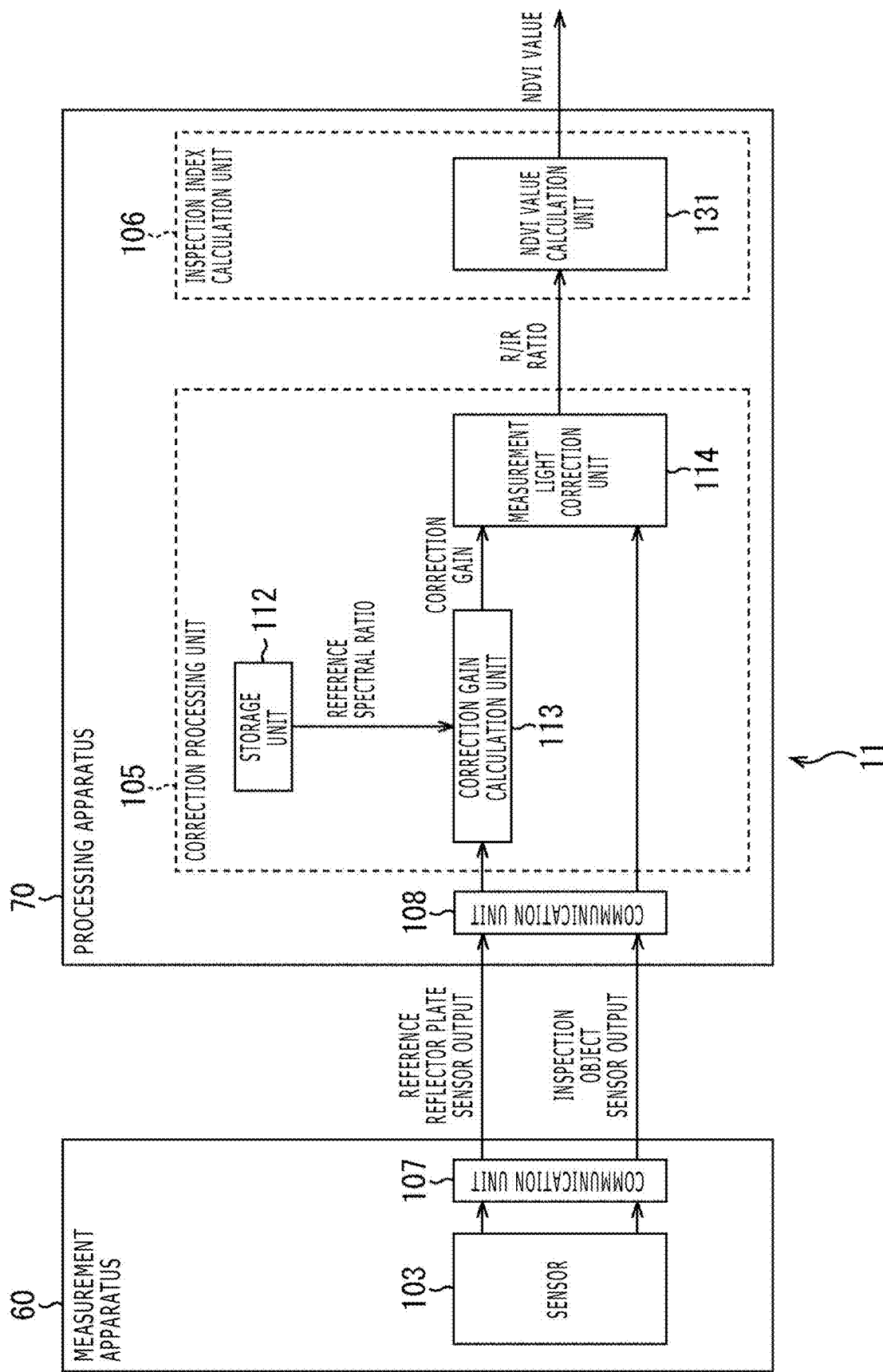
FIG. 36 is a view depicting a third example of a configuration of the vegetation inspection system.

FIG. 36 is a view depicting a third configuration example of the vegetation inspection system.

Referring to FIG. 36, the vegetation inspection system 11 is configured from a measurement apparatus 60 and processing apparatus 70. Here, both the measurement apparatus 60 and the processing apparatus 70 have a communication function and can exchange data utilizing wireless communication or wired communication in compliance with a predetermined standard. For example, where the processing apparatus 70 is a server provided on the Internet, the measurement apparatus 60 accesses the processing apparatus 70 through the internet and transmits data to the processing apparatus 70.

The measurement apparatus 60 is configured from a sensor 103 and a communication unit 107. The sensor 103 measures the R channel value and the IR channel value of the reference reflector plate 101 and the inspection object 50 and supplies the measured values to the communication unit 107. The communication unit 107 transmits the R channel values and the IR channel values supplied from the sensor 103 to the processing apparatus 70, for example, utilizing wireless communication or the like.

The processing apparatus 70 is configured from a correction processing unit 105, an inspection index calculation unit 106 and a communication unit 108. Further, the correction processing unit 105 is configured from a storage unit 112, a correction gain calculation unit 113 and a measurement light correction unit 114. The inspection index calculation unit 106 is configured from an NDVI value calculation unit 131.

The communication unit 108 receives R channel values and IR channel values of the reference reflector plate 101 and the inspection object 50 transmitted from the measurement apparatus 60, and supplies the R channel value and the IR channel value of the reference reflector plate 101 to the correction gain calculation unit 113 and supplies the R channel value and the IR channel value of the inspection object 50 to the measurement light correction unit 114.

The correction gain calculation unit 113 refers to a reference spectral ratio (R/IR ratio) stored in the storage unit 112 to calculate a correction gain according to a measurement spectral ratio (R/IR ratio) of the reference reflector plate 101 calculated from the channel values from the communication unit 108 and supplies the correction gain to the measurement light correction unit 114.

The measurement light correction unit 114 uses the correction gain from the correction gain calculation unit 113 to correct a measurement spectral ratio (R/IR ratio) of the inspection object 50 calculated from the channel values from the communication unit 108 and supplies the corrected measurement spectral ratio (R/IR ratio) to the NDVI value calculation unit 131. The NDVI value calculation unit 131 uses information supplied from the measurement light correction unit 114 and indicative of the measurement spectral ratio (R/IR ratio) (of the inspection object 50) after corrected to calculate a normalized vegetation index (NDVI value) as an inspection index of the inspection object 50 and outputs the normalized vegetation index (NDVI value).

It is to be noted that the term system signifies a logical set of a plurality of apparatus. Further, the configurations of FIGS. 34 to 36 are an example of configurations in the case where a different apparatus has part of the functions the vegetation inspection apparatus 10 has, and also it is possible to adopt a different configuration. For example, in the configurations of FIGS. 35 and 36, it is possible for (the NDVI value calculation unit 131 of) the inspection index calculation unit 106 to be provided by a different apparatus.

Further, in the vegetation inspection apparatus 10 of FIG. 33 or (the processing apparatus 70 or the measurement processing apparatus 80 of) the vegetation inspection systems 11 of FIGS. 34 to 36, a display controlling unit (not detected) may be provided at a succeeding stage to the inspection index calculation unit 106 such that the display controlling unit controls a display unit (not depicted) to display an NDVI image on the basis of a normalized vegetation index (NDVI value) calculated by (the NDVI value calculation unit 131 of) the inspection index calculation unit 106. However, the display unit that displays an NDVI may be provided in the inside of (the processing apparatus 70 or the measurement processing apparatus 80 of) the vegetation inspection apparatus 10 or the vegetation inspection system 11 or may be a display apparatus (not depicted provided outside the apparatus mentioned.

(Particular Example of Measurement Apparatus)

Figure 37:
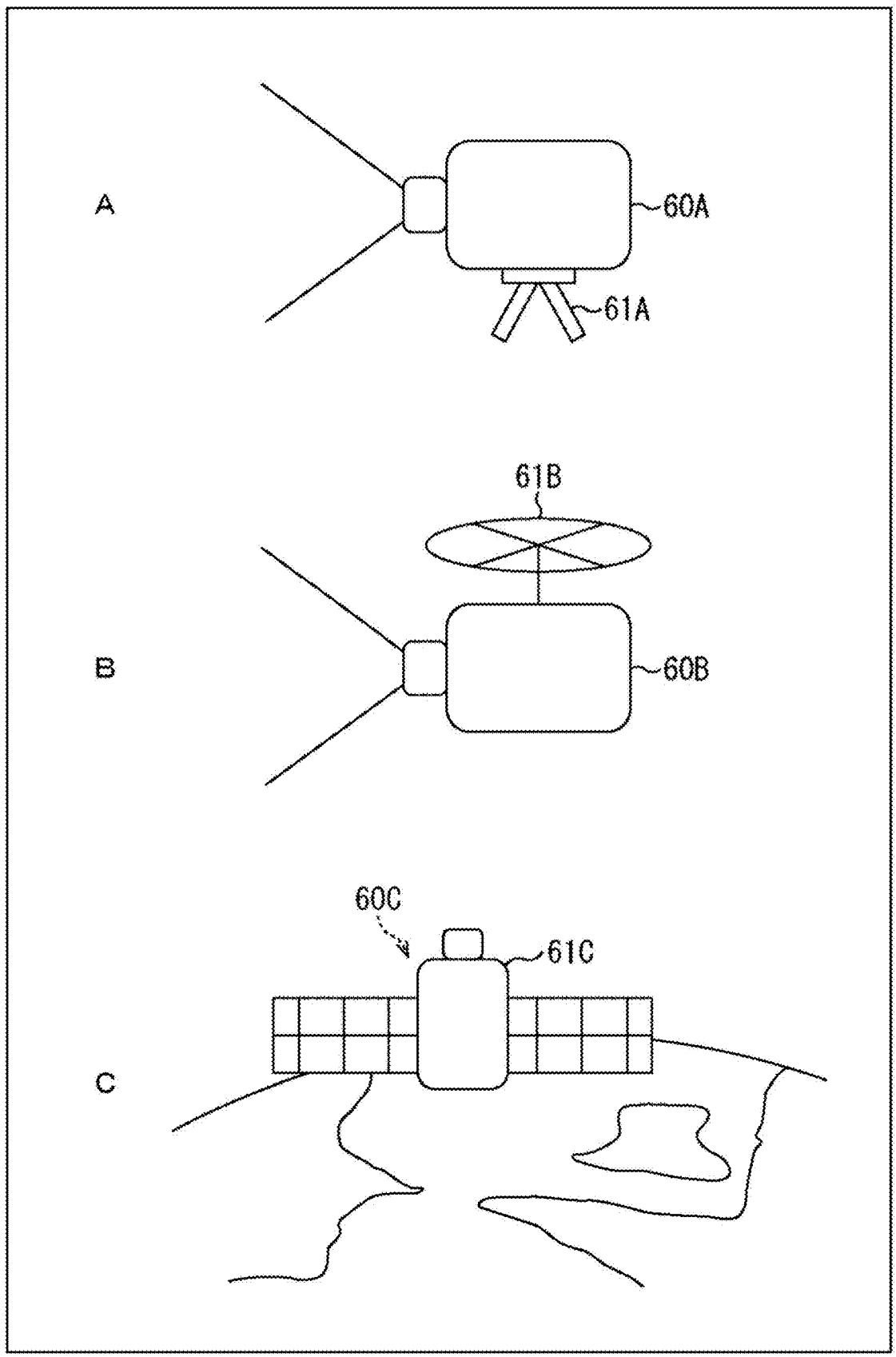
FIG. 37 is a view depicting a particular example of a measurement apparatus.

FIG. 37 exemplifies, as particular examples of the measurement apparatus 60 of FIG. 34 or 36, a fixed point measurement apparatus 60A that performs fixed point observation, a moving measurement apparatus 60B that performs moving observation and a satellite measurement apparatus 60C that performs measurement from an artificial satellite.

The fixed point measurement apparatus 60A depicted in A of FIG. 37 is fixed at a position, at which the inspection object 50 can be measured (sensed), by fixed legs 61A, and transmits a measurement signal (measurement value) measured there to the processing apparatus 70 (FIG. 34 or 36), for example, utilizing wireless communication or the like. The processing apparatus 70 can determine an inspection index (NDVI value) of the inspection object 50 measured by fixed point measurement by the fixed point measurement apparatus 60A by processing the measurement signal transmitted thereto from the fixed point measurement apparatus 60A.

The moving measurement apparatus 60B depicted in B of FIG. 37 is, for example, an unmanned aerial vehicle (UAV: Unmanned Aerial Vehicle), and flies by rotation of a rotary wing 61B in the form of a propeller and measures (shooting from a high level) the inspection object 50 from the sky. The moving measurement apparatus 60B transmits a measurement signal (measurement value) measured there utilizing, for example, wireless communication or the like to the processing apparatus 70 (FIG. 34 or 36). The processing apparatus 70 can determine an inspection index (NDVI value) of the inspection object 50 measured by moving measurement by the moving measurement apparatus 60B by processing the measurement signal transmitted thereto from the moving measurement apparatus 60B.

It is to be noted that the moving measurement apparatus 60B may store, for example, a flight route in advance as coordinate data such that it autonomously flies using position information of the GPS (Global Positioning System) or the like in addition to radio control. Further, while it is described that the moving measurement apparatus 60B in B of FIG. 37 is a rotary wing aircraft having the rotary wing 61B, the moving measurement apparatus 60B may be a fixed wind aircraft.

The satellite measurement apparatus 60C depicted in C of FIG. 37 is installed in an artificial satellite 61C. In the artificial satellite 61C, a measurement signal obtained by measurement (image pickup from the artificial satellite 61C) by the satellite measurement apparatus 60C (for example, a measurement value according to a satellite image) is transmitted to the processing apparatus 70 (FIG. 34 or 36) through a predetermined communication route. The processing apparatus 70 can determine an inspection index (NDVI value) of the inspection object 50 measured from the artificial satellite 61C by processing a measurement signal transmitted thereto from the satellite measurement apparatus 60C.

(Measurement Using Reference Transmission Plate)

Incidentally, while the description given above describes a case in which an inspection index (NDVI value) of the inspection object 50 is calculated by the vegetation inspection apparatus 10 utilizing the reference reflector plate 101, it is possible to utilize a transmittance characteristic in place of a reflectance characteristic of the reference reflector plate 101.

For example, by using a transmission filter having a spectral transmittance characteristic close to a spectral reflectance characteristic of the inspection object 50 (hereinafter referred to as reference transmission plate), it is possible to determine a correction gain, correct the measurement spectral ratio (R/IR ratio) of the inspection object 50 under the measurement light source L1 and remove the light source dependency upon measurement of an inspection index (NDVI value) of the inspection object 50 similarly as in the case where the reference reflector plate 101 is used.

While the foregoing description describes the first design process to third design process of a spectral reflectance as a design process of the reference reflector plate 101, design of a reference transmission plate can be performed similarly to the design process of them.

In particular, in the first design process (FIG. 8) of a spectral reflectance, the reference reflector plate 101 is designed using an average spectral reflectance of plants of different vegetations as a target spectral reflectance. Here, where a reference transmission plate is to be used, the reference transmission plate may be designed using an average spectral transmittance of plants of different vegetations as a target spectral transmittance.

Meanwhile, in the second design process (FIGS. 9 to 13) of a spectral reflectance, the reference reflector plate 101 is designed using a spectral reflectance characteristic calculated by multiplying an average spectral reflectance by an adjustment gain according to a minimum reflectance as a target spectral reflectance. Here, where a reference transmission plate is to be used, the reference transmission plate may be designed using a spectral transmittance characteristic calculated by multiplying an average spectral transmittance by an adjustment gain according to a minimum transmittance as a target spectral transmittance.

On the other hand, in the third design process (FIGS. 14 to 18) of a spectral reflectance, the reference reflector plate 101 is designed using a spectral reflectance characteristic calculated by multiplying an average spectral reflectance by an adjustment gain according to a maximum reflectance as a target spectral reflectance. Here, where a reference transmission plate is to be used, the reference transmission plate may be designed using a spectral transmittance characteristic calculated by multiplying an average spectral transmittance by an adjustment gain according to a maximum transmittance as a target spectral transmittance.

In the following, a configuration where a reference transmission plate designed by the design processes described hereinabove is used in place of the reference reflector plate 101 to perform measurement of an inspection index (NDVI value) of the inspection object 50 is described.

However, since it is necessary, in measurement in which a reference transmission plate is used, to provide a sensor 103 for measuring transmission light from the reference transmission plate, a plurality of sensors 103 are required. In this case, a configuration in which the plurality of sensors 103 are accommodated in the same housing (hereinafter referred to as monocular configuration) and another configuration in which the plurality of sensors 103 are accommodated in different housings from each other (hereinafter referred to as compound eye configuration). In the following description, the monocular configuration and the compound eye configuration are described in order.

(1) Monocular Configuration
(Configuration of Vegetation Inspection Apparatus)

Figure 38:
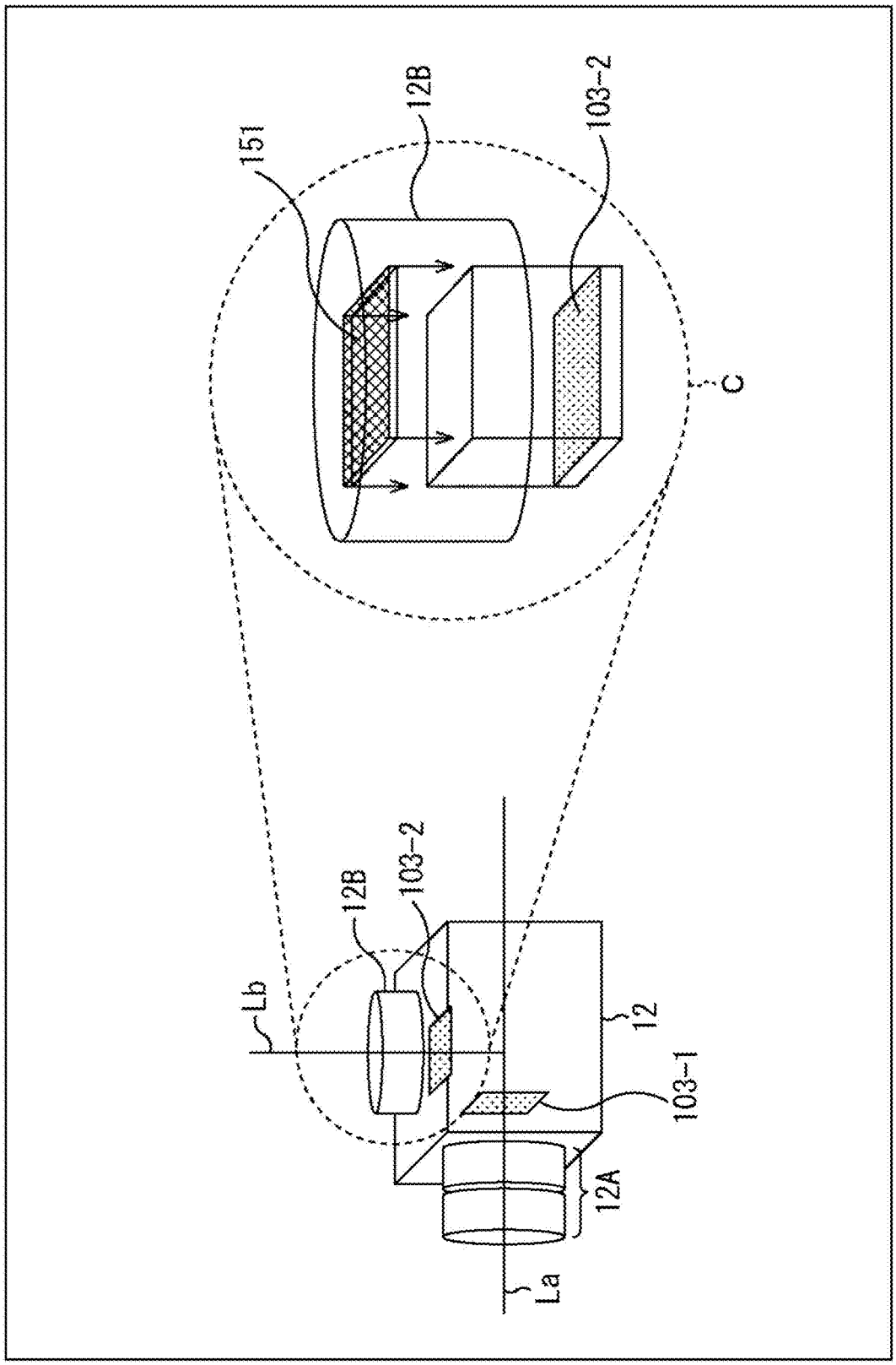
FIG. 38 is a perspective view depicting an example of a configuration of an appearance of a vegetation inspection apparatus where a monocular configuration is adopted.

FIG. 38 is a perspective view depicting an example of a configuration of an appearance of a vegetation inspection apparatus where the monocular configuration is adopted.

Referring to FIG. 38, in the vegetation inspection apparatus 12, a tight incidence section 12A and another light incidence section 12B are formed at a left side face side and an upper face side of a housing thereof such that light is introduced therethrough. Further, a sensor 103-1 and another sensor 103-2 are provided in the inside of the vegetation inspection apparatus 12. It is to be noted that, although the light incidence section 12A and the light incidence section 12B are each formed in a cylindrical shape that is hollow in the inside thereof, they have a role also as a cover.

In particular, in the vegetation inspection apparatus 12, light from the light incidence section 12A side (reflection light) enters along an optical axis La and is received by a sensor face of the sensor 103-1. Then, the sensor 103-1 measures an R channel value and an IR channel value according to the light (reflection light) from the inspection object 50 and outputs a measurement signal (measurement values) obtained as a result of the measurement to the correction processing unit 105 at a succeeding stage.

Further, in the vegetation inspection apparatus 12, light (sun light) from the light incidence section 12B side enters along an optical axis Lb.

Here, is the inside of a circle C represented by a broken line in FIG. 38, part of the vegetation inspection apparatus 12 at the light incidence section 12B side is depicted in an enlarged scale. As depicted here, a reference transmission plate 151 is provided on the optical axis Lb at the inner side of the light incidence section 12B having a cylindrical shape. The reference transmission plate 151 is designed, for example, by a design process similar to the first design process to the third design process (FIGS. 7 to 18) of a spectral reflectance and has an average spectral transmittance characteristic, a spectral transmittance characteristic according to a minimum transmittance or a spectral transmittance characteristic according to a maximum transmittance. It is to be noted that, in the light incidence section 12B, the reference transmission plate 151 is attached in a direction of an arrow mark in the figure.

In particular, light (sun light) from the light incidence section 12B side is transmitted by the reference transmission plate 151, and the transmission light is received by the sensor face of the sensor 103-2. Then, the sensor 103-2 measures an R channel value and an IR channel value according to the light transmitted by the reference transmission plate 151 (transmission light) and outputs a measurement signal (measurement values) obtained as a result of the measurement to the correction processing unit 105 at the succeeding stage.

Since the vegetation inspection apparatus 12 adopts the monocular configuration as described above, reflection light reflected by the inspection object 50 and transmission light transmitted by the reference transmission plate 151 are measured by the sensor 103-1 and the sensor 103-2 provided in the same housing, respectively. Now, a detailed internal configuration of the vegetation inspection apparatus 12 depicted in FIG. 38 is described with reference to FIG. 39.

Figure 39:
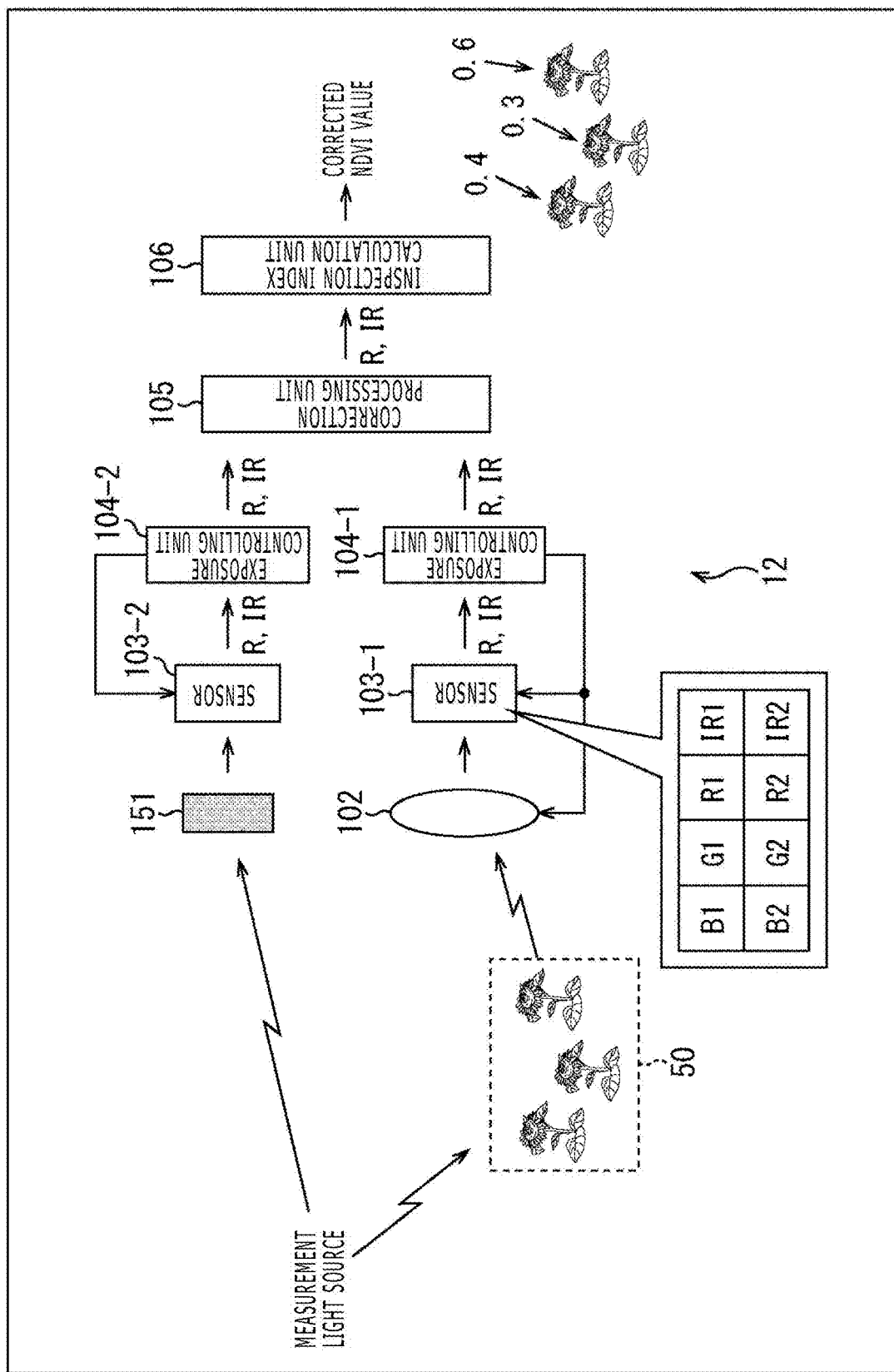
FIG. 39 is a view depicting as example of a configuration of the vegetation inspection apparatus where a monocular configuration is adopted.

Referring to FIG. 39, the vegetation inspection apparatus 12 is configured from a reference transmission plate 151, a lens 102, a sensor 103-1 and another sensor 103-2, an exposure controlling unit 104-1 and another exposure controlling unit 104-2, a correction processing unit 105 and an inspection index calculation unit 106.

It is to be noted that, in the vegetation inspection apparatus 12 of FIG. 39, portions same as the blocks configuring the vegetation inspection apparatus 10 of FIG. 1 described hereinabove are denoted by like reference characters, and description of them is suitably omitted.

In particular, in FIG. 39, in comparison with FIG. 1, the reference transmission plate 151 is provided in place of the reference reflector plate 101, and in addition to the sensor 103-1 and the exposure controlling unit 104-1 provided on the system of the lens 102 side, the sensor 103-2 and the exposure controlling unit 104-2 are provided also on the system of the reference transmission plate 151 side. It is to be noted that, as described hereinabove, the lens 102 and the sensor 103-1 are provided on the optical axis La. Meanwhile, the reference transmission plate 151 and the sensor 103-2 are provided on the optical axis La.

In FIG. 39, the reference transmission plate 151 is configured, for example, from a diffuse plate (diffuser plate) or the like. For example, the reference transmission plate 151 has an average spectral transmittance characteristic, a spectral transmittance characteristic according to a minimum transmittance or a spectral transmittance characteristic according to a maximum transmittance by being designed by a design process similar to the first design process to the third design process (FIGS. 7 to 18) of a spectral reflectance described hereinabove.

It is to be noted that, although a transmission plate having a spectral transmittance characteristic close to a spectral reflectance characteristic of the inspection object 50 can be used as the reference transmission plate 151, the reference transmission plate 151 may otherwise be configured from a plurality of transmission plates for individual wavelengths to be measured similarly to the reference reflector plate 101 depicted in FIG. 30.

The sensor 103-1 detects light (reflection light) from the inspection object 50 incident thereto through the lens 102 and outputs a measurement signal (measurement value) obtained as a result of the detection similarly to the sensor 103 (FIG. 1). The exposure controlling unit 104-1 controls the components of the lens 102 and the sensor 103-1 to perform exposure control similarly to the exposure controlling unit 104 (FIG. 1).

The sensor 103-2 detects light (transmission light) transmitted by the reference transmission plate 151 and outputs a measurement signal (measurement value) obtained as a result of the transmission similarly to the sensor 103 (FIG. 1). The exposure controlling unit 104-2 controls the components of the sensor 103-2 to perform exposure control similarly to the exposure controlling unit 104 (FIG. 1).

The correction processing unit 105 performs a correction process for correcting the spectral ratio (R/IR ratio) between the R channel value and the IR channel value on the basis of the measurement signals (measurement values) supplied thereto from the sensor 103-1 and the sensor 103-2 and supplies information indicative of the spectral ratio (R/IR ratio) after corrected to the inspection index calculation unit 106.

The inspection index calculation unit 106 uses the information supplied thereto from the correction processing unit 105 and indicative of the measurement spectral ratio (R/IR ratio) of the inspection object 50 after corrected to calculate an inspection index (NDVI value) of the inspection object 50 and outputs the inspection index (NDVI value).

The vegetation inspection apparatus 12 is configured in such a manner as described above.

Here, a process executed by the vegetation inspection apparatus 12 is particularly described below. In particular, the vegetation inspection apparatus 12 determines the reference spectral ratio (R/IR ratio) of the reference transmission plate 151 under the reference light source L0 in advance preceding to measurement of the inspection index (NDVI value) of the inspection object 50 under the measurement light source L1. Here, measurement of the reference transmission plate 151 under the reference light source L0 is performed similarly to the measurement of the reference reflector plate 101 under the reference light source L0 described hereinabove with reference to FIGS. 19 and 20.

Thereafter, upon measurement of the inspection index (NDVI value) of the inspection object 50 under the measurement light source L1, the vegetation inspection apparatus 12 uses a correction gain determined from the reference spectral ratio (R/IR ratio) of the reference transmission plate 151 and the measurement spectral ratio (R/IR ratio) of the reference transmission plate 151 under the measurement light source L1 to correct the measurement spectral ratio (R/IR ratio) of the inspection object 50 under the measurement light source L1, and measures the inspection index (NDVI value) of the inspection object 50.

Here, measurement of the inspection index (NDVI value) of the inspection object 50 under the measurement light source L1 is performed similarly to the measurement of the inspection index (NDVI value) of the inspection object 50 under the measurement light source L1 described hereinabove with reference to FIGS. 22 and 23 or FIGS. 24 and 25. In this manner, in the vegetation inspection apparatus 12, since correction based on the correction gain calculated using the reference transmission plate 151 having a characteristic according to the inspection object 50 is performed, the light source dependency upon measurement of the inspection index (NDVI value) of the inspection object 50 under the measurement light source L1 can be moved.

Further, where the reference reflector plate 101 is used in order to correct a variation of the light source (sun light), it is necessary to remove the influence of specular reflection of the reference reflector plate 101. However, according to the vegetation inspection apparatus 12, since the light source (sun light) is measured directly using the reference transmission plate 151 in place of the reference reflector plate 101, there is no necessity to take the influence of specular reflection as in the case where the reference reflector plate 101 is used into consideration.

It is to be noted that, since, in the vegetation inspection apparatus 12, a plurality of sensors, namely, the sensor 103-1 and the sensor 103-2, are provided in the same housing, a dispersion may occur in spectral characteristic such as the sensitivity ratio between the R channel and the IR channel among different sensors. Therefore, preferably the vegetation inspection apparatus 12 adopts the configuration depicted in FIG. 24 such that it calculates in advance a spectral ratio for normalization taking, for example, the spectral characteristic of the reference light source L0 and the spectral characteristic of the sensor 103-1 and the sensor 103-2 into consideration. This makes it possible in the vegetation inspection apparatus 12 to normalize the reference light source L0 and the components of the sensors by dividing the measurement spectral ratio after correction by the spectral ratio for normalization calculated in advance, and a dispersion in spectral characteristic among the sensors can be suppressed.

(2) Compound Eye Configuration
(Configuration of Vegetation Inspection Apparatus)

Figure 40:
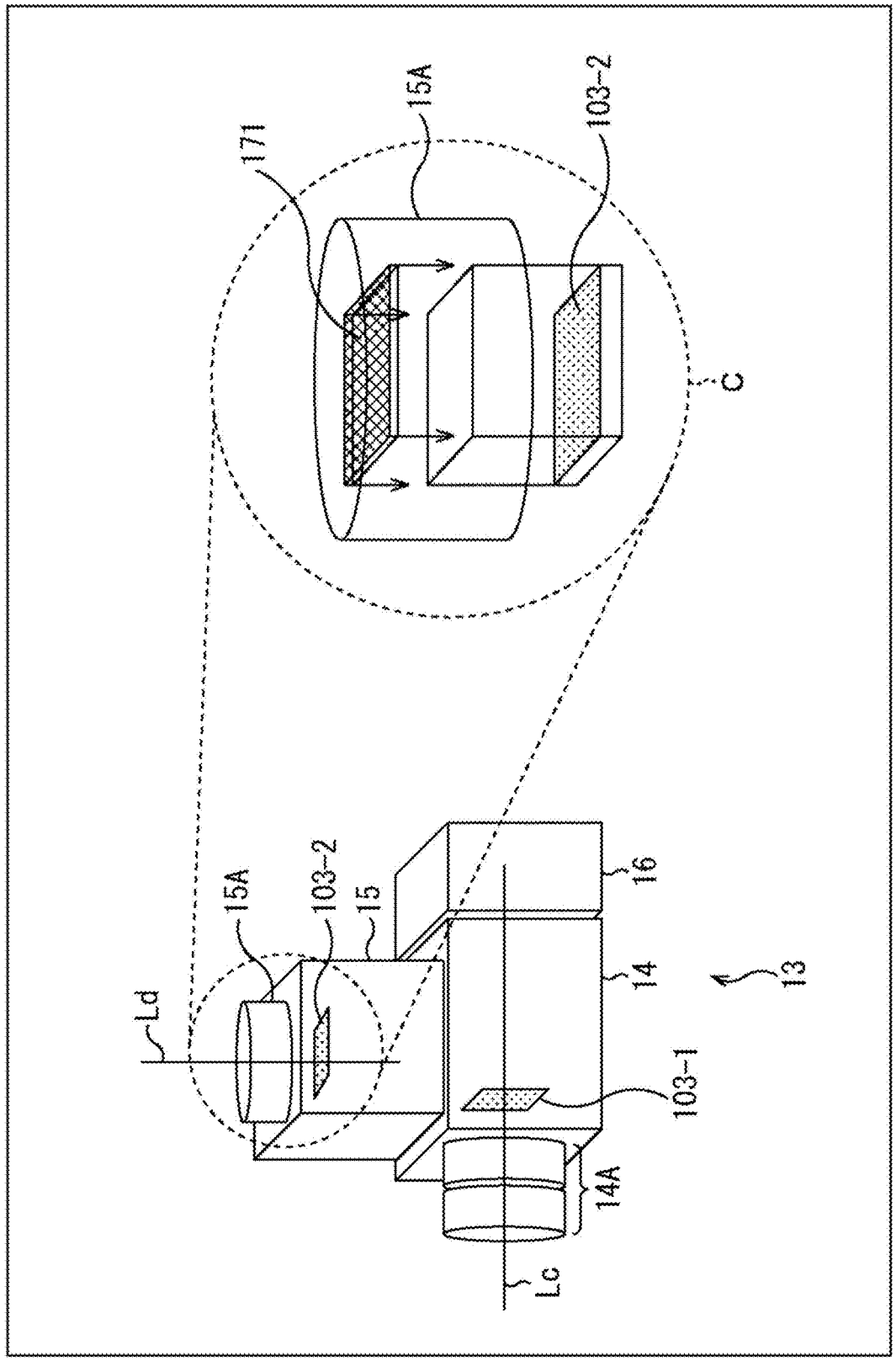
FIG. 40 is a perspective view depicting an example of a configuration of an appearance of a vegetation inspection apparatus where a compound eye configuration is adopted.

FIG. 40 is a perspective view of an example of a configuration of an appearance of the vegetation inspection apparatus where the compound eye configuration is adopted.

Referring to FIG. 40, the vegetation inspection apparatus 13 is configured from a measurement unit 14, another measurement unit 15 and a processing unit 16. Further, in the vegetation inspection apparatus 13, the measurement unit 14 and the processing unit 16 are connected to each other and the measurement unit 15 and the processing unit 16 are connected to each other individually through a predetermined interface.

In FIG. 40, the measurement unit 14 has formed at a left side face side of a housing thereof a light incidence section 14A having a cylindrical shape that is hollow in the inside thereof such that light enters through the light incidence section 14A. Further, a sensor 103-1 is provided in the inside of the measurement unit 14.

In particular, light (reflection light) from the light incidence section 14A side enters the measurement unit 14 along an optical axis Lc and is received by the sensor face of the sensor 103-1. The sensor 103-1 measures the R channel value and the IR channel value in response to light (reflection light) from the inspection object 50 and outputs measurement values obtained by the measurement to the processing unit 16 through a predetermined interface.

The measurement unit 15 has formed at an upper face side of the housing thereof a light incidence section 15A that has a cylindrical shape that is hollow in the inside thereof such that light enters through the light incidence section 15A. Further, a sensor 103-2 is provided in the inside of the measurement unit 15. In particular, light (sun light) from the light incidence section 15A enters the measurement unit 15 along an optical axis Ld.

Here, in the inside of a circle C represented by a broken line of FIG. 40, part of the measurement unit 15 at the light incidence section 15A side is depicted in an enlarged scale. As depicted herein, a reference transmission plate 171 is provided on the optical axis Ld in the inside of the light incidence section 15A having a cylindrical shape. The reference transmission plate 171 has, for example, an average spectral transmittance characteristic, a spectral transmittance characteristic according to a minimum transmittance or a spectral transmittance characteristic according to a maximum transmittance similarly to the reference transmission plate 151 (FIG. 38).

In particular, in the measurement unit 15, light (sun light) from the light incidence section 15A side is transmitted through the reference transmission plate 171, and the transmission light is received by the sensor face of the sensor 103-2. Then, the sensor 103-2 measures the R channel value and the IR channel value according to the light (transmission light) transmitted through the reference transmission plate 171 and outputs measurement values obtained by the measurement to the processing unit 16 through a predetermined interface.

The processing unit 16 is configured, for example, from an FPGA (Field Programmable Gate Array), a personal computer or the like. To the processing unit 16, measurement values are inputted from the measurement unit 14 and the measurement unit 15 through a predetermined interface. The processing unit 16 determines an inspection index (NDVI value) of the inspection object 50 on the basis of the measurement values from the measurement unit 14 and the measurement unit 15.

Since the vegetation inspection apparatus 13 has a compound eye configuration as described above, reflection light reflected by the inspection object 50 and transmission light transmitted through the reference transmission plate 171 are measured by the sensor 103-1 and the sensor 103-2 provided in the housings different from each other, respectively. Now, a detailed internal configuration of the vegetation inspection apparatus 13 depicted in FIG. 40 is described with reference to FIG. 41.

Figure 41:
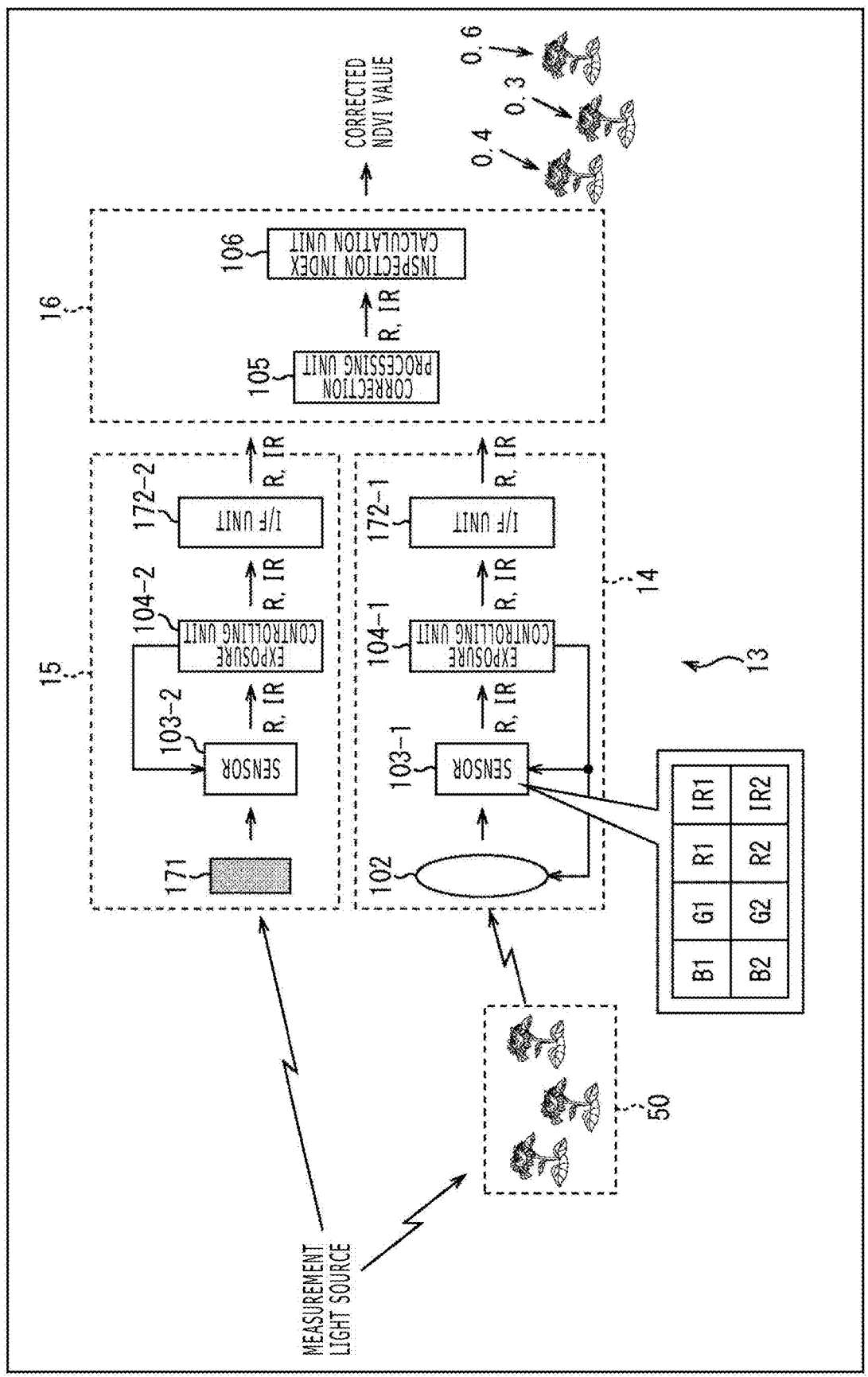
FIG. 41 is a view depicting an example of a configuration of a vegetation inspection apparatus where a compound eye configuration is adopted.

Referring to FIG. 41, the vegetation inspection apparatus 13 is configured from a measurement unit 14, another measurement unit 15 and a processing unit 16. The measurement unit 14 is configured from a lens 102, a sensor 103-1, an exposure controlling unit 104-1 and an I/F unit 172-1. Meanwhile, the measurement unit 15 is configured from a reference transmission plate 171, a sensor 103-2, an exposure controlling unit 104-2 and an I/F unit 172-2. Further, the processing unit 16 is configured from a correction processing unit 105 and an inspection index calculation unit 106.

It is to be noted that, in the vegetation inspection apparatus 12 of FIG. 41, like portions to the blocks configuring the vegetation inspection apparatus 10 described hereinabove with reference to FIG. 1 are denoted by like reference characters, and description of them is suitably omitted. In particular, in comparison with FIG. 1, the components in FIG. 41 are arranged separately as the measurement unit 14, measurement unit 15 and processing unit 16, and the I/F unit 172-1 and the I/F unit 172-2 are provided at connection locations between the measurement unit 14 and measurement unit 15 and the processing unit 16, respectively.

Further, in FIG. 41, in comparison with FIG. 1, the reference transmission plate 171 is provided in place of the reference reflector plate 101, and separately from the sensor 103-1 and the exposure controlling unit 104-1 provided in the system of the lens 102 side, the sensor 103-2 and the exposure controlling unit 104-2 are provided also in the system of the reference transmission plate 171 side. It is to be noted that the lens 102 and the sensor 103-1 are provided on the optical axis to as described hereinabove. Further, the reference transmission plate 171 and the sensor 103-2 are provided on the optical axis Ld.

In the measurement unit 14, the sensor 103-1 detects light (reflection light) from the inspection object 50 incident through the lens 102 and outputs a measurement value obtained as a result of the detection. The exposure controlling unit 104-1 performs exposure control by controlling the components of the lens 102 and the sensor 103-1. The I/F unit 172-1 outputs the measurement value from the sensor 103-1 to the processing unit 16.

In the measurement unit 15, the sensor 103-2 detects light (transmission light) transmitted through the reference transmission plate 171 and outputs a measurement value obtained as a result of the detection. The exposure controlling unit 104-2 performs exposure control by controlling the components of the sensor 103-2. The I/F unit 172-2 outputs the measurement value from the sensor 103-2 to the processing unit 16.

In the processing unit 16, the measurement value from the I/F unit 172-1 of the measurement unit 14 and the measurement value from the I/F unit 172-2 of the measurement unit 15 are inputted to the correction processing unit 105.

The correction processing unit 105 performs a correction process for correcting the spectral ratio (R/IR ratio) between the R channel value and the IR channel value on the basis of the measurement values inputted from the measurement unit 14 and the measurement unit 15, and supplies information indicative of the spectral ratio (R/IR ratio) after corrected to the inspection index calculation unit 106.

The inspection index calculation unit 106 uses the information supplied thereto from the correction processing unit 105 and indicative of the measurement spectral ratio (R/IR ratio) of the inspection object 50 to calculate an inspection index (NDVI value) of the inspection object 50 and outputs the inspection index (NDVI value).

The vegetation inspection apparatus 13 is configured in such a manner as described above.

Here, a process executed by the vegetation inspection apparatus 13 is described particularly below. In particular, the vegetation inspection apparatus 13 determines in advance a reference spectral ratio (R/IR ratio) of the reference transmission plate 171 under the reference light source L0 preceding to measurement of an inspection index (NDVI value) of the inspection object 50 under the measurement light source L1. Here, measurement of the reference transmission plate 171 under the reference light source L0 is performed similarly to the measurement of the reference reflector plate 101 under the reference light source L0 described hereinabove with reference to FIGS. 19 and 20.

Thereafter, upon measurement of the inspection index (NDVI value) of the inspection object 50 under the measurement light source L1, the vegetation inspection apparatus 13 uses a correction gain determined from the reference spectral ratio (R/IR ratio) of the reference transmission plate 171 and the measurement spectral ratio (R/IR ratio) of the reference transmission plate 171 under the measurement light source L1 to correct the measurement spectral ratio (R/IR ratio) of the inspection object 50 under the measurement light source L1, and then measures the inspection index (NDVI value) of the inspection object 50.

Here, the measurement of the inspection index (NDVI value) of the inspection object 50 under the measurement light source L1 is performed similarly to the measurement of the inspection index (NDVI value) of the inspection object 50 under the measurement light source L1 described hereinabove with reference to FIGS. 22 and 23 or FIGS. 24 and 25. In this manner, since the vegetation inspection apparatus 13 performs correction based on the correction gain calculated using the reference transmission plate 171 having a characteristic according to the inspection object 50, the light source dependency upon measurement of the inspection index (NDVI value) of the inspection object 50 under the measurement light source L1 can be removed. Further, since also the vegetation inspection apparatus 13 uses the reference transmission plate 171, there is no necessity to take the influence of specular reflection as in the case in which the reference reflector plate 101 is used into consideration.

It is to be noted that, in the vegetation inspection apparatus 13, since a plurality of sensors including the sensor 103-1 and the sensor 103-2 are provided is different housings, it is supposed that a dispersion occurs in spectral characteristic among sensors similarly as in the vegetation inspection apparatus 12. Therefore, also in the vegetation inspection apparatus 13, by adopting the configuration depicted in FIG. 24 such that a spectral ratio for normalization is calculated in advance similarly in the vegetation inspection apparatus 12, a dispersion in spectral characteristic among the sensors can be suppressed.

<6. Configuration of Computer>

Figure 42:
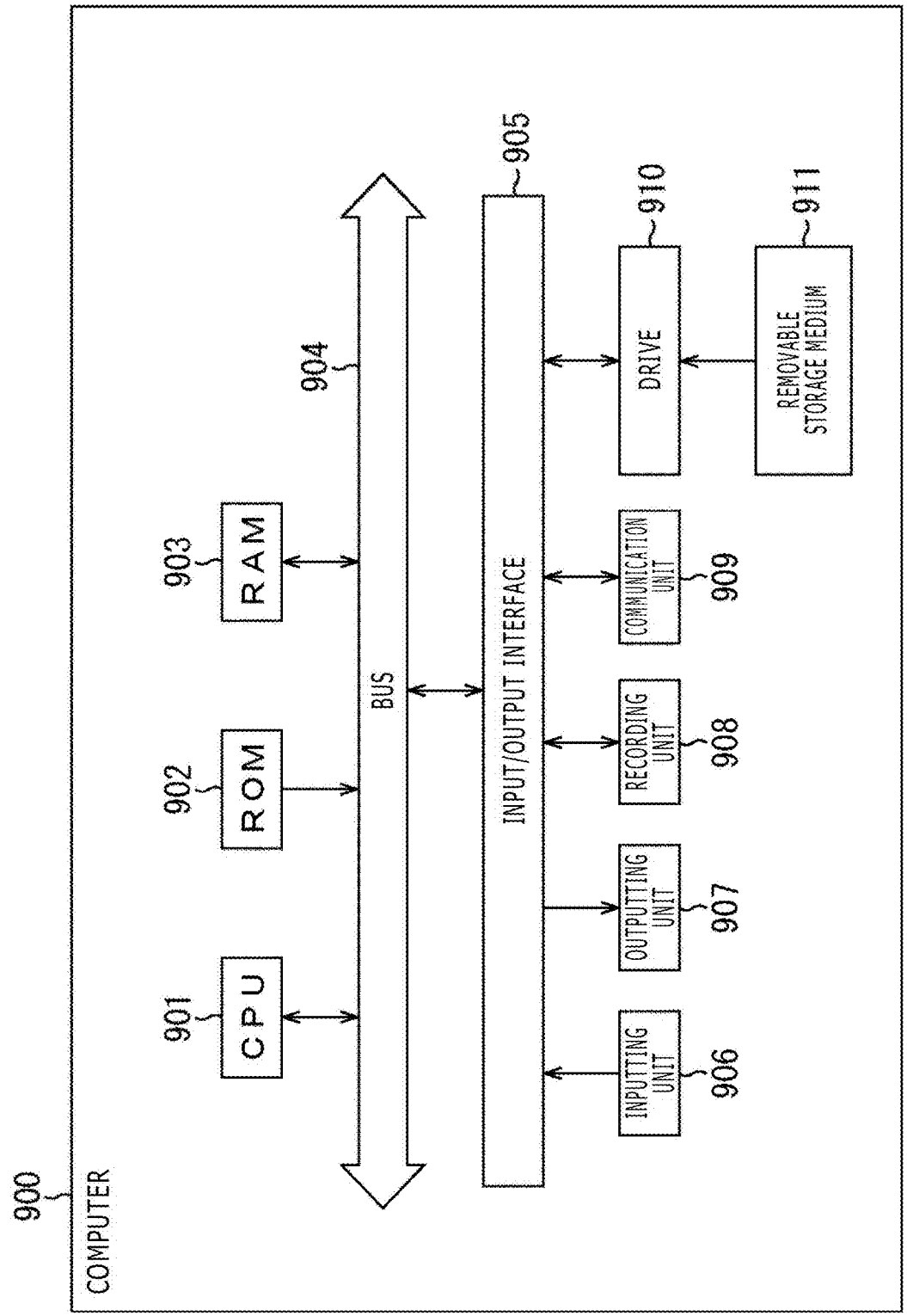
FIG. 42 is a view depicting an example of a configuration of a computer.

While the series of processes described above can be executed by hardware, it may otherwise be executed by software. Where the series of processes is executed by software, a program that constructs the software is installed into a computer. FIG. 42 is a view depicting an example of a configuration of hardware of a computer that executes the series of processes described hereinabove in accordance with a program.

In the computer 900, a CPU (Central Processing Unit) 901, a ROM (Read Only Memory) 902 and a RAM (Random Access Memory) 903 are connected to each other by a bus 904. To the bus 904, an input/output interface 905 is connected further. To the input/output interface 905, an inputting unit 906, an outputting unit 907, a recording unit 908, a communication unit 909 and a drive 910 are connected.

The inputting unit 906 is configured from a keyboard, a mouse, a microphone and so forth. The outputting unit 907 is configured from a display unit, a speaker and so forth. The recording unit 908 is configured from a hard disk, a nonvolatile memory and so forth. The communication unit 909 is configured from a network interface and so forth. The drive 910 drives a removable storage medium 911 such as a magnetic disk, an optical disk, a magneto-optical disk or a semiconductor memory.

In the computer 900 configured in such a manner as described above, the CPU 901 loads a program recorded, for example, in the ROM 902 or the recording unit 908 into the RAM 903 through the input/output interface 905 and the bus 904 and executes the program to perform the series of processes described hereinabove.

The program executed by the computer 900 (CPU 901) can be recorded on and provided as the removable storage medium 911, for example, as a package medium or the like. Further, the program can be provided through a wired or wireless transmission medium such as a local area network, the Internet or a digital satellite broadcast.

In the computer 900, the program can be installed into the recording unit 908 through the input/output interface 905 by loading the removable storage medium 911 into the drive 910. Alternatively, the program can be received by the communication unit 909 through a wired or wireless transmission medium and installed into the recording unit 908. Alternatively, the program may be installed in advance into the ROM 902 or the recording unit 908.

It is to be noted that, in the present specification, the processes performed in accordance with the program by the computer may not necessarily be performed in a time series in accordance with an order described as the flow charts. In other words, the processes performed in accordance with the program by the computer include also processes executed in parallel or individually (for example, parallel processing or processing by objects). Further, the program may be processed by one computer (processor) or may be processed by distributed processing by a plurality of computers.

It is to be noted that the embodiment of the present technology is not limited to the embodiment described hereinabove but can be altered in various manners without departing from the subject matter of the present technology. For example, it is possible to adopt a form that includes all or part of a plurality of embodiments described hereinabove.

Further, the present technology can take such configurations as described below.

(1)

An inspection apparatus, including:

a correction gain calculation unit configured to calculate a correction gain of a spectrum based on reference spectral information, under a reference light source, of a reference reflector plate or a reference transmission plate having a characteristic according to an inspection object and measurement spectral information of the reference reflector plate or the reference transmission plate obtained by sensing under a measurement light source; and a correction unit configured to correct measurement spectral information of the inspection object obtained the sensing under the measurement light source based on the calculated correction gain.

(2)

The inspection apparatus according to (1), in which the reference spectral information is a reference spectral ratio, the measurement spectral information of the reference reflector plate or the reference transmission plate is a measurement spectral ratio of the reference reflector plate or the reference transmission plate, and the measurement spectral information of the inspection object is a measurement spectral ratio of the inspection object.

(3)

The inspection apparatus according to (2), in which the reference reflector plate has characteristics according to spectral reflectances of a plurality of inspection objects having characteristics different from each other and has characteristics in which an adjustment gain to be used for multiplication is changed for each of wavelength bands according to components that become a target of the reference spectral ratio, the measurement spectral ratio of the reference reflector plate and the measurement spectral ratio of the inspection object.

(4)

The inspection apparatus according to (3), in which the adjustment gain is determined for each of the wavelength bands according to the components that become a target from a ratio between an average reflectance and a minimum reflectance or a maximum reflectance of spectral reflectances in the wavelength band.

(5)

The inspection apparatus according to any one of (2) to (4), further including:

an inspection index calculation unit configured to calculate an inspection index of the inspection object based on the corrected measurement spectral ratio of the inspection object.

(6)

The inspection apparatus according to any one of (2) to (5), in which the correction gain calculation unit calculates the correction gain by dividing the reference spectral ratio of the reference reflector plate or the reference transmission plate by the measurement spectral ratio of the reference reflector plate or the reference transmission plate, and the correction unit corrects the measurement spectral ratio of the inspection object by multiplying the measurement spectral ratio of the inspection object by the correction gain.

(7)

The inspection apparatus according to any one of (1) to (6), further including:

where the reference reflector plate is used from between the reference reflector plate and the reference transmission plate, a sensor unit configured to sense the inspection object and the reference reflector plate under the measurement light source.

(8)

The inspection apparatus according to any one of (1) to (7), in which the reference reflector plate includes two or more reflector plates arranged spatially in a mosaic pattern.

(9)

The inspection apparatus according to any one of (2) to (8), in which the inspection object is a plant, the reference spectral ratio, the measurement spectral ratio of the reference reflector plate or the reference transmission plate and the measurement spectral ratio of the inspection object are ratios between a value of an R (red) component and an IR (infrared) component, and the inspection index is a normalized vegetation index (NDVI: Normalized Difference Vegetation Index).

(10)

The inspection apparatus according to any one of (2) to (9), further including:

a storage unit configured to store the reference spectral ratio calculated in advance, in which the correction gain calculation unit calculates the correction gain based on the reference spectral ratio read out from the storage unit.

(11)

The inspection apparatus according to (7), in which the sensor unit senses the inspection object and the reference reflector plate simultaneously with each other.

(12)

The inspection apparatus according to (11), is which
the reference reflector plate is attached to a given position so as to exist within an angle of view of a camera that has the sensor unit.

(13)

The inspection apparatus according to (2), in which
the reference transmission plate has characteristics according to spectral transmittances of a plurality of inspection objects having characteristics different from each other and has characteristics in which an adjustment gain to be used for multiplication is changed for each of wavelength bands according to components that become a target of the reference spectral ratio, the measurement spectral ratio of the reference transmission plate and the measurement spectral ratio of the inspection object.

(14)

The inspection apparatus according to (13), in which
the adjustment gain is determined for each of the wavelength bands according to the components that become a target from a ratio between an average transmittance and a minimum transmittance or a maximum transmittance of spectral transmittances in the wavelength band.

(15)

The inspection apparatus according to (1), (2), (13) or (14), further including:
where the reference transmission plate is used from between the reference reflector plate and the reference transmission plate, a first sensor unit configured to sense the inspection object under the measurement light source and a second sensor unit configured to sense the reference transmission plate under the measurement light source.

(16)

An inspection method, comprising the steps of:
calculating, based on reference spectral information a correction gain of a spectrum under a reference light source, of a reference reflector plate or a reference transmission plate having a characteristic according to an inspection object and measurement spectral information of the reference reflector plate or the reference transmission plate obtained by sensing under a measurement light source; and
correcting measurement spectral information of the inspection object obtained by the sensing under the measurement light source based on the calculated correction gain.

(17)

A program for causing a computer to function as:
a correction gain calculation unit configured to calculate a correction gain of a spectrum based on reference spectral information, under a reference light source, of a reference reflector plate or a reference transmission plate having a characteristic according to an inspection object and measurement spectral information of the reference reflector plate or the reference transmission plate obtained by sensing under a measurement light source; and
a correction unit configured to correct measurement spectral information of the inspection object obtained by the sensing under the measurement light source based on the calculated correction gain.

REFERENCE SIGNS LIST 10, 12, 13 Vegetation inspection apparatus, 11 Vegetation inspection system, 14, 15 Measurement unit, 16 Processing unit, 20 Spectral reflectance design apparatus, 60 Measurement apparatus, 60A Fixed point measurement apparatus, 60B Moving measurement apparatus, 60C Satellite measurement apparatus, 70 Processing apparatus, 80 Measurement processing apparatus, 90 Storage apparatus, 101 Reference reflector plate, 102 Lens, 103, 103-1, 103-2 Sensor, 104, 104-1, 104-2 Exposure controlling unit, 105 Correction processing unit, 106 Inspection index calculation unit, 111 Reference reflector plate R/IR ratio calculation unit, 112 Storage unit, 113 Correction gain calculation unit, 114 Measurement light correction unit, 121 Reference reflector plate R/IR ratio calculation unit, 122 R/IR ratio variation ratio calculation unit, 123 Inspection object R/IR ratio calculation unit, 124 Gain correction unit, 131 NDVI value calculation unit, 132 Normalization unit, 133 Storage unit, 151, 171 Reference transmission plate, 900 Computer, 901 CPU

The invention claimed is:

1. An inspection apparatus, comprising:
a correction gain calculation unit configured to calculate a correction gain of a spectrum based on reference spectral information, under a reference light source, of a reference reflector plate or a reference transmission plate having a characteristic according to an inspection object and measurement spectral information of the reference reflector plate or the reference transmission plate obtained by sensing under a measurement light source; and
a correction unit configured to correct measurement spectral information of the inspection object obtained by the sensing under the measurement light source based on the calculated correction gain.

2. The inspection apparatus according to claim 1, wherein
the reference spectral information is a reference spectral ratio,
the measurement spectral information of the reference reflector plate or the reference transmission plate is a measurement spectral ratio of the reference reflector plate or the reference transmission plate, and
the measurement spectral information of the inspection object is a measurement spectral ratio of the inspection object.

3. The inspection apparatus according to claim 2, further comprising:
a calculation unit configured to calculate an adjustment gain,
wherein the reference reflector plate has characteristics according to spectral reflectances of a plurality of inspection objects having characteristics different from each other and has characteristics in which the adjustment gain to be used for multiplication is changed for each of wavelength bands according to components that become a target of the reference spectral ratio, the measurement spectral ratio of the reference reflector plate and the measurement spectral ratio of the inspection object.

4. The inspection apparatus according to claim 3, wherein
the adjustment gain is determined for each of the wavelength bands according to the components that become a target from a ratio between an average reflectance and a minimum reflectance or a maximum reflectance of spectral reflectances in the wavelength band.

5. The inspection apparatus according to claim 2, further comprising:
an inspection index calculation unit configured to calculate an inspection index of the inspection object based on the corrected measurement spectral ratio of the inspection object.

6. The inspection apparatus according to claim 5, wherein the correction gain calculation unit calculates the correction gain by dividing the reference spectral ratio of the reference reflector plate or the reference transmission plate by the measurement spectral ratio of the reference reflector plate or the reference transmission plate, and
the correction unit corrects the measurement spectral ratio of the inspection object by multiplying the measurement spectral ratio of the inspection object by the correction gain.

7. The inspection apparatus according to claim 1, further comprising:
where the reference reflector plate is used from between the reference reflector plate and the reference transmission plate, a sensor unit configured to sense the inspection object and the reference reflector plate under the measurement light source.

8. The inspection apparatus according to claim 1, wherein the reference reflector plate includes two or more reflector plates arranged spatially in a mosaic pattern.

9. The inspection apparatus according to claim 2, wherein the inspection object is a plant,
each of the reference spectral ratio, the measurement spectral ratio of the reference reflector plate or the reference transmission plate and the measurement spectral ratio of the inspection object is a ratio between a value of an R (red) component and an IR (infrared) component, and
the inspection index is a normalized vegetation index (NDVI: Normalized Difference Vegetation Index).

10. The inspection apparatus according to claim 2, further comprising:
a storage unit configured to store the reference spectral ratio calculated in advance,
wherein the correction gain calculation unit calculates the correction gain based on the reference spectral ratio read out from the storage unit.

11. The inspection apparatus according to claim 7, wherein
the sensor unit senses the inspection object and the reference reflector plate simultaneously with each other.

12. The inspection apparatus according to claim 11, wherein
the reference reflector plate is attached to a given position so as to exist within an angle of view of a camera that has the sensor unit.

13. The inspection apparatus according to claim 2, further comprising:
a calculation unit configured to calculate an adjustment gain,
wherein the reference transmission plate has characteristics according to spectral transmittances of a plurality of inspection objects having characteristics different from each other and has characteristics in which the adjustment gain to be used for multiplication is changed for each of wavelength bands according to components that become a target of the reference spectral ratio, the measurement spectral ratio of the reference transmission plate and the measurement spectral ratio of the inspection object.

14. The inspection apparatus according to claim 13, wherein
the adjustment gain is determined for each of the wavelength bands according to the components that become a target from a ratio between an average transmittance and a minimum transmittance or a maximum transmittance of spectral transmittances in the wavelength band.

15. The inspection apparatus according to claim 1, wherein:
when the reference transmission plate is used, a first sensor unit senses the inspection object under the measurement light source and a second sensor unit senses the reference transmission plate under the measurement light source.

16. An inspection method, comprising the steps of:
calculating a correction gain of a spectrum based on reference spectral information, under a reference light source, of a reference reflector plate or a reference transmission plate having a characteristic according to an inspection object and measurement spectral information of the reference reflector plate or the reference transmission plate obtained by sensing under a measurement light source; and
correcting measurement spectral information of the inspection object obtained by the sensing under the measurement light source based on the calculated correction gain.

17. A non-transitory computer readable medium storing program code for inspection, the program code being executable by a computer to perform operations comprising:
calculating a correction gain of a spectrum based on reference spectral information, under a reference light source, of a reference reflector plate or a reference transmission plate having a characteristic according to an inspection object and measurement spectral information of the reference reflector plate or the reference transmission plate obtained by sensing under a measurement light source; and
correcting measurement spectral information of the inspection object obtained by the sensing under the measurement light source based on the calculated correction gain.

18. The inspection method according to claim 16, wherein
the reference spectral information is a reference spectral ratio,
the measurement spectral information of the reference reflector plate or the reference transmission plate is a measurement spectral ratio of the reference reflector plate or the reference transmission plate, and
the measurement spectral information of the inspection object is a measurement spectral ratio of the inspection object.

19. The non-transitory computer readable medium according to claim 17, wherein
the reference spectral information is a reference spectral ratio,
the measurement spectral information of the reference reflector plate or the reference transmission plate is a measurement spectral ratio of the reference reflector plate or the reference transmission plate, and
the measurement spectral information of the inspection object is a measurement spectral ratio of the inspection object.

* * * * *